(12) United States Patent
McLaughlin et al.

(10) Patent No.: US 12,060,438 B2
(45) Date of Patent: Aug. 13, 2024

(54) CYCLIC PEPTIDE COMPOUNDS AND METHODS OF USE THEREOF

(71) Applicant: MODULATION THERAPEUTICS, INC., Morgantown, WV (US)

(72) Inventors: Mark McLaughlin, Morgantown, WV (US); Lori Hazlehurst, Morgantown, WV (US)

(73) Assignee: Modulation Therapeutics, Inc., Morgantown, WV (US)

( * ) Notice: Subject to any disclaimer, the term of this patent is extended or adjusted under 35 U.S.C. 154(b) by 0 days.

(21) Appl. No.: 16/972,558

(22) PCT Filed: Jun. 5, 2019

(86) PCT No.: PCT/US2019/035652
§ 371 (c)(1),
(2) Date: Dec. 4, 2020

(87) PCT Pub. No.: WO2019/236747
PCT Pub. Date: Dec. 12, 2019

(65) Prior Publication Data
US 2021/0347826 A1     Nov. 11, 2021

Related U.S. Application Data

(60) Provisional application No. 62/680,904, filed on Jun. 5, 2018.

(51) Int. Cl.
 C07K 7/64   (2006.01)
 A61K 38/00  (2006.01)
(52) U.S. Cl.
 CPC .............. *C07K 7/64* (2013.01); *A61K 38/00* (2013.01)
(58) Field of Classification Search
 None
 See application file for complete search history.

(56) References Cited

U.S. PATENT DOCUMENTS

| | | | |
|---|---|---|---|
| 8,853,149 B2 * | 10/2014 | Hazlehurst | A61P 35/00 |
| | | | 514/1.1 |
| 10,011,635 B2 * | 7/2018 | Hazlehurst | C07K 14/705 |
| 2014/0322227 A1 | 10/2014 | Hazlehurst et al. | |
| 2016/0257712 A1 | 9/2016 | Hazlehurst et al. | |
| 2017/0174726 A1 * | 6/2017 | McLaughlin | G01N 33/68 |

FOREIGN PATENT DOCUMENTS

| | | | | |
|---|---|---|---|---|
| WO | 2010/022089 A2 | 2/2010 | | |
| WO | WO-2013170066 A1 * | 11/2013 | | A61K 38/08 |
| WO | 2015/048477 A1 | 4/2015 | | |
| WO | WO-2015153560 A1 * | 10/2015 | | C07K 14/00 |

OTHER PUBLICATIONS

Emmons et al. (Sci Rep. Jun. 2, 2017;7(1):2685) (Year: 2017).*
Mezo et al. (Biophysical Chemistry 103 (2003) 51-65) (Year: 2003).*
Kyle et al., "Prevalence of Monoclonal Gammopathy of Undetermined Significance," *N. Engl. J. Med.* 354:1362-1369, Mar. 30, 2006.
Tsuda et al., "Structure and Synthesis of an Immunoactive Lipopeptide, WS1279, of Microbial Origin," *Chem. Pharm. Bull.* 39(3):607-611, Mar. 1991.
Emmons et al., "MTI-101 treatment inducing activation of Stim1 and TRPCI expression is a determinant of response in multiple myeloma" *Scientific Reports* 7:1-12, 2017.
Gebhard et al., "MTI-101 (Cyclized HYD1) Binds a CD44 Containing Complex and Induces Necrotic Cell Death in Multiple Myeloma" *Small Molecule Therapeutics* 12(11):2446-2458, 2013.

* cited by examiner

*Primary Examiner* — Sergio Coffa
(74) *Attorney, Agent, or Firm* — Seed IP Law Group LLP

(57) ABSTRACT

Embodiments of the present disclosure generally relate to cyclic peptidomimetic compounds and methods for making the same. Other embodiments relate to a method of treating a disease by administering a pharmaceutically effective amount of a cyclic peptidomimetic disclosed herein, for example to treat cancer.

4 Claims, 1 Drawing Sheet
Specification includes a Sequence Listing.

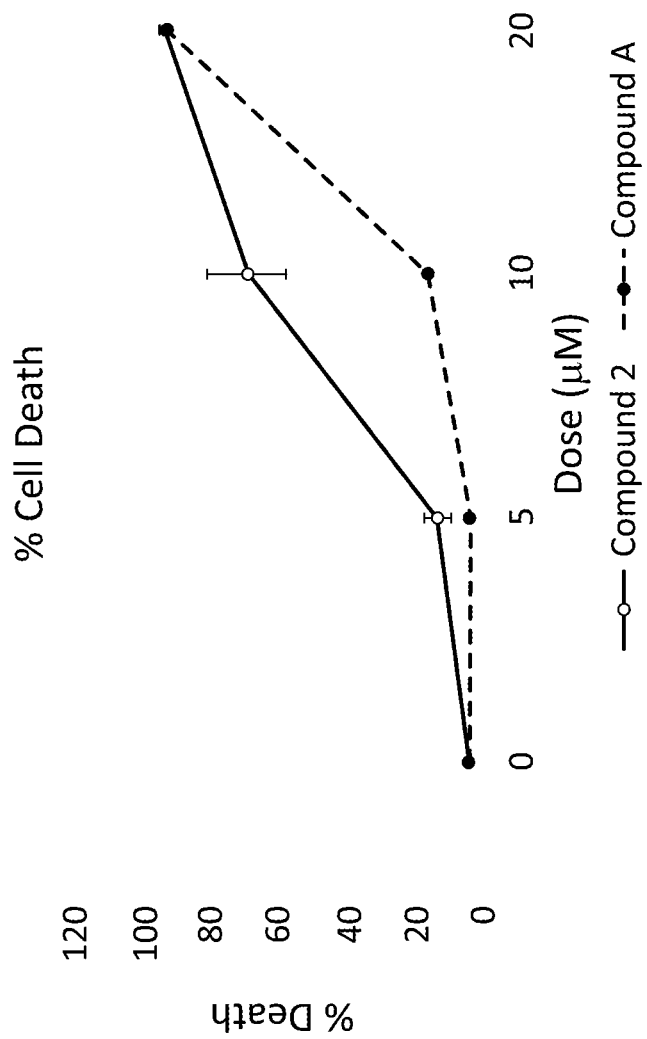

CYCLIC PEPTIDE COMPOUNDS AND METHODS OF USE THEREOF

The Sequence Listing associated with this application is provided in text format in lieu of a paper copy, and is hereby incorporated by reference into the specification. The name of the text file containing the Sequence Listing is 670131_403USPC_SEQUENCE_LISTING.txt. The text file is 42.7 KB, was created on Dec. 4, 2020, and is being submitted electronically via EFS-Web.

BACKGROUND

Technical Field

The present disclosure generally relates to compounds comprising a cyclic β-hairpin peptidomimetic suitable for use in treatment of various diseases, including cancer, and methods of making and using the same.

Background

Multiple myeloma is a cancer of the plasma cell, which primarily develops in the elderly population. The progression of the tumor is well understood, and it can be diagnosed by the presence of multiple myeloma cells in the bone marrow and monitored by the amount of antibody secretion from the clonal population of plasma cells. A premalignant condition known as monoclonal gammopathy of undetermined significance (MGUS) develops at certain rates in the US population: 3% at age 50, 5% at age 70, and 7% by age 85; approximately 1% of MGUS patients progress to multiple myeloma on an annual basis (Kyle R. A., et. al, *N. Engl. J. Med.* 354, 1362-1369 (2006)). The molecular causes for progression from MGUS to multiple myeloma are unknown. Despite highly specific and easily detectable biomarkers, many challenges still exist for multiple myeloma treatment. While some treatments have had some success against multiple myeloma cells, many challenges exist as a barrier to finding effective treatment.

Accordingly, there is a need in the art for improved compounds having utility for treating the aforementioned diseases and methods for using and preparing the same. Embodiments of the present disclosure provide this and related improvements.

BRIEF DESCRIPTION

Briefly, embodiments of the present disclosure relate to compounds comprising cyclic peptidomimetic compounds, as well as the preparation and use thereof. In particular, embodiments of compounds comprising cyclic β-hairpin peptidomimetic compounds disclosed herein have shown anti-cancer activity against cancer, such as multiple myeloma, EGFR-driven lung cancer, and prostate cancer. The applicant has discovered that some embodiments of these compounds with a linker, such as 3-aminopropyl and certain diverse side chains (e.g., substituted or unsubstituted amino acid derivatives), can significantly enhance the desired biological activity and bioavailability. In some embodiments, the applicant has unexpectedly discovered that attachment of a cysteine side chain significantly increases biological potency and activity, which is consistent with the additional positive charge from protonation of the cysteine N-terminus at physiological pH.

Accordingly, one embodiment of the present disclosure provides a compound having a structure of Formula (I):

$$X-L^1-N(R')R^2 \qquad (I)$$

or a pharmaceutically acceptable salt, tautomer, or stereoisomer thereof, wherein:
X is a cyclic β-hairpin peptidomimetic;
L is an optional linker;
$R^1$ is H; and
$R^2$ is H or a moiety comprising one or more amino acid residues or substituted derivatives thereof.

Another embodiment provides a pharmaceutical composition comprising a compound according to the embodiments disclosed herein and a pharmaceutically acceptable carrier or excipient.

Yet another embodiment provides a method for treatment of cancer, the method comprising administering an effective amount of a pharmaceutical composition as disclosed herein to a subject in need thereof.

These and other aspects will be evident upon reference to the attached drawings and following detailed description.

BRIEF DESCRIPTION OF THE DRAWINGS

In the figures, identical reference numbers identify similar elements or acts. The sizes and relative positions of elements in the figures are not necessarily drawn to scale. For example, the shapes of various elements and angles are not drawn to scale and some of these elements are enlarged and positioned to improve FIGURE legibility. Further, the particular shapes of the elements as drawn, are not intended to convey any information regarding the actual shape of the particular elements, and have been solely selected for ease of recognition in the figures.

FIG. 1 shows Compound 2 having increased potency relative to Compound A.

DETAILED DESCRIPTION

The particulars described herein are by way of example and are only for purposes of illustrative discussion of embodiments of the present disclosure. The use of any and all examples, or exemplary language (e.g., "such as" or "for example") provided herein is merely intended to better illuminate the disclosure and does not pose a limitation on the scope of the disclosure as claimed. No language in the specification should be construed as indicating any non-claimed element is essential to the practice of the disclosure. Further, all methods described herein can be performed in any suitable order unless otherwise indicated herein or otherwise clearly contradicted by context.

Definitions used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of ordinary skill in the art.

The use of the alternative (e.g., "or") should be understood to mean one, both, or any combination thereof of the alternatives. The various embodiments described above can be combined to provide further embodiments. Groupings of alternative elements or embodiments of the disclosure described herein should not be construed as limitations. Each member of a group may be referred to and claimed individually, or in any combination with other members of the group or other elements found herein.

Each embodiment disclosed herein can comprise, consist essentially of, or consist of a particular stated element, step, ingredient, or component. As used herein, the term "comprise" or "comprises" means "includes, but is not limited to," and allows for the inclusion of unspecified elements, steps, ingredients, or components, even in major amounts. As used herein, the phrase "consisting of" excludes any element, step, ingredient, or component that is not specified. As used herein, the phrase "consisting essentially of" limits the scope of the embodiment to the specified elements, steps, ingredients, or components, and to those that do not materially affect the basic and novel characteristics of the claimed disclosure.

The terms "a," "an," "the," and similar articles or terms used in the context of describing the disclosure (especially in the context of the following claims) are to be construed to cover both the singular and the plural (i.e., "one or more"), unless otherwise indicated herein or clearly contradicted by context. Ranges of values recited herein are intended to serve as a shorthand method of referring individually to each separate value falling within the range. In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as size or thickness, are to be understood to include any integer within the recited range, unless otherwise indicated. Unless otherwise indicated herein, each individual value is incorporated into the specification as if it were individually recited herein.

The term "about" has the meaning reasonably ascribed to it by a person of ordinary skill in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or 1% of the stated value.

"Amino" refers to the —NH$_2$ group.

"Hydroxy" or "hydroxyl" refers to the —OH group.

"Alkyl" refers to a straight or branched hydrocarbon chain group consisting solely of carbon and hydrogen atoms, containing no unsaturation, having from one to eighteen carbon atoms ($C_1$-$C_{18}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Aminoalkyl" is an alkyl group comprising at least one amino substituent. The amino substituent may be on a primary, secondary or tertiary carbon. Unless stated otherwise specifically in the specification, aminoalkyl groups are optionally substituted.

"Hydroxyalkyl" or "hydroxylalkyl" refers to an alkyl group, as defined above, comprising at least one hydroxy substituent. The —OH substituent may be on a primary, secondary or tertiary carbon. Unless stated otherwise specifically in the specification, a hydroxyalkyl group is optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]$_x$-carbon bond, where x is 1, 2 or 3). In other embodiments, the heteroatom is at a terminus of the alkylene and thus serves to join the alkylene to the remainder of the molecule (e.g., M1-H$_a$-A-M2, where M1 and M2 are portions of the molecule, H$_a$ is a heteroatom and A is an alkylene). Unless stated otherwise specifically in the specification, a heteroalkylene group is optionally substituted.

"Protecting group" refers to a chemical used to protect a particular functional group during desired synthetic steps. Functional groups may include, e.g., hydroxy, amino, and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino (i.e., an "amine protecting group"), amidino and guanidino include an allyloxy carbonyl protecting group, a benzyloxycarbonyl protecting group, a butyloxycarbonyl protecting group (e.g., t-butoxycarbonyl or Boc), or a fluorenylmethyloxycarbonyl protecting group (or Fmoc) and the like. For example, A Boc protected amine or an Fmoc protected amine would have the following structures, respectively:

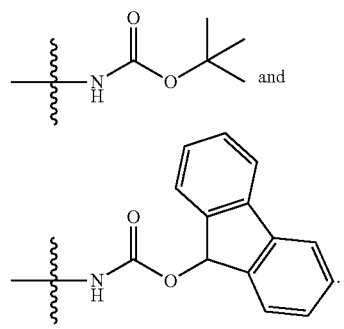

Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin. In some embodiments, protecting groups include, e.g., a triphenylmethyl protecting group, a dimethoxytriphenylmethyl protecting group, allyloxycarbonyl protecting group, a benzyloxycarbonyl protecting group, a butyloxycarbonyl protecting group, or a fluorenylmethyloxycarbonyl protecting group.

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

"Sarcosine" refers to N-methylglycine, which is an amino acid having the following structure:

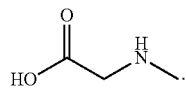

When sarcosine is included in an amino acid sequence, it may have one of the following structures:

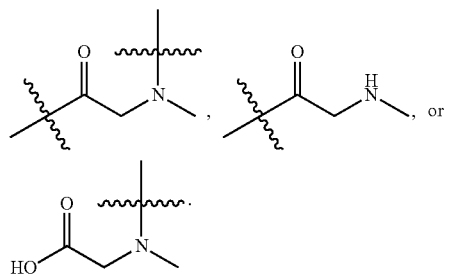

"Norleucine" (abbreviated Nle or N*) or 2-aminohexanoic acid is an amino acid compound that is a isomer of leucine and has the following structure:

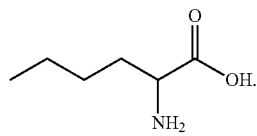

When norleucine is included in an amino acid sequence, it may have one of the following structures:

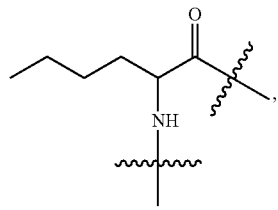

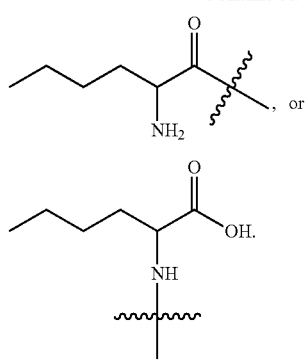

"Saccharide" refers to a group of compounds including sugars, starch, and cellulose, monosaccharides, disaccharides, oligosaccharides, and polysaccharides and can exist in ring or short chain conformation and generally have the molecular formula $C_m(H_2O)_n$ wherein m may be different than n (with some exceptions such as deoxyribose). Saccharides include, e.g., moieties having one of the following structures (and stereoisomers thereof):

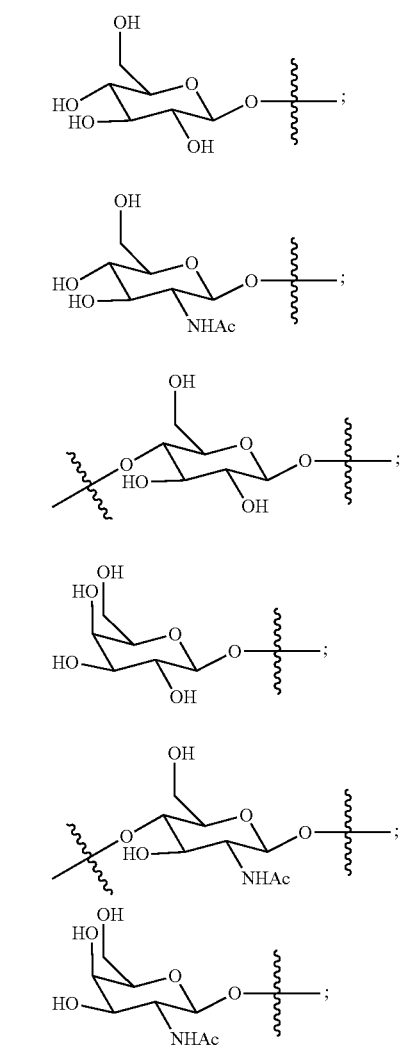

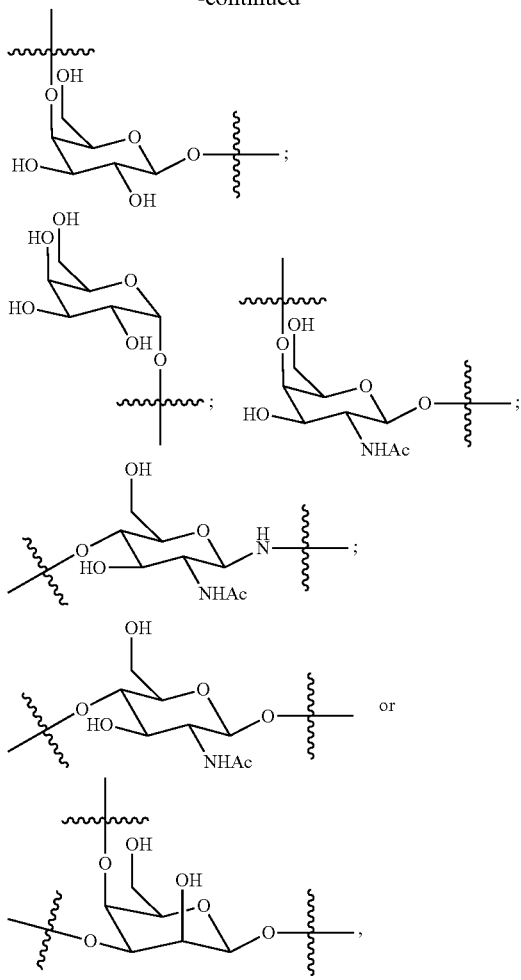

"Glycosidic bond" or "glycosidic linkage" refers to a type of covalent bond that joins a saccharide molecule or moiety to another group that may or may not be a saccharide.

The subjects that can be treated according to the methods of the current disclosure can be a human or non-human animal. For example, the subject can be a human, non-human primate, pig, dog, rodent, feline, bovine, or other mammal. As used herein, the terms "subject" and "patient" are used interchangeably. Likewise, the compounds and compositions can be administered to human cells or non-human animal cells in vitro or in vivo. In some embodiments, the cells are mammalian cells.

The pharmaceutically effective amount of the compound depends on the type of disease to be treated as well as the tolerance of the subject for the treatment.

The disease treatment according to the current disclosure can also be administered alone or in combination with one or more other treatments. For example, cancer in a subject can be treated by administering a compound or composition of the current disclosure in combination (simultaneously or consecutively) with chemotherapy and/or radiotherapy. For some diseases, treatment of the subject may include surgery. The compound or composition may be administered before or after surgery.

As used herein, the terms "treat" or "treatment" refer to both therapeutic treatment and prophylactic or preventative measures, wherein the object is to prevent or slow down (lessen) an undesired physiological change or disorder, such as the development or spread of an oncological disorder (e.g., cancer). In some embodiments, the subject has a cancer at the time of administration. In other embodiments, the subject does not have a cancer at the time of administration, in which case the compound or composition may be administered to prevent or delay onset of the cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. In some embodiments, the treatment methods include identifying the subject as having cancer or another disease or disorder to be treated.

The amount of the compound (e.g., a compound of Formula (I)) or composition administered to the subject or cell may be an effective amount, e.g., a therapeutically effective amount. As used herein, the term "(therapeutically) effective amount" refers to an amount of an agent (e.g., a compound or composition of the disclosure) effective to treat a disease or disorder in a subject. In the case of cancer, the therapeutically effective amount of the agent may directly or indirectly (e.g., through an immune response) reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

While the compounds (e.g., compounds of Formula (I)) can be administered as isolated compounds, these compounds can also be administered as part of a pharmaceutical composition. The subject disclosure provides compositions comprising one or more compounds of the current disclosure in association with at least one pharmaceutically acceptable carrier. Compounds and compositions containing them can be administered to a subject locally at or adjacent to a site of intended action (e.g., a tumor or lesion), or systemically (e.g., intravascularly). The compound and pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art. Optionally, the suitable bioactive agents that are optionally administered with the compounds separately or within the same formulation can be formulated as pharmaceutically acceptable salts or solvates.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids can also be made.

A "linker" refers to a contiguous chain of at least one atom, such as carbon, oxygen, nitrogen, sulfur, phosphorous and combinations thereof, which connects a portion of a molecule (e.g., a cyclic β-hairpin peptidomimetic) to a different molecule or molecules, moiety or moieties, or a solid support (e.g., amino acid residues or derivatives thereof). Linkers may connect the different agents, moieties or molecules via a covalent bond or other means, such as ionic or hydrogen bond interactions. Linkers can be branched to connect one molecule to a plurality of different molecules.

An "amino acid" or "amino acid residue" refers to an α-amino acid residue (—CO—CHR—NH—), where R is a side chain. Amino acids are denoted with a 3-letter or 1-letter code according to the table below:

| Amino Acid | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "naturally occurring amino acid" refers to an amino acid present in proteins found in nature. Examples of naturally occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

As used herein, the term "anti-cancer agent" refers to a substance or treatment that inhibits the function of cancer cells, inhibits their formation, and/or causes their destruction in vitro or in vivo. Examples include, but are not limited to, cytotoxic agents (e.g., 5-fluorouracil, TAXOL) and anti-signaling agents (e.g., the PI3K inhibitor LY).

A. Compounds

In one embodiment the disclosure relates to a compound comprising a cyclic β-hairpin peptidomimetic, an optional linker and optionally one or more amino acid residues or derivatives thereof. Accordingly, some embodiments provide a compound having a structure of Formula (I):

$$X\text{-}L^1\text{-}N(R^1)R^2,\quad (I)$$

or a pharmaceutically acceptable salt, tautomer, or stereoisomer thereof, wherein:

X is a cyclic β-hairpin peptidomimetic;

L is an optional linker;

$R^1$ is H; and $R^2$ is H or a moiety comprising one or more amino acid residues or substituted derivatives thereof.

In some embodiments, $L^1$ is absent. In certain embodiments, $L^1$ is a heteroalkylene linker. For example, in some embodiments, the heteroalkylene linker comprises from 2 to 6 carbons and a heteroatom selected from O, S, N and P. In some embodiments, $L^1$ is optionally substituted.

In some more specific embodiments, $L^1$ is —S(O)$_t$—(CH$_2$)$_n$—, wherein:

t is 0, 1 or 2; and n is 1, 2, 3, 4, 5 or 6.

In some embodiments, t is 2. In some embodiments, t is 1. In some embodiments, t is 0. In certain embodiments, n is 3, 4, 5 or 6. In more specific embodiments, n is 3. In certain specific embodiments, $L^1$ has the following structure:

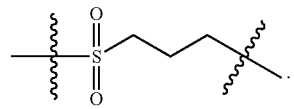 [SMILES: *CCCS(*)(=O)=O]

In some embodiments of the foregoing, $R^2$ is H. In certain related embodiments, $R^2$ comprises one or more amino acid residues or substituted derivatives thereof. In more specific embodiments, $R^2$ comprises one or more cysteine residues or derivatives thereof. In some embodiments, $R^2$ comprises one or two cysteine residues or derivatives thereof.

In other embodiments, $R^2$ has one of the following structures:

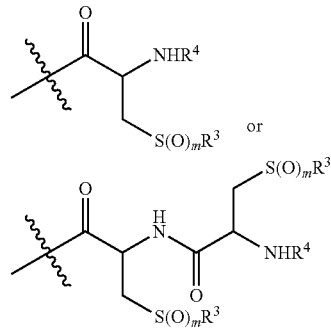

wherein:

$R^3$ is, at each occurrence, independently H, a protecting group, alkyl, aminoalkyl, a protected aminoalkyl, hydroxyalkyl, a protected hydroxyalkyl, or -$L^2$-Y;

$R^4$ is H or an amine protecting group;

m is, at each occurrence, independently, 0, 1 or 2;

$L^2$ is a linker; and

Y at each occurrence independently comprises one or more saccharide moieties.

In some embodiments, $R^2$ has one of the following structures:

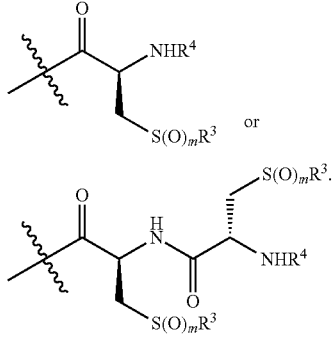

In some specific embodiments, $R^2$ has one of the following structures:

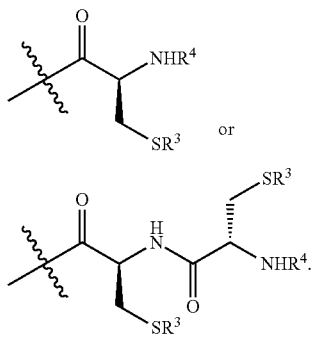

In certain specific embodiments, $R^2$ has one of the following structures:

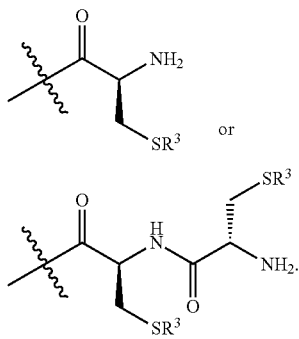

In certain specific embodiments, $R^2$ has one of the following structures:

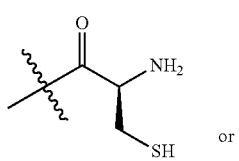

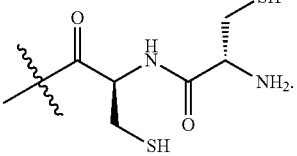

In some embodiments, at least one occurrence of $R^3$ is H. In some related embodiments, $R^3$ is H at each occurrence.

In other embodiments, at least one occurrence of $R^3$ is a protecting group. In some embodiments, $R^3$ is a protecting group at each occurrence. For example, in some embodiments, the protecting group is a triphenylmethyl protecting group or a dimethoxytriphenylmethyl protecting group.

In other embodiments, at least one occurrence of $R^3$ is a protected aminoalkyl or a protected hydroxyalkyl. In more specific embodiments, $R^3$ is a protected aminoalkyl or a protected hydroxyalkyl at each occurrence. For example, in some embodiments, the protected aminoalkyl or protected hydroxyalkyl comprises an allyloxy carbonyl protecting group, a benzyloxy carbonyl protecting group, a butyloxy carbonyl protecting group, or a fluorenylmethyloxy carbonyl protecting group.

In some of the foregoing embodiments, at least one occurrence of $R^3$ is $C_1$-$C_{18}$ alkyl, $C_1$-$C_{18}$ aminoalkyl, a protected $C_1$-$C_{18}$ aminoalkyl, a protected $C_1$-$C_{18}$ hydroxyalkyl or $C_1$-$C_{18}$ hydroxyalkyl. In more specific embodiments, $R^3$ is $C_1$-$C_{18}$ alkyl, $C_1$-$C_{18}$ aminoalkyl, a protected $C_1$-$C_{18}$ aminoalkyl, a protected $C_1$-$C_{18}$ hydroxyalkyl or $C_1$-$C_{18}$ hydroxyalkyl at each occurrence.

In some of the foregoing embodiments, at least one occurrence of $R^3$ is $C_1$-$C_{12}$ alkyl, $C_1$-$C_{12}$ aminoalkyl, a protected $C_1$-$C_{12}$ aminoalkyl, a protected $C_1$-$C_{12}$ hydroxyalkyl or $C_1$-$C_{12}$ hydroxyalkyl. In more specific embodiments, $R^3$ is $C_1$-$C_{12}$ alkyl, $C_1$-$C_{12}$ aminoalkyl, a protected $C_1$-$C_{12}$ aminoalkyl, a protected $C_1$-$C_{12}$ hydroxyalkyl or $C_1$-$C_{12}$ hydroxyalkyl at each occurrence.

In some of the foregoing embodiments, at least one occurrence of $R^3$ is $C_1$-$C_8$ alkyl, $C_1$-$C_8$ aminoalkyl, a protected $C_1$-$C_8$ aminoalkyl, a protected $C_1$-$C_8$ hydroxyalkyl or $C_1$-$C_8$ hydroxyalkyl. In more specific embodiments, $R^3$ is $C_1$-$C_8$ alkyl, $C_1$-$C_8$ aminoalkyl, a protected $C_1$-$C_8$ aminoalkyl, a protected $C_1$-$C_8$ hydroxyalkyl or $C_1$-$C_8$ hydroxyalkyl at each occurrence.

In some embodiments, at least one occurrence of $R^3$ is -$L^2$-Y. In more specific embodiments, $R^3$ is -$L^2$-Y at each occurrence. In certain specific embodiments, $L^2$ has the following structure:

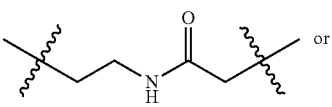

wherein:
$L^3$ is a direct bond or —NH—; and
p is 0, 1 or 2.

For example, in certain embodiments, $L^2$ has one of the following structures:

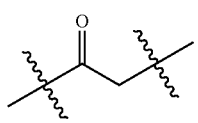

In certain related embodiments, Y comprises one of the following saccharide moieties:

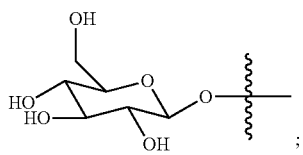
;

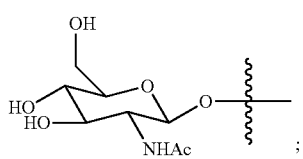
;

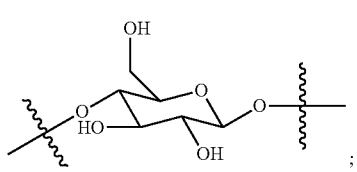
;

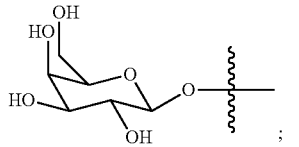
;

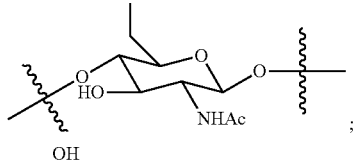
;

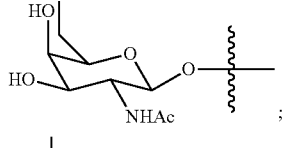
;

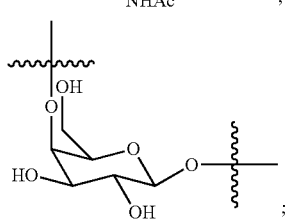
;

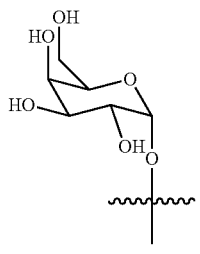
;

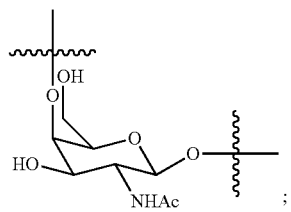
;

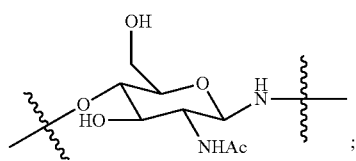
;

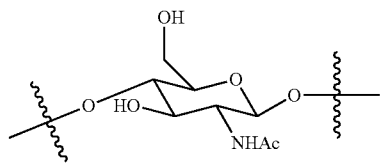
or

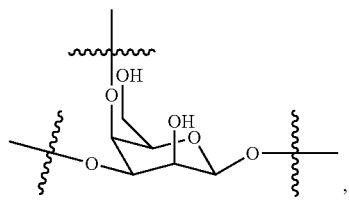
, wherein:

∿ at each occurrence independently indicates a linkage to $L^2$, a bond to a H, or a glycosidic link to a saccharide moiety optionally substituted with one or more additional saccharide moieties, provided that at least one ∿ is a linkage to $L^2$.

In more specific embodiments, Y comprises one of the following saccharide moieties:

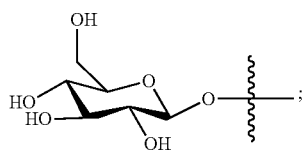
;

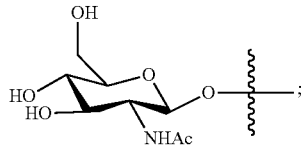
;

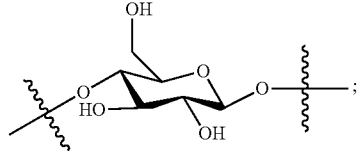
;

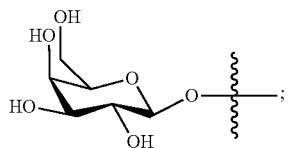
;

-continued

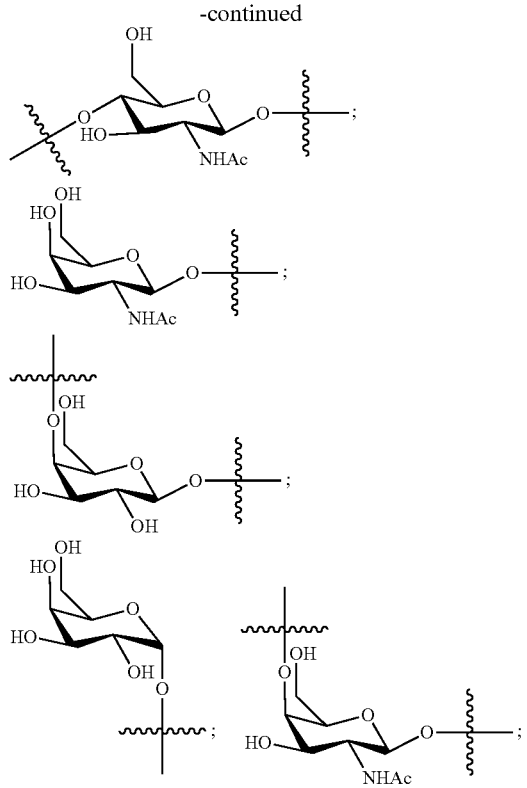

-continued

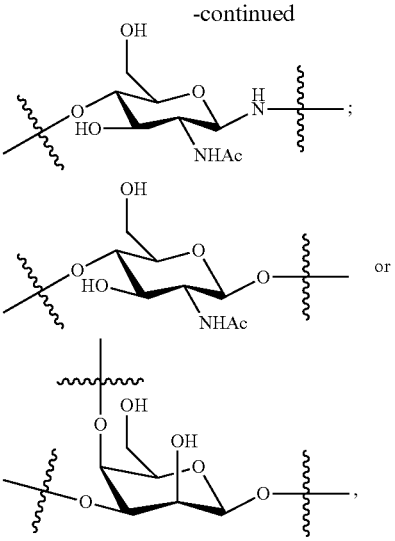

wherein:

∿ at each occurrence independently indicates a linkage to $L^2$, a bond to a H, or a glycosidic link to a saccharide moiety optionally substituted with one or more additional saccharide moieties, provided that at least one ∿ is a linkage to $L^2$. For example, in some embodiments, Y comprises 1, 2, 3, 4, 5, 6, 7, 8, or 9 saccharide moieties.

In more specific embodiments of the foregoing, -$L^2$-Y has one of the following structures:

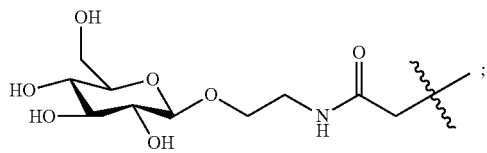
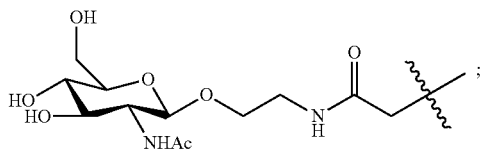

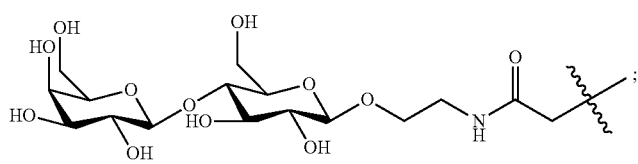

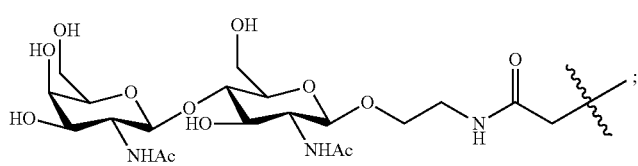

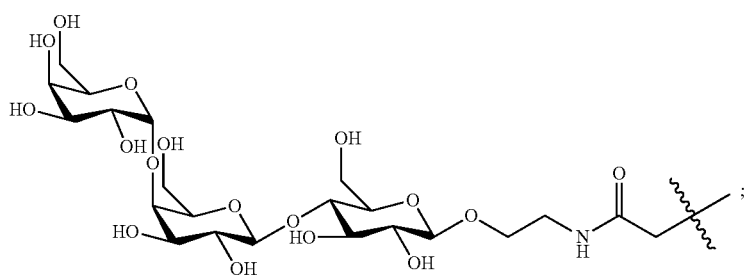

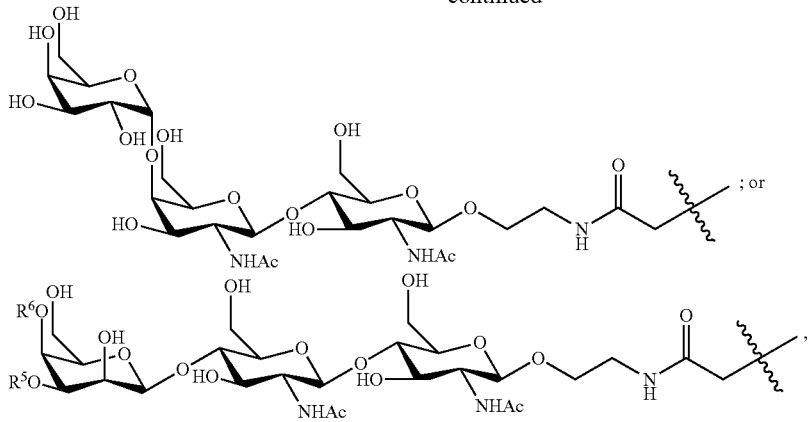

wherein:

$R^5$ and $R^6$ are, at each occurrence, independently H, or a glycosidic link to a saccharide moiety optionally substituted with one or more additional saccharide moieties.

In some embodiments, $R^4$ is an amine protecting group. For example, in some embodiments, $R^4$ is a butyloxycarbonyl protecting group, or a fluorenylmethyloxycarbonyl protecting group. In other embodiments, $R^4$ is H.

In some embodiments, m is 0. In other embodiments, m is 1. In still other embodiments, m is 2.

In some embodiments, the cyclic β-hairpin peptidomimetic comprises a recognition sequence and a non-recognition sequence and the recognition sequence is linked to the non-recognition sequence by a first linker and a second linker. In some more specific embodiment, the non-recognition sequence is 5 amino acids selected from KLKLK (SEQ ID NO:27), KLQLK (SEQ ID NO:28), QLKLK (SEQ ID NO:29), KLKLQ (SEQ ID NO:281), KQKLK (SEQ ID NO:30), KLKQK (SEQ ID NO:282), KXKXK (SEQ ID NO:31), or ELKLK (SEQ ID NO:32), wherein X is sarcosine.

In certain embodiments, the recognition sequence is five amino acids selected from MVVSW (SEQ ID NO:33), MVVSA (SEQ ID NO:34), MVVAW (SEQ ID NO:35), MVASW (SEQ ID NO:36), MAVSW (SEQ ID NO:37), AVVSW (SEQ ID NO:38), N*VVSW (SEQ ID NO:39), N*VVYW (SEQ ID NO:40), N*VVAW (SEQ ID NO:41), AVVAW (SEQ ID NO:42), N*AVAW (SEQ ID NO:43), N*VAAW (SEQ ID NO:44), N*VLAW (SEQ ID NO:45), N*VIAW (SEQ ID NO:46), N*VFAW (SEQ ID NO:47), or WSVVW (SEQ ID NO:48), WAVAW (SEQ ID NO:50), WAVAA (SEQ ID NO:51), WAVAM (SEQ ID NO:52), WAVAN* (SEQ ID NO:53), WAVVN* (SEQ ID NO:54), WAVSN* (SEQ ID NO:55), WAAAW (SEQ ID NO:56), WAAAA (SEQ ID NO:57), WAAAM (SEQ ID NO:58), WAAAN* (SEQ ID NO:59), WAAVW (SEQ ID NO:60), WAAVA (SEQ ID NO:61), WAAVM (SEQ ID NO:62), WAAVN* (SEQ ID NO:63), WAASN* (SEQ ID NO:64), WVVAW (SEQ ID NO:65), WVVAA (SEQ ID NO:66), WVVAM (SEQ ID NO:67), WVVAN* (SEQ ID NO:68), WVVVW (SEQ ID NO:69), WVVVA (SEQ ID NO:70), WVVVM (SEQ ID NO:71), WVVVN* (SEQ ID NO: 72), WVVSN* (SEQ ID NO:73), WVAAN* (SEQ ID NO:74), WVAVW (SEQ ID NO:75), WVAVA (SEQ ID NO:76), WVAVM (SEQ ID NO:77), WVAVN* (SEQ ID NO:78), WVASN* (SEQ ID NO:79), WSVAW (SEQ ID NO:80), WSVAA (SEQ ID NO:81), WSVAM (SEQ ID NO:82), WSVAN* (SEQ ID NO:83), WSVVW (SEQ ID NO:48), WSVVA (SEQ ID NO:84), WSVVM (SEQ ID NO:85), WSVVN* (SEQ ID NO:86), WSVSW (SEQ ID NO:87), WSVSA (SEQ ID NO:88), WSVSM (SEQ ID NO:89), WSVSN* (SEQ ID NO:90), WSAAW (SEQ ID NO:91), WSAAA (SEQ ID NO:92), WSAAM (SEQ ID NO:93), WSAAN* (SEQ ID NO:94), WSAVW (SEQ ID NO:95), WSAVA (SEQ ID NO:96), WSAVM (SEQ ID NO:97), WSAVN* (SEQ ID NO:98), WSASW (SEQ ID NO:99), WSASA (SEQ ID NO:100), WSASM (SEQ ID NO:101), WSASN* (SEQ ID NO:102), WYVAW (SEQ ID NO:103), WYVAA (SEQ ID NO:104), WYVAM (SEQ ID NO:105), WYVAN* (SEQ ID NO: 106), WYVVW (SEQ ID NO:107), WYVVA (SEQ ID NO:108), WYVVM (SEQ ID NO:109), WYVVN* (SEQ ID NO: 110), WYVSW (SEQ ID NO:111), WYVSA (SEQ ID NO:112), WYVSM (SEQ ID NO:113), WYVSN* (SEQ ID NO:114), WYAAW (SEQ ID NO:115), WYAAA (SEQ ID NO:116), WYAAM (SEQ ID NO:117), WYAAN* (SEQ ID NO:118), WYAAW (SEQ ID NO:119), WYAVA (SEQ ID NO:120), WYAVM (SEQ ID NO:121), WYAVN* (SEQ ID NO:122), WYASW (SEQ ID NO:123), WYASA (SEQ ID NO:124), WYASM (SEQ ID NO:125), WYASN* (SEQ ID NO:126), AAVAA (SEQ ID NO:127), AAVAM (SEQ ID NO:128), AAVAN* (SEQ ID NO:129), AAVVN* (SEQ ID NO:130), AAVAN* (SEQ ID NO:131), AAAAA (SEQ ID NO:132), AAAAM (SEQ ID NO:133), AAAAN* (SEQ ID NO:134), AAAVW (SEQ ID NO:135), AAAVA (SEQ ID NO:136), AAAVM (SEQ ID NO:137), AAAVN* (SEQ ID NO:138), AAASM (SEQ ID NO:139), AAASN* (SEQ ID NO: 140), AVVAW (SEQ ID NO:141), AVVAA (SEQ ID NO:142), AVVAM (SEQ ID NO:143), AVVAN* (SEQ ID NO:144), AVVVA (SEQ ID NO:145), AVVVM (SEQ ID NO:146), AVVVN* (SEQ ID NO:147), AVVSN* (SEQ ID NO:148), AVAAW (SEQ ID NO:42), AVAAM (SEQ ID NO:149), AVAAN* (SEQ ID NO:150), AVAVA (SEQ ID NO:151), AVAVM (SEQ ID NO:152), AVAVN* (SEQ ID NO:153), AVASN* (SEQ ID NO:154), ASVAW (SEQ ID NO:155), ASVAA (SEQ ID NO:156), ASVAM (SEQ ID NO:157), ASVAN* (SEQ ID NO:158), ASVVW (SEQ ID NO:159), ASVVA (SEQ ID NO:160), ASVVM (SEQ ID NO:161), ASVVN* (SEQ ID NO:162), ASVSA (SEQ ID NO:163), ASVSM (SEQ ID NO:164), ASVSN* (SEQ ID NO:165), ASAAW (SEQ ID NO:166), ASAAA (SEQ ID NO:167), ASAAM (SEQ ID NO:168), ASAAN* (SEQ ID NO:169), ASAVW (SEQ ID NO:170), ASAVA (SEQ ID NO:171), ASAVM (SEQ ID NO:172), ASAVN* (SEQ ID NO:173), ASASA (SEQ ID NO:174), ASASM (SEQ ID NO:175), ASASN* (SEQ ID NO:176), AYVAW (SEQ ID NO:177), AYVAA (SEQ ID NO:178), AYVAM (SEQ ID NO:179), AYVAN* (SEQ ID NO: 180), AYVVW (SEQ ID NO:181), AYVVA (SEQ ID NO:182), AYVVM (SEQ ID NO: 183), AYVVN* (SEQ ID NO:184), AYVSW (SEQ ID NO:185), AYVSA (SEQ ID NO:186), AYVSM (SEQ ID NO:187), AYVSN* (SEQ ID NO:188), AYAAW (SEQ ID NO:189), AYAAA (SEQ ID NO:190), AYAAM (SEQ ID NO:191), AYAAN* (SEQ ID NO:192), AYAVW (SEQ ID NO:193), AYAVA (SEQ ID NO:194), AYAVM (SEQ ID NO:195), AYAVN* (SEQ ID NO:196), AYASW (SEQ ID NO:197), AYASA (SEQ ID NO:198), AYASM (SEQ ID NO:199), AYASN* (SEQ ID NO:200), MAVAA (SEQ ID NO:201), MAVAM (SEQ ID NO:202), MAVAN* (SEQ ID NO:203), MAVVN* (SEQ ID NO:204), MAVSN* (SEQ ID NO:205), MAAAA (SEQ ID NO:206), MAAAM (SEQ ID NO:207), MAAAN* (SEQ ID NO:208), MAAVW (SEQ ID NO:209), MAAVA (SEQ ID NO:210), MAAVM (SEQ ID NO:211), MAAVN* (SEQ ID NO:212), MAASN* (SEQ ID NO:213), MVVAW (SEQ ID NO:214), MVVAA (SEQ ID NO:215), MVVAM (SEQ ID NO:216), MVVAN* (SEQ ID NO:217), MVVVM (SEQ ID NO:218), MVVVN* (SEQ ID NO:219), MVVSN* (SEQ ID NO:220), MVAAM (SEQ ID NO:221), MVAAN* (SEQ ID NO:222), MVAVM (SEQ ID NO:223), MVAVN* (SEQ ID NO:224), MVASN* (SEQ ID NO:225), MSVAW (SEQ ID NO:226), MSVAA (SEQ ID NO:227), MSVAM (SEQ ID NO:228), MSVAN* (SEQ ID NO:229), MSVVW (SEQ ID NO:230), MSVVA (SEQ ID NO:231), MSVVM (SEQ ID NO:232), MSVVN* (SEQ ID NO:233), MSVSM (SEQ ID NO:234), MSVSN* (SEQ ID NO:235), MSAAW (SEQ ID NO:236), MSAAA (SEQ ID NO:237), MSAAM (SEQ ID NO:238), MSAAN* (SEQ ID NO:239), MSAVW (SEQ ID NO:240), MSAVA (SEQ ID NO:241), MSAVM (SEQ ID NO:242), MSAVN* (SEQ ID NO:243), MSASM (SEQ ID NO:244), MSASN* (SEQ ID NO:245), MYVAW (SEQ ID NO:246), MYVAA (SEQ ID NO:247), MYVAM (SEQ ID NO:248), MYVAN* (SEQ ID NO:249), MYVVW (SEQ ID NO:250), MYVVA (SEQ ID NO:251), MYVVM (SEQ ID NO:252), MYVVN* (SEQ ID NO:253), MYVSW (SEQ ID NO:254), MYVSA (SEQ ID NO:255), MYVSM (SEQ ID NO:256), MYVSN* (SEQ ID NO:257), MYAAW (SEQ ID NO:258), MYAAA (SEQ ID NO:259), MYAAM (SEQ ID NO:260), MYAAN* (SEQ ID NO:261), MYAVW (SEQ ID NO:262), MYAVA (SEQ ID NO:263), MYAVM (SEQ ID NO:264), MYAVN* (SEQ ID NO:265), MYASW (SEQ ID NO:266), MYASA (SEQ ID NO:267), MYASM (SEQ ID NO:268), or MYASN* (SEQ ID NO:269), wherein N* is norleucine.

In some more specific embodiments, the recognition sequence is five amino acids selected from MVVSW (SEQ ID NO:33), MVVSA (SEQ ID NO:34), MVVAW (SEQ ID NO:35), MVASW (SEQ ID NO:36), MAVSW (SEQ ID NO:37), AVVSW (SEQ ID NO:38), N*VVSW (SEQ ID NO:39), N*VVYW (SEQ ID NO:40), N*VVAW (SEQ ID NO:41), AVVAW (SEQ ID NO:42), N*AVAW (SEQ ID NO:43), N*VAAW (SEQ ID NO:44), N*VLAW (SEQ ID NO:45), N*VIAW (SEQ ID NO:46), N*VFAW (SEQ ID NO:47), or WSVVW (SEQ ID NO:48), wherein N* is norleucine.

In some embodiments, the non-recognition sequence is KLKLK (SEQ ID NO:27). In some specific embodiments, the recognition sequence is N*VVAW (SEQ ID NO:41), wherein N* is norleucine. In certain embodiments, the non-recognition sequence is KLKLK (SEQ ID NO:27) and the recognition sequence is N*VVAW (SEQ ID NO:41), wherein N* is norleucine. The sequence identification numbers (i.e., SEQ ID Nos) are as set forth in Table 1 below.

TABLE 1

Sequence identification numbers

| Sequence Identification Number (SEQ ID NO) | Amino Acid Sequence (with 1-letter codes)[†,‡] |
|---|---|
| SEQ ID NO: 27 | KLKLK |
| SEQ ID NO: 28 | KLQLK |
| SEQ ID NO: 29 | QLKLK |
| SEQ ID NO: 30 | KQKLK |
| SEQ ID NO: 31 | KXKXK |
| SEQ ID NO: 32 | ELKLK |
| SEQ ID NO: 33 | MVVSW |
| SEQ ID NO: 34 | MVVSA |
| SEQ ID NO: 35 | MVVAW |
| SEQ ID NO: 36 | MVASW |
| SEQ ID NO: 37 | MAVSW |
| SEQ ID NO: 38 | AVVSW |
| SEQ ID NO: 39 | N*VVSW |
| SEQ ID NO: 40 | N*VVYW |
| SEQ ID NO: 41 | N*VVAW |
| SEQ ID NO: 42 | AVVAW |
| SEQ ID NO: 43 | N*AVAW |
| SEQ ID NO: 44 | N*VAAW |
| SEQ ID NO: 45 | N*VLAW |
| SEQ ID NO: 46 | N*VIAW |
| SEQ ID NO: 47 | N*VFAW |
| SEQ ID NO: 48 | WSVVW |
| SEQ ID NO: 50 | WAVAW |
| SEQ ID NO: 51 | WAVAA |
| SEQ ID NO: 52 | WAVAM |
| SEQ ID NO: 53 | WAVAN* |
| SEQ ID NO: 54 | WAVVN* |
| SEQ ID NO: 55 | WAVSN* |
| SEQ ID NO: 56 | WAAAW |
| SEQ ID NO: 57 | WAAAA |
| SEQ ID NO: 58 | WAAAM |
| SEQ ID NO: 59 | WAAAN* |
| SEQ ID NO: 60 | WAAVW |
| SEQ ID NO: 61 | WAAVA |
| SEQ ID NO: 62 | WAAVM |
| SEQ ID NO: 63 | WAAVN* |
| SEQ ID NO: 64 | WAASN* |

TABLE 1-continued

Sequence identification numbers

| Sequence Identification Number (SEQ ID NO) | Amino Acid Sequence (with 1-letter codes)†,‡ |
|---|---|
| SEQ ID NO: 65 | WVVAW |
| SEQ ID NO: 66 | WVVAA |
| SEQ ID NO: 67 | WVVAM |
| SEQ ID NO: 68 | WVVAN* |
| SEQ ID NO: 69 | WVVVW |
| SEQ ID NO: 70 | WVVVA |
| SEQ ID NO: 71 | WVVVM |
| SEQ ID NO: 72 | WVVVN* |
| SEQ ID NO: 73 | WVVSN* |
| SEQ ID NO: 74 | WVAAN* |
| SEQ ID NO: 75 | WVAVW |
| SEQ ID NO: 76 | WVAVA |
| SEQ ID NO: 77 | WVAVM |
| SEQ ID NO: 78 | WVAVN* |
| SEQ ID NO: 79 | WVASN* |
| SEQ ID NO: 80 | WSVAW |
| SEQ ID NO: 81 | WSVAA |
| SEQ ID NO: 82 | WSVAM |
| SEQ ID NO: 83 | WSVAN* |
| SEQ ID NO: 84 | WSVVA |
| SEQ ID NO: 85 | WSVVM |
| SEQ ID NO: 86 | WSVVN* |
| SEQ ID NO: 87 | WSVSW |
| SEQ ID NO: 88 | WSVSA |
| SEQ ID NO: 89 | WSVSM |
| SEQ ID NO: 90 | WSVSN* |
| SEQ ID NO: 91 | WSAAW |
| SEQ ID NO: 92 | WSAAA |
| SEQ ID NO: 93 | WSAAM |
| SEQ ID NO: 94 | WSAAN* |
| SEQ ID NO: 95 | WSAVW |
| SEQ ID NO: 96 | WSAVA |
| SEQ ID NO: 97 | WSAVM |
| SEQ ID NO: 98 | WSAVN* |
| SEQ ID NO: 99 | WSASW |
| SEQ ID NO: 100 | WSASA |
| SEQ ID NO: 101 | WSASM |
| SEQ ID NO: 102 | WSASN* |
| SEQ ID NO: 103 | WYVAW |
| SEQ ID NO: 104 | WYVAA |
| SEQ ID NO: 105 | WYVAM |
| SEQ ID NO: 106 | WYVAN* |
| SEQ ID NO: 107 | WYVVW |
| SEQ ID NO: 108 | WYVVA |
| SEQ ID NO: 109 | WYVVM |
| SEQ ID NO: 110 | WYVVN* |
| SEQ ID NO: 111 | WYVSW |
| SEQ ID NO: 112 | WYVSA |
| SEQ ID NO: 113 | WYVSM |
| SEQ ID NO: 114 | WYVSN* |
| SEQ ID NO: 115 | WYAAW |
| SEQ ID NO: 116 | WYAAA |
| SEQ ID NO: 117 | WYAAM |
| SEQ ID NO: 118 | WYAAN* |
| SEQ ID NO: 119 | WYAAW |
| SEQ ID NO: 120 | WYAVA |
| SEQ ID NO: 121 | WYAVM |
| SEQ ID NO: 122 | WYAVN* |
| SEQ ID NO: 123 | WYASW |
| SEQ ID NO: 124 | WYASA |
| SEQ ID NO: 125 | WYASM |
| SEQ ID NO: 126 | WYASN* |
| SEQ ID NO: 127 | AAVAA |
| SEQ ID NO: 128 | AAVAM |
| SEQ ID NO: 129 | AAVAN* |
| SEQ ID NO: 130 | AAVVN* |
| SEQ ID NO: 131 | AAVAN* |
| SEQ ID NO: 132 | AAAAA |
| SEQ ID NO: 133 | AAAAM |
| SEQ ID NO: 134 | AAAAN* |
| SEQ ID NO: 135 | AAAVW |
| SEQ ID NO: 136 | AAAVA |
| SEQ ID NO: 137 | AAAVM |

TABLE 1-continued

Sequence identification numbers

| Sequence Identification Number (SEQ ID NO) | Amino Acid Sequence (with 1-letter codes)†,‡ |
|---|---|
| SEQ ID NO: 138 | AAAVN* |
| SEQ ID NO: 139 | AAASM |
| SEQ ID NO: 140 | AAASN* |
| SEQ ID NO: 141 | AVVAW |
| SEQ ID NO: 142 | AVVAA |
| SEQ ID NO: 143 | AVVAM |
| SEQ ID NO: 144 | AVVAN* |
| SEQ ID NO: 145 | AVVVA |
| SEQ ID NO: 146 | AVVVM |
| SEQ ID NO: 147 | AVVVN* |
| SEQ ID NO: 148 | AVVSN* |
| SEQ ID NO: 149 | AVAAM |
| SEQ ID NO: 150 | AVAAN* |
| SEQ ID NO: 151 | AVAVA |
| SEQ ID NO: 152 | AVAVM |
| SEQ ID NO: 153 | AVAVN* |
| SEQ ID NO: 154 | AVASN* |
| SEQ ID NO: 155 | ASVAW |
| SEQ ID NO: 156 | ASVAA |
| SEQ ID NO: 157 | ASVAM |
| SEQ ID NO: 158 | ASVAN* |
| SEQ ID NO: 159 | ASVVW |
| SEQ ID NO: 160 | ASVVA |
| SEQ ID NO: 161 | ASVVM |
| SEQ ID NO: 162 | ASVVN* |
| SEQ ID NO: 163 | ASVSA |
| SEQ ID NO: 164 | ASVSM |
| SEQ ID NO: 165 | ASVSN* |
| SEQ ID NO: 166 | ASAAW |
| SEQ ID NO: 167 | ASAAA |
| SEQ ID NO: 168 | ASAAM |
| SEQ ID NO: 169 | ASAAN* |
| SEQ ID NO: 170 | ASAVW |
| SEQ ID NO: 171 | ASAVA |
| SEQ ID NO: 172 | ASAVM |
| SEQ ID NO: 173 | ASAVN* |
| SEQ ID NO: 174 | ASASA |
| SEQ ID NO: 175 | ASASM |
| SEQ ID NO: 176 | ASASN* |
| SEQ ID NO: 177 | AYVAW |
| SEQ ID NO: 178 | AYVAA |
| SEQ ID NO: 179 | AYVAM |
| SEQ ID NO: 180 | AYVAN* |
| SEQ ID NO: 181 | AYVVW |
| SEQ ID NO: 182 | AYVVA |
| SEQ ID NO: 183 | AYVVM |
| SEQ ID NO: 184 | AYVVN* |
| SEQ ID NO: 185 | AYVSW |
| SEQ ID NO: 186 | AYVSA |
| SEQ ID NO: 187 | AYVSM |
| SEQ ID NO: 188 | AYVSN* |
| SEQ ID NO: 189 | AYAAW |
| SEQ ID NO: 190 | AYAAA |
| SEQ ID NO: 191 | AYAAM |
| SEQ ID NO: 192 | AYAAN* |
| SEQ ID NO: 193 | AYAVW |
| SEQ ID NO: 194 | AYAVA |
| SEQ ID NO: 195 | AYAVM |
| SEQ ID NO: 196 | AYAVN* |
| SEQ ID NO: 197 | AYASW |
| SEQ ID NO: 198 | AYASA |
| SEQ ID NO: 199 | AYASM |
| SEQ ID NO: 200 | AYASN* |
| SEQ ID NO: 201 | MAVAA |
| SEQ ID NO: 202 | MAVAM |
| SEQ ID NO: 203 | MAVAN* |
| SEQ ID NO: 204 | MAVVN* |
| SEQ ID NO: 205 | MAVSN* |
| SEQ ID NO: 206 | MAAAA |
| SEQ ID NO: 207 | MAAAM |
| SEQ ID NO: 208 | MAAAN* |
| SEQ ID NO: 209 | MAAVW |
| SEQ ID NO: 210 | MAAVA |

TABLE 1-continued

Sequence identification numbers

| Sequence Identification Number (SEQ ID NO) | Amino Acid Sequence (with 1-letter codes)†,‡ |
|---|---|
| SEQ ID NO: 211 | MAAVM |
| SEQ ID NO: 212 | MAAVN* |
| SEQ ID NO: 213 | MAASN* |
| SEQ ID NO: 214 | MVVAW |
| SEQ ID NO: 215 | MVVAA |
| SEQ ID NO: 216 | MVVAM |
| SEQ ID NO: 217 | MVVAN* |
| SEQ ID NO: 218 | MVVVM |
| SEQ ID NO: 219 | MVVVN* |
| SEQ ID NO: 220 | MVVSN* |
| SEQ ID NO: 221 | MVAAM |
| SEQ ID NO: 222 | MVAAN* |
| SEQ ID NO: 223 | MVAVM |
| SEQ ID NO: 224 | MVAVN* |
| SEQ ID NO: 225 | MVASN* |
| SEQ ID NO: 226 | MSVAW |
| SEQ ID NO: 227 | MSVAA |
| SEQ ID NO: 228 | MSVAM |
| SEQ ID NO: 229 | MSVAN* |
| SEQ ID NO: 230 | MSVVW |
| SEQ ID NO: 231 | MSVVA |
| SEQ ID NO: 232 | MSVVM |
| SEQ ID NO: 233 | MSVVN* |
| SEQ ID NO: 234 | MSVSM |
| SEQ ID NO: 235 | MSVSN* |
| SEQ ID NO: 236 | MSAAW |
| SEQ ID NO: 237 | MSAAA |
| SEQ ID NO: 238 | MSAAM |
| SEQ ID NO: 239 | MSAAN* |
| SEQ ID NO: 240 | MSAVW |
| SEQ ID NO: 241 | MSAVA |
| SEQ ID NO: 242 | MSAVM |
| SEQ ID NO: 243 | MSAVN* |
| SEQ ID NO: 244 | MSASM |
| SEQ ID NO: 245 | MSASN* |
| SEQ ID NO: 246 | MYVAW |
| SEQ ID NO: 247 | MYVAA |
| SEQ ID NO: 248 | MYVAM |
| SEQ ID NO: 249 | MYVAN* |
| SEQ ID NO: 250 | MYVVW |
| SEQ ID NO: 251 | MYVVA |
| SEQ ID NO: 252 | MYVVM |
| SEQ ID NO: 253 | MYVVN* |
| SEQ ID NO: 254 | MYVSW |
| SEQ ID NO: 255 | MYVSA |
| SEQ ID NO: 256 | MYVSM |
| SEQ ID NO: 257 | MYVSN* |
| SEQ ID NO: 258 | MYAAW |
| SEQ ID NO: 259 | MYAAA |
| SEQ ID NO: 260 | MYAAM |
| SEQ ID NO: 261 | MYAAN* |
| SEQ ID NO: 262 | MYAVW |
| SEQ ID NO: 263 | MYAVA |
| SEQ ID NO: 264 | MYAVM |
| SEQ ID NO: 265 | MYAVN* |
| SEQ ID NO: 266 | MYASW |
| SEQ ID NO: 267 | MYASA |
| SEQ ID NO: 268 | MYASM |
| SEQ ID NO: 269 | MYASN* |
| SEQ ID NO: 281 | KLKLQ |
| SEQ ID NO: 282 | KLKQK |

†X is sarcosine
‡N* is norleucine

In certain embodiments related to the foregoing embodiments, the first linker and the second linker are independently selected from the structures (A), (B), (C) and (D):

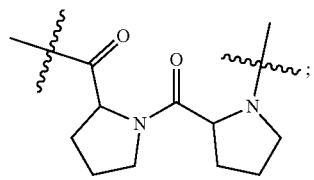

(A)

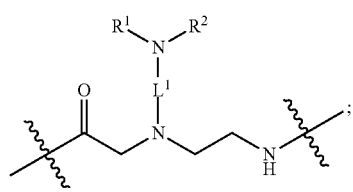

(B)

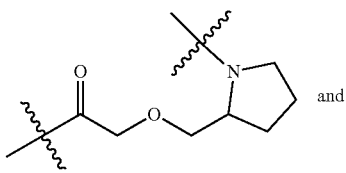

(C)

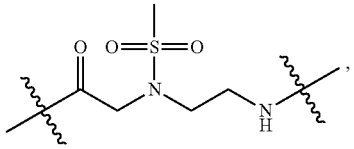

(D)

wherein:
at least one of the first and second linker is structure (B).

In other specific embodiments, the first linker is structure (B) and the second linker is structure (C). In some embodiments, the first linker is structure (B) and the second linker is structure (D).

In some embodiments, the compound has the following structure (Ia):

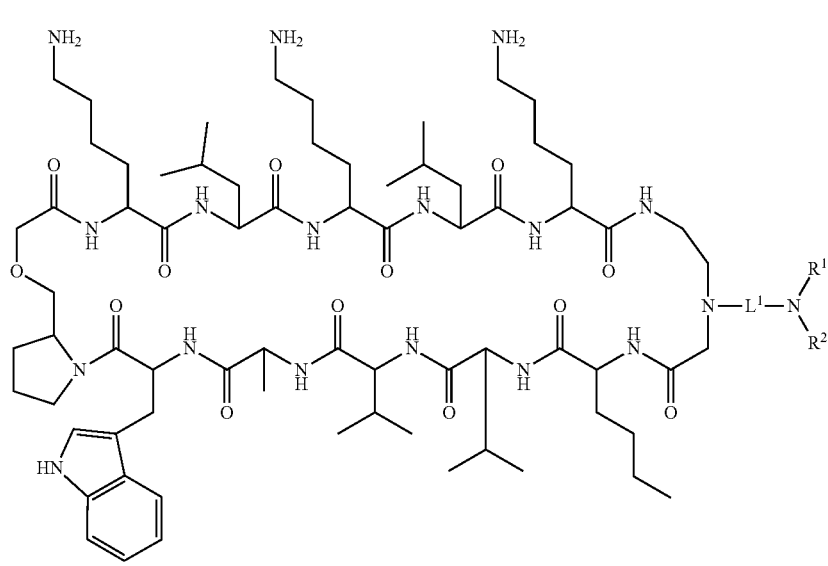

(Ia)

or a pharmaceutically acceptable salt, tautomer, or stereoisomer thereof.

In more specific embodiments, the compound has the following structure (Ib):
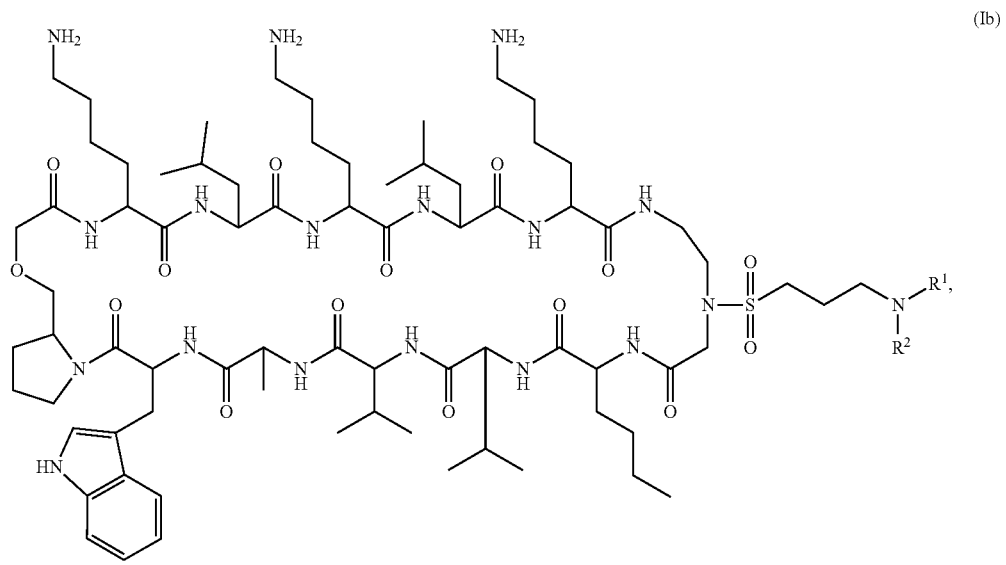
or a pharmaceutically acceptable salt, tautomer, or stereoisomer thereof.
In other more specific embodiments, the compound has the following structure:
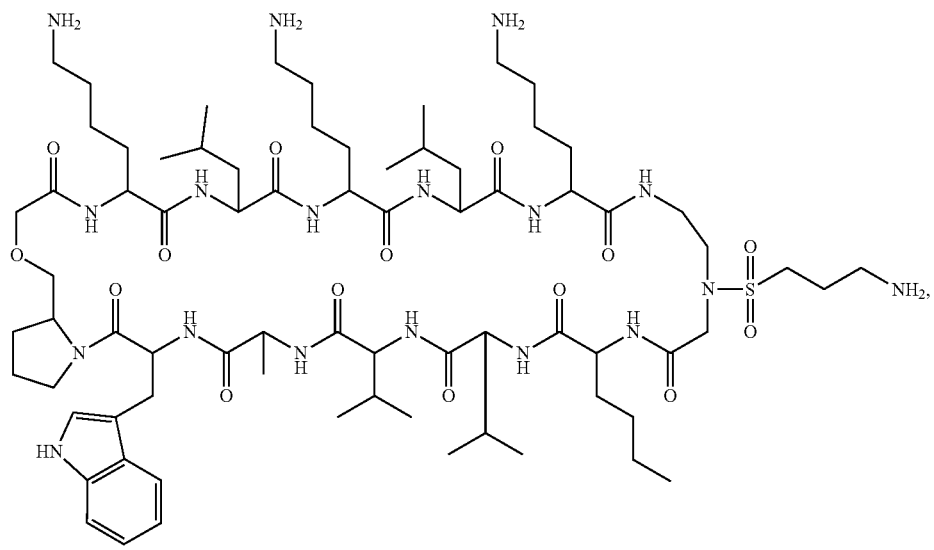 [SMILES: CCCCC1NC(=O)CN(S(=O)(=O)CCCN)CCNC(=O)C(CCCCN)NC(=O)C(CC(C)C)NC(=O)C(CCCCN)NC(=O)C(CC(C)C)NC(=O)C(CCCCN)NC(=O)COCC2CCCN2C(=O)C(Cc2c[nH]c3ccccc23)NC(=O)C(C)NC(=O)C(C(C)C)NC(=O)C(C(C)C)NC1=O]
or a pharmaceutically acceptable salt, tautomer, or stereoisomer thereof.

In some embodiments, the compound has the following structure:
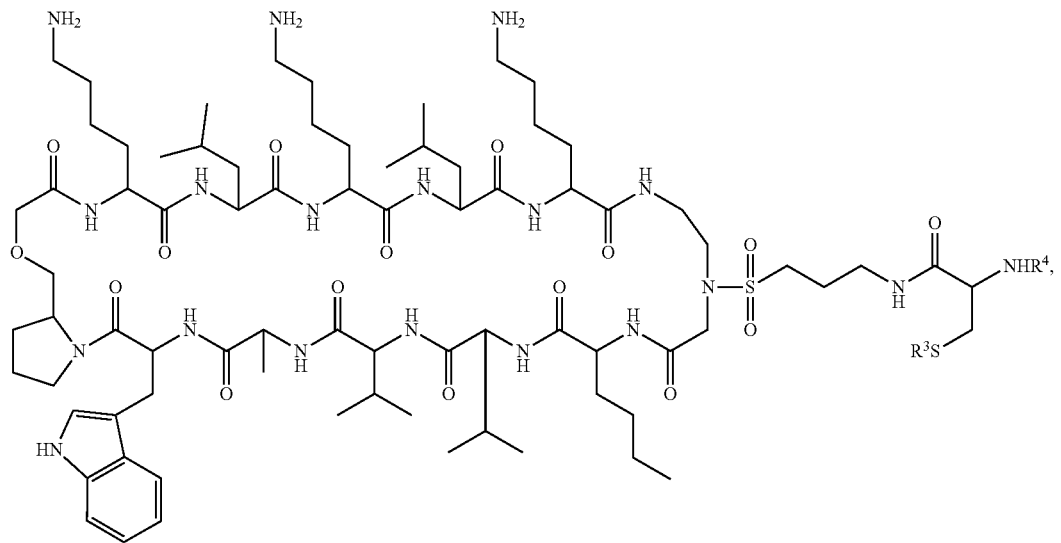
or a pharmaceutically acceptable salt, tautomer, or stereoisomer thereof.
In more specific embodiments, the compound has the following structure:
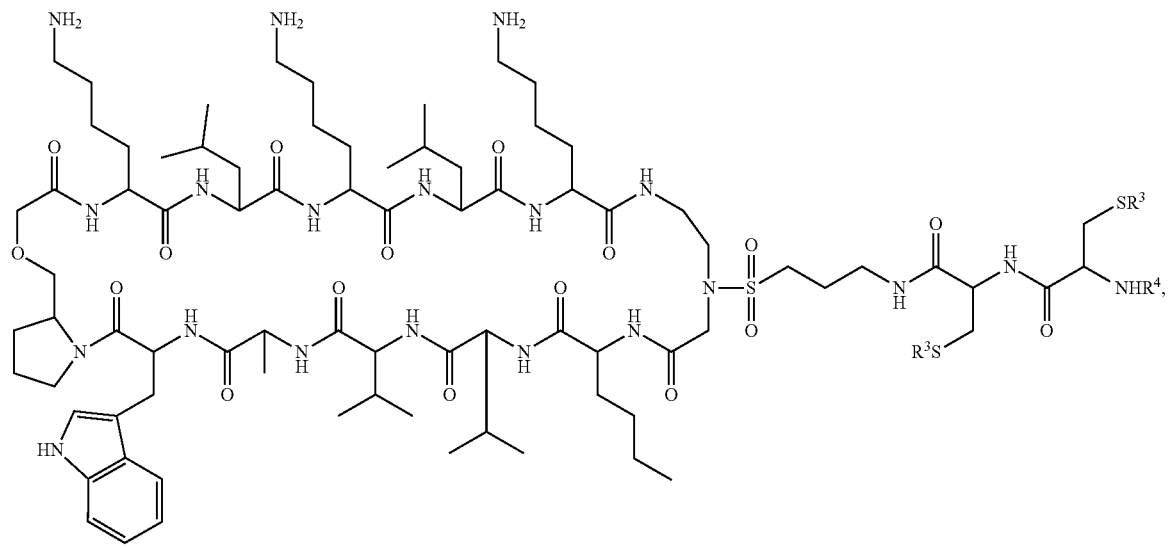
or a pharmaceutically acceptable salt, tautomer, or stereoisomer thereof.

In other embodiments, the compound has the following structure:
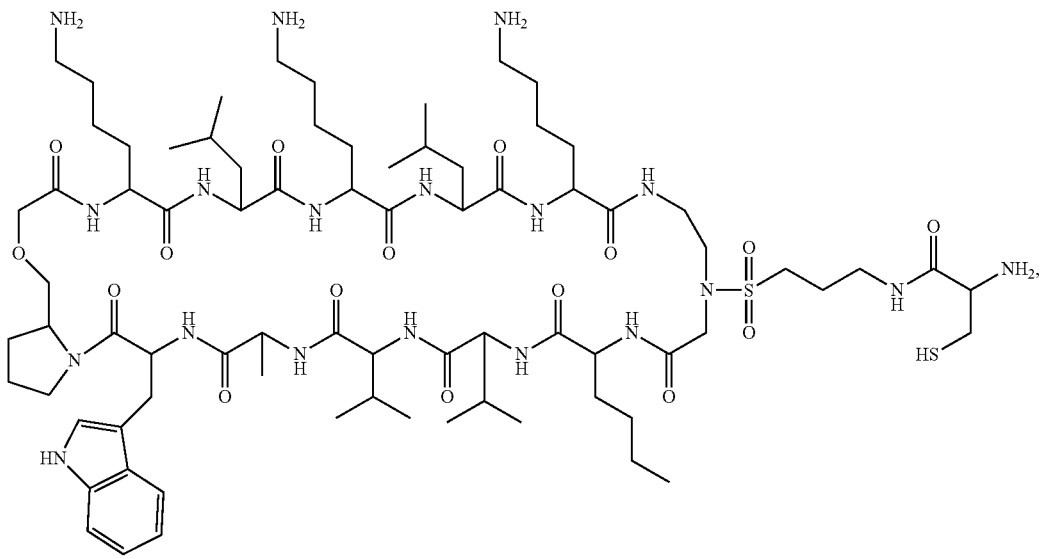 [SMILES: CCCCC1NC(=O)CN(S(=O)(=O)CCCNC(=O)C(N)CS)CCNC(=O)C(CCCCN)NC(=O)C(CC(C)C)NC(=O)C(CCCCN)NC(=O)C(CC(C)C)NC(=O)C(CCCCN)NC(=O)COCC2CCCN2C(=O)C(Cc2c[nH]c3ccccc23)NC(=O)C(C)NC(=O)C(C(C)C)NC(=O)C(C(C)C)NC1=O]
or a pharmaceutically acceptable salt, tautomer, or stereoisomer thereof.
In certain embodiments, the compound has the following structure:
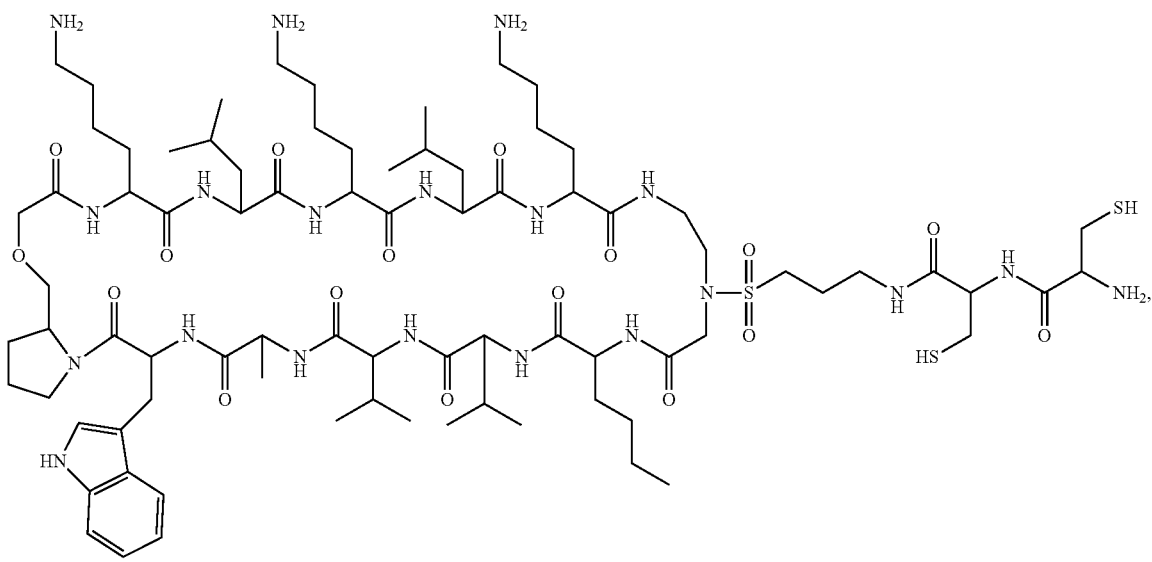 [SMILES: CCCCC1NC(=O)CN(S(=O)(=O)CCCNC(=O)C(CS)NC(=O)C(N)CS)CCNC(=O)C(CCCCN)NC(=O)C(CC(C)C)NC(=O)C(CCCCN)NC(=O)C(CC(C)C)NC(=O)C(CCCCN)NC(=O)COCC2CCCN2C(=O)C(Cc2c[nH]c3ccccc23)NC(=O)C(C)NC(=O)C(C(C)C)NC(=O)C(C(C)C)NC1=O]
or a pharmaceutically acceptable salt, tautomer, or stereoisomer thereof.

In other more specific embodiments, the compound has the following structure ("Compound 1"):
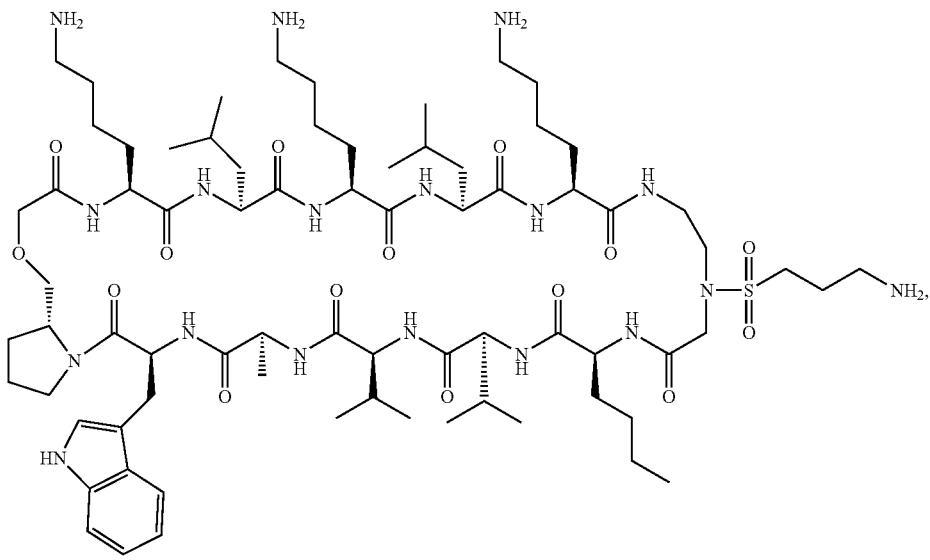 [SMILES: CCCC[C@@H]1NC(=O)CN(S(=O)(=O)CCCN)CCNC(=O)[C@H](CCCCN)NC(=O)[C@H](CC(C)C)NC(=O)[C@H](CCCCN)NC(=O)[C@H](CC(C)C)NC(=O)[C@H](CCCCN)NC(=O)COC[C@H]2CCCN2C(=O)[C@H](Cc2c[nH]c3ccccc23)NC(=O)[C@H](C)NC(=O)[C@H](C(C)C)NC(=O)[C@H](C(C)C)NC1=O]
or a pharmaceutically acceptable salt or tautomer thereof.
In some embodiments, the compound has the following structure ("Compound 2"):
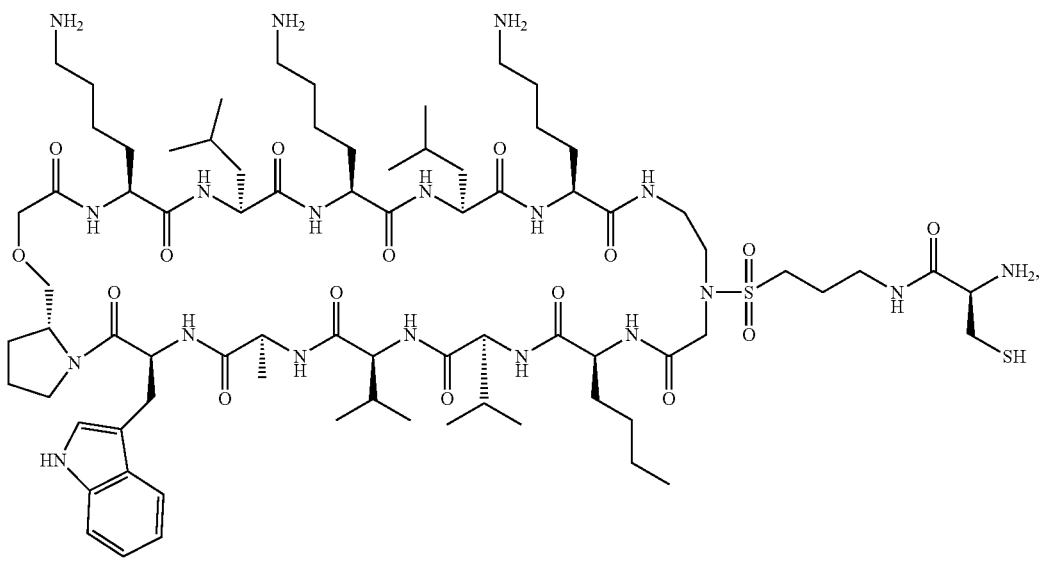 [SMILES: CCCC[C@@H]1NC(=O)CN(S(=O)(=O)CCCNC(=O)[C@@H](N)CS)CCNC(=O)[C@H](CCCCN)NC(=O)[C@H](CC(C)C)NC(=O)[C@H](CCCCN)NC(=O)[C@H](CC(C)C)NC(=O)[C@H](CCCCN)NC(=O)COC[C@H]2CCCN2C(=O)[C@H](Cc2c[nH]c3ccccc23)NC(=O)[C@H](C)NC(=O)[C@H](C(C)C)NC(=O)[C@H](C(C)C)NC1=O]
or a pharmaceutically acceptable salt or tautomer thereof.

In certain embodiments, the compound has the following structure ("Compound 3"):
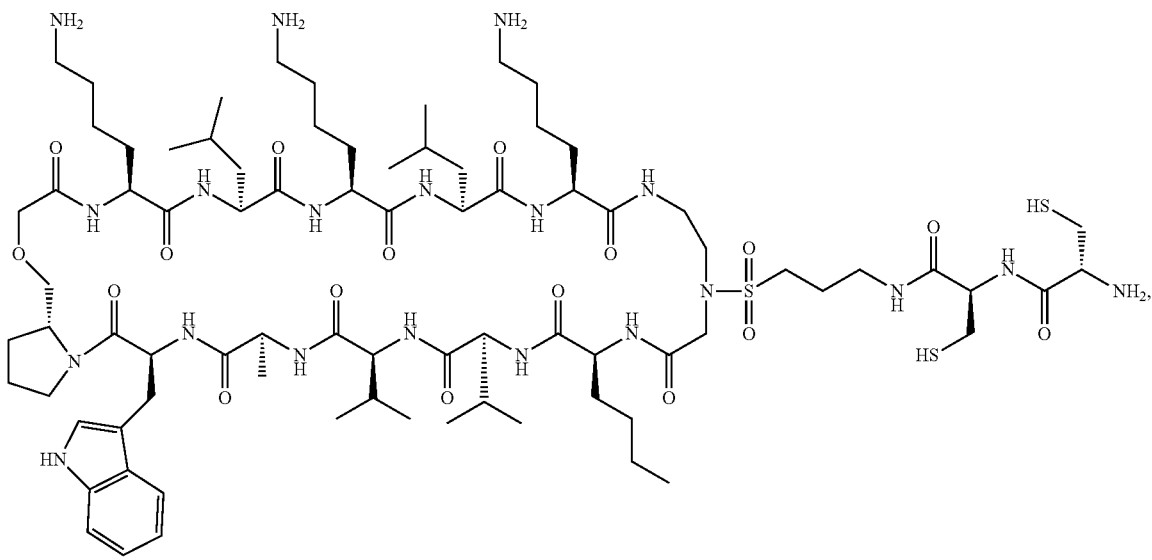 [SMILES: CCCC[C@@H]1NC(=O)CN(S(=O)(=O)CCCNC(=O)[C@H](CS)NC(=O)[C@@H](N)CS)CCNC(=O)[C@H](CCCCN)NC(=O)[C@H](CC(C)C)NC(=O)[C@H](CCCCN)NC(=O)[C@H](CC(C)C)NC(=O)[C@H](CCCCN)NC(=O)COC[C@H]2CCCN2C(=O)[C@H](Cc2c[nH]c3ccccc23)NC(=O)[C@H](C)NC(=O)[C@H](C(C)C)NC(=O)[C@H](C(C)C)NC1=O]
or a pharmaceutically acceptable salt or tautomer thereof.
In some embodiments, a compound is selected from a compound in Table 2, below.
TABLE 2
Exemplary compounds of structure of Formula (I)
| No. | Structure* |
|---|---|
| II-1 | 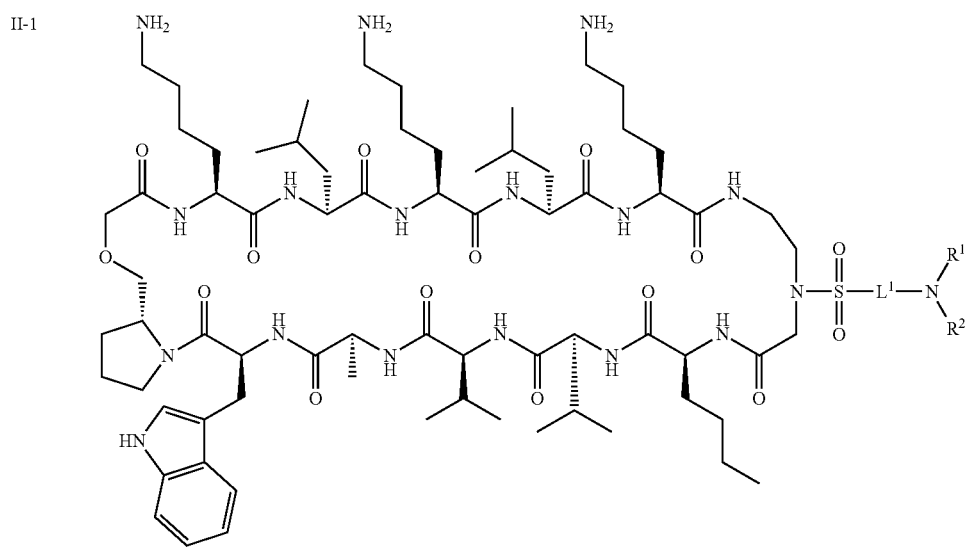 |

TABLE 2-continued

Exemplary compounds of structure of Formula (I)

| No. | Structure* |
|---|---|
| II-2 | 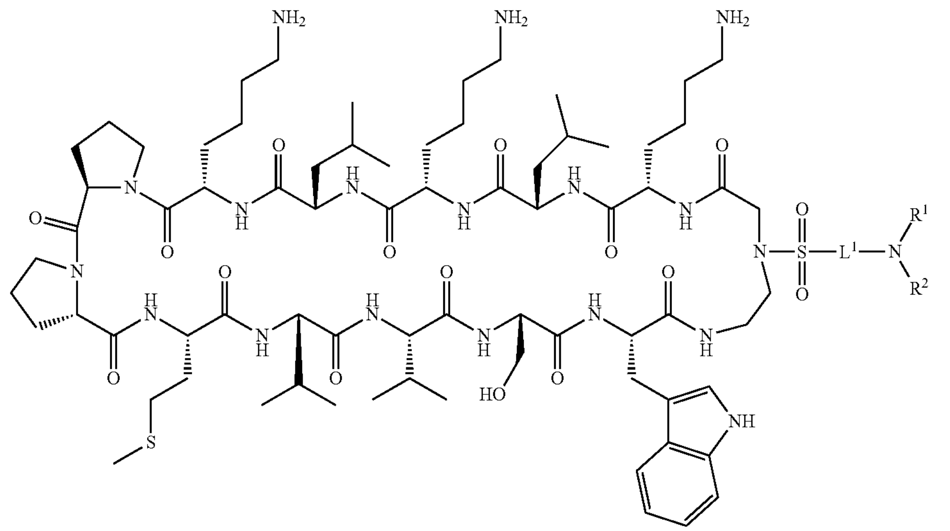 |
| II-3 | 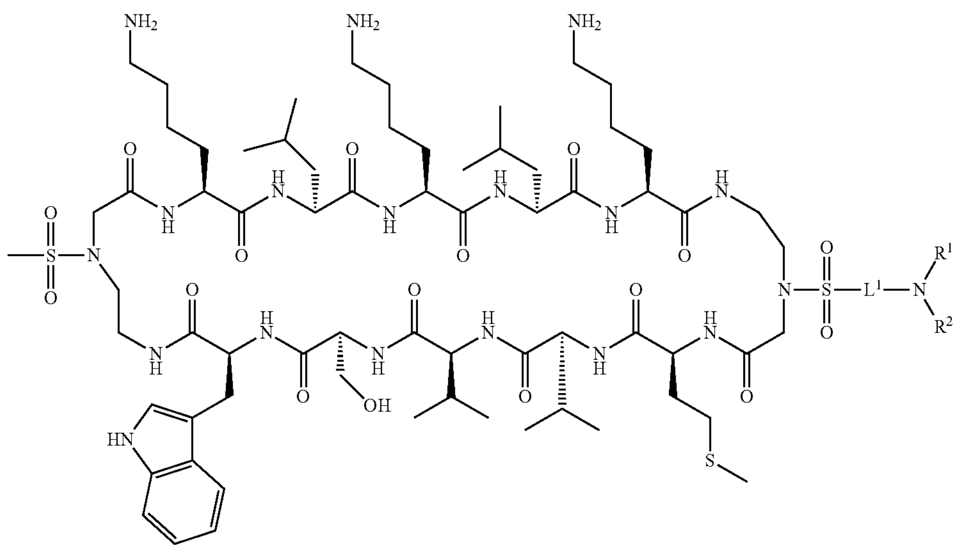 |
| II-4 | 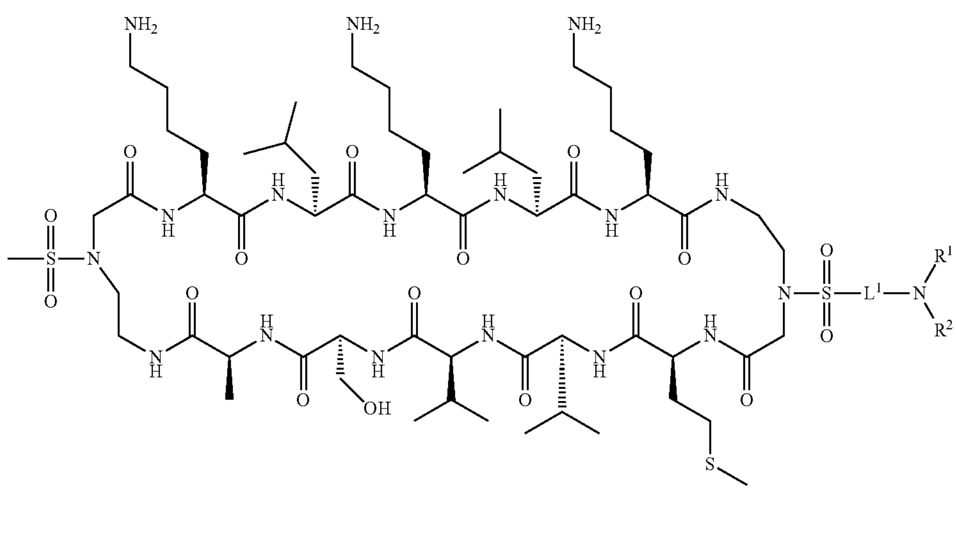 |

TABLE 2-continued

Exemplary compounds of structure of Formula (I)

| No. | Structure* |
|---|---|
| II-5 | 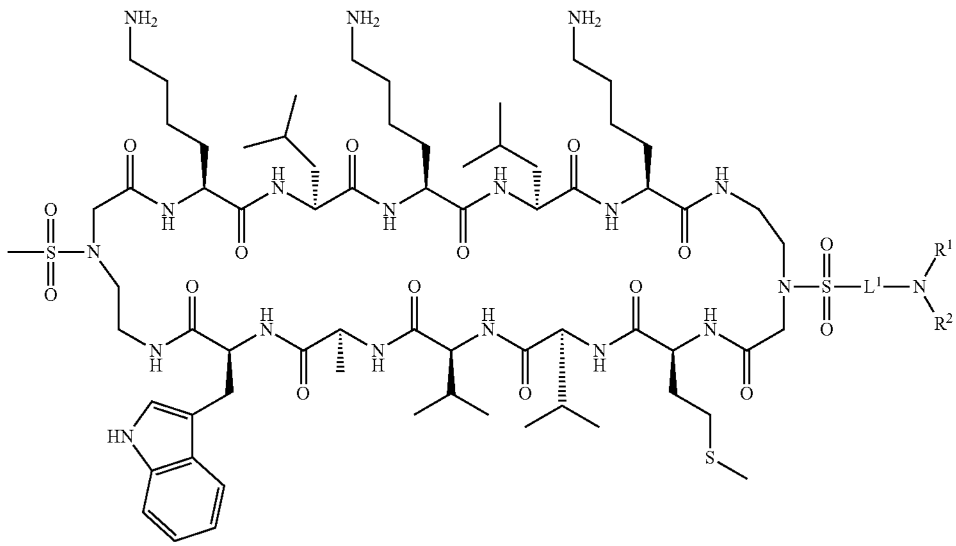 |
| II-6 | 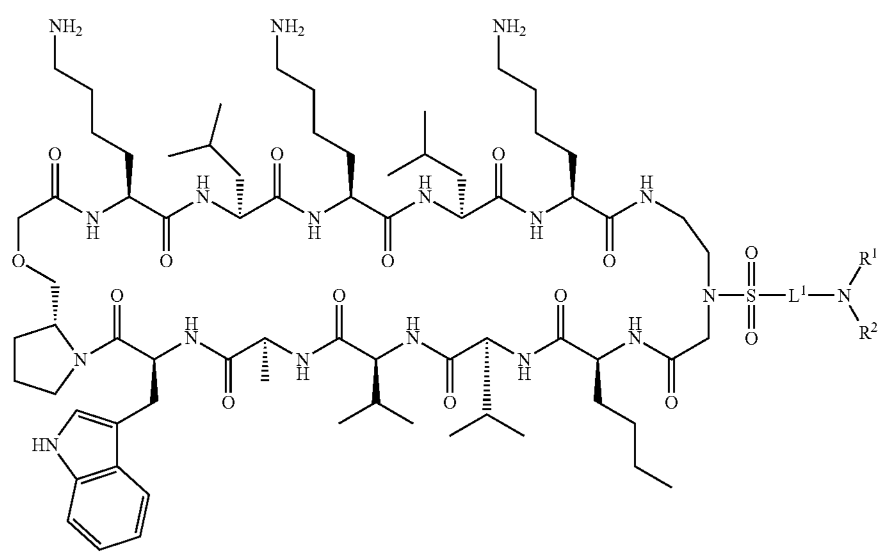 |

TABLE 2-continued
Exemplary compounds of structure of Formula (I)
| No. | Structure* |
|---|---|
| II-7 | 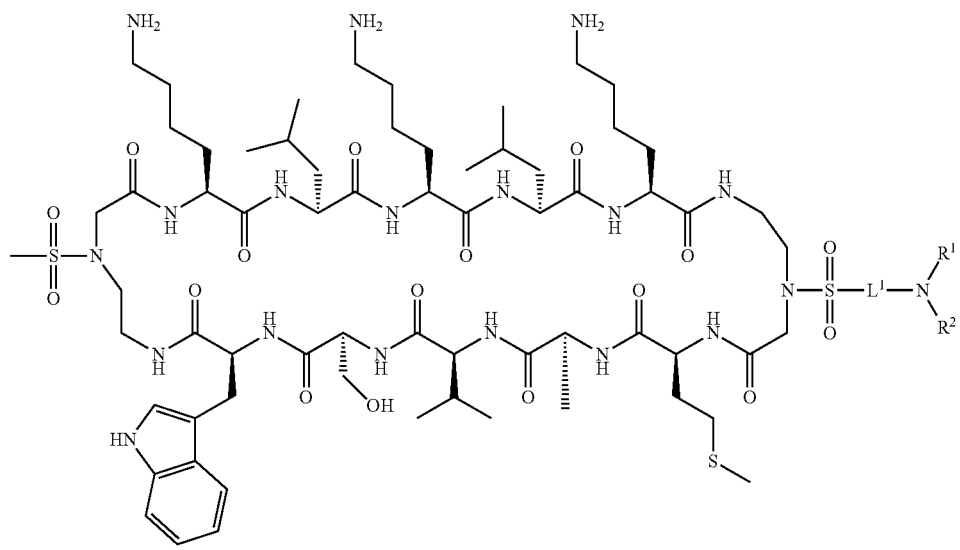 |
| II-8 | 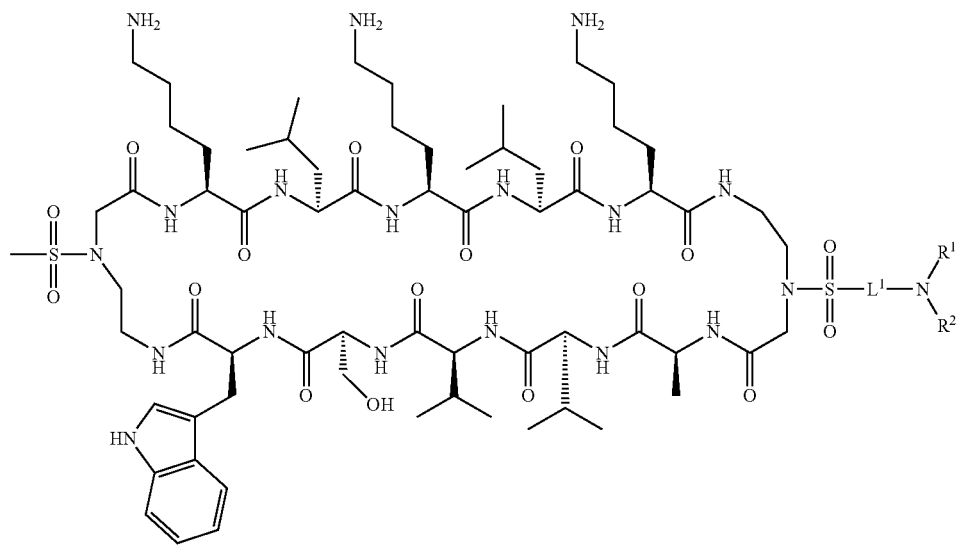 |

TABLE 2-continued

Exemplary compounds of structure of Formula (I)

| No. | Structure* |
|---|---|
| II-9 | 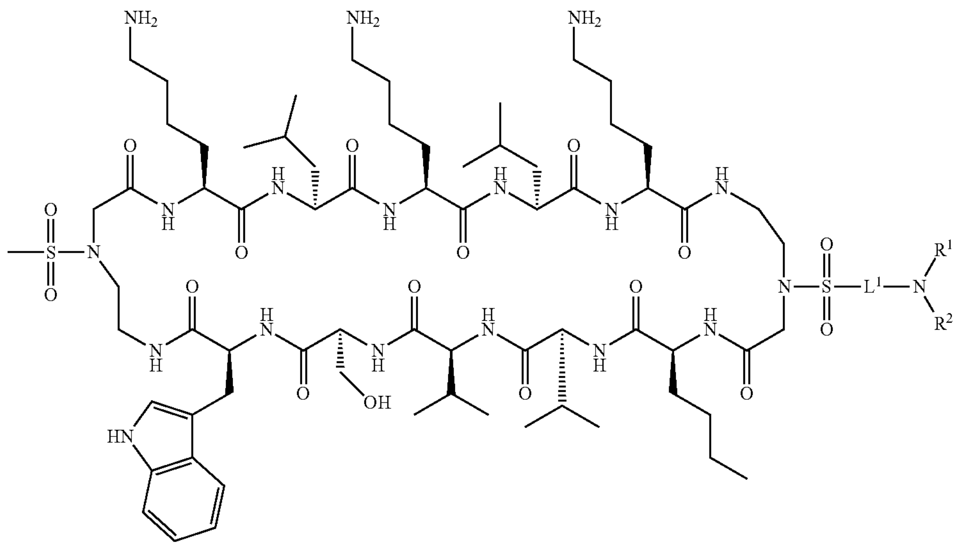 |
| II-10 | 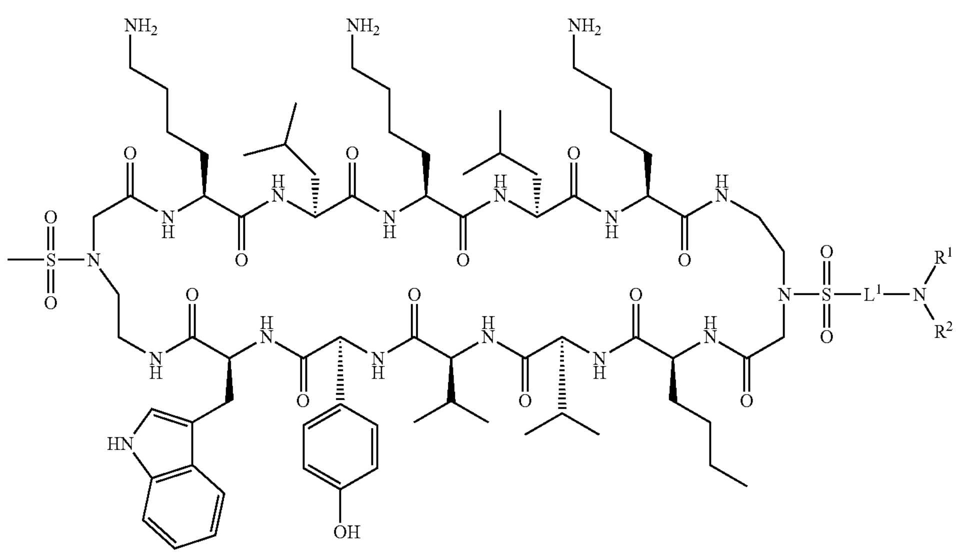 |

TABLE 2-continued

Exemplary compounds of structure of Formula (I)

| No. | Structure* |
|---|---|
| II-11 | 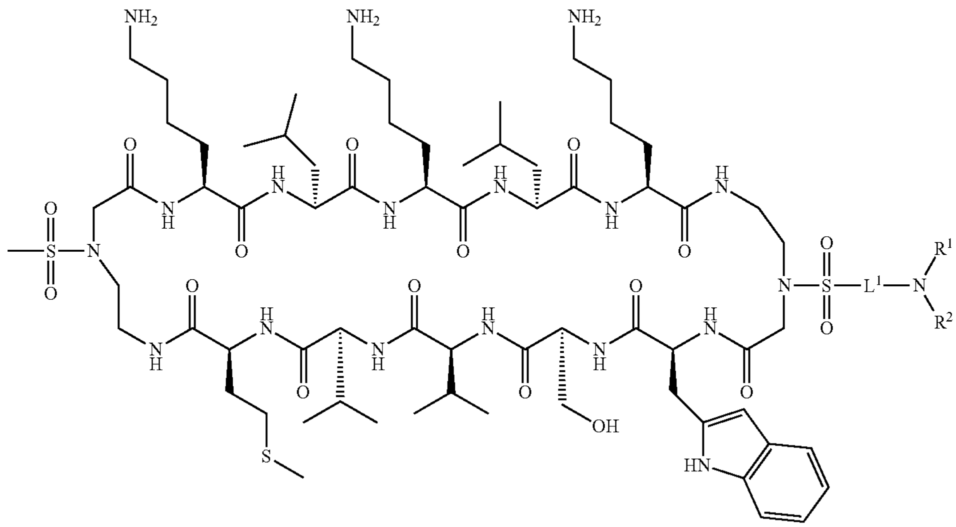 |
| II-12 | 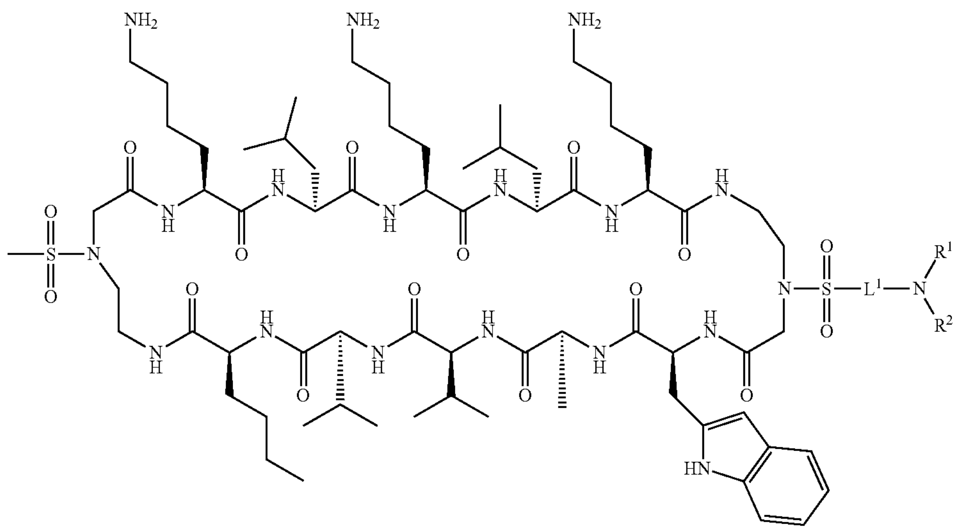 |
| II-13 | 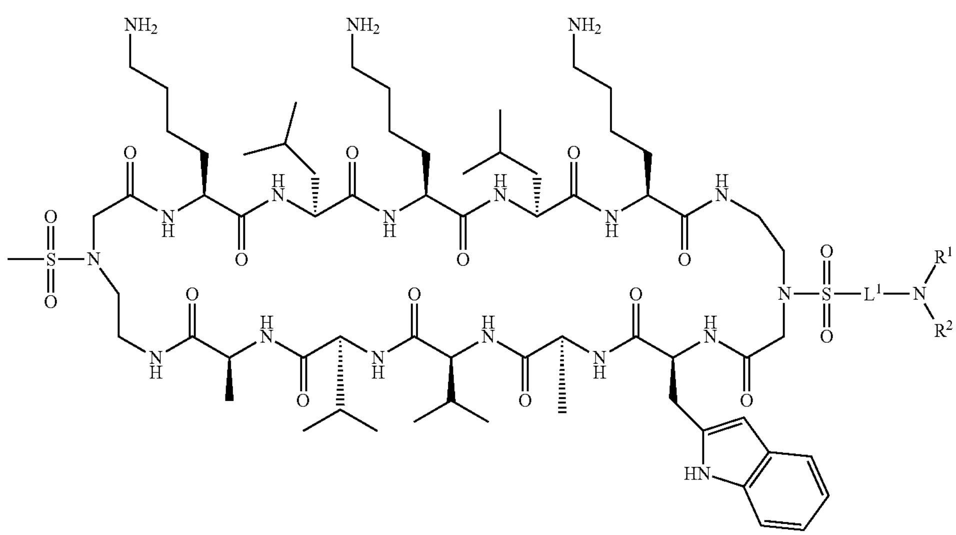 |

TABLE 2-continued
Exemplary compounds of structure of Formula (I)
| No. | Structure* |
| --- | --- |
| II-14 | 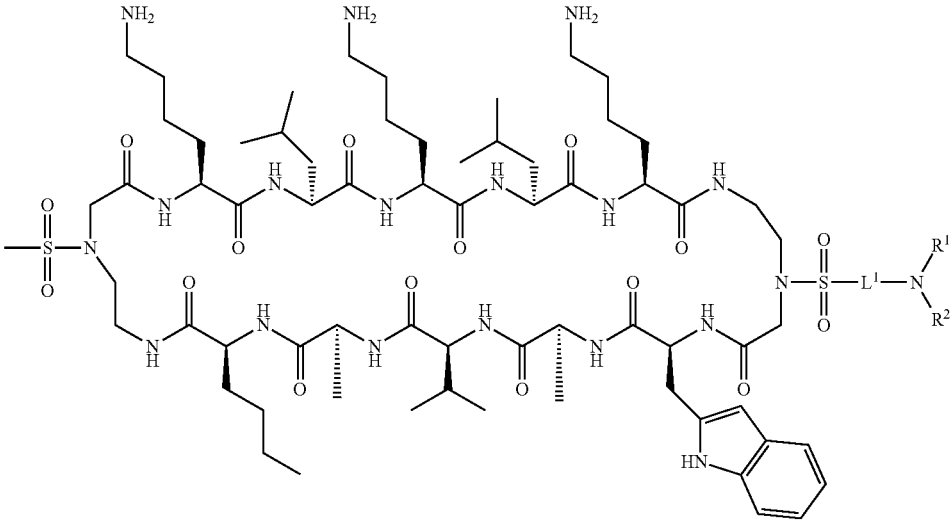 |
| II-15 | 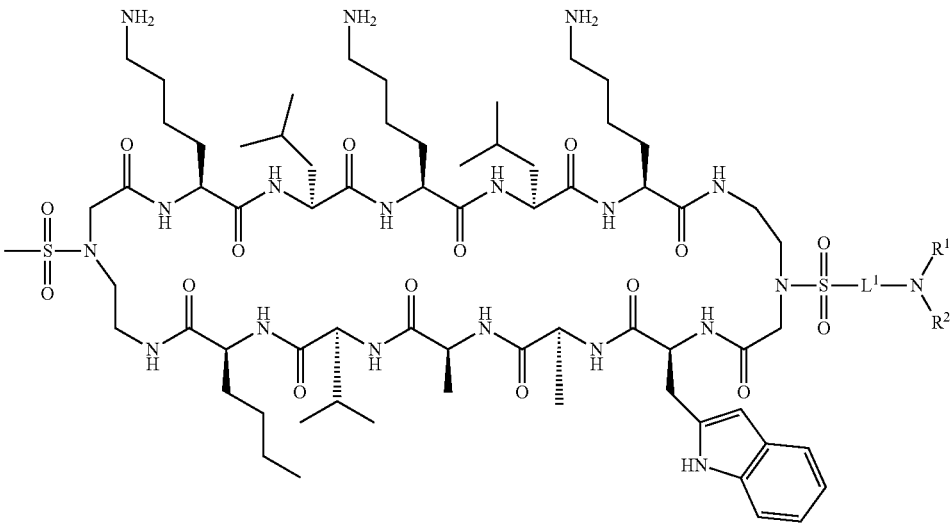 |
| II-16 | 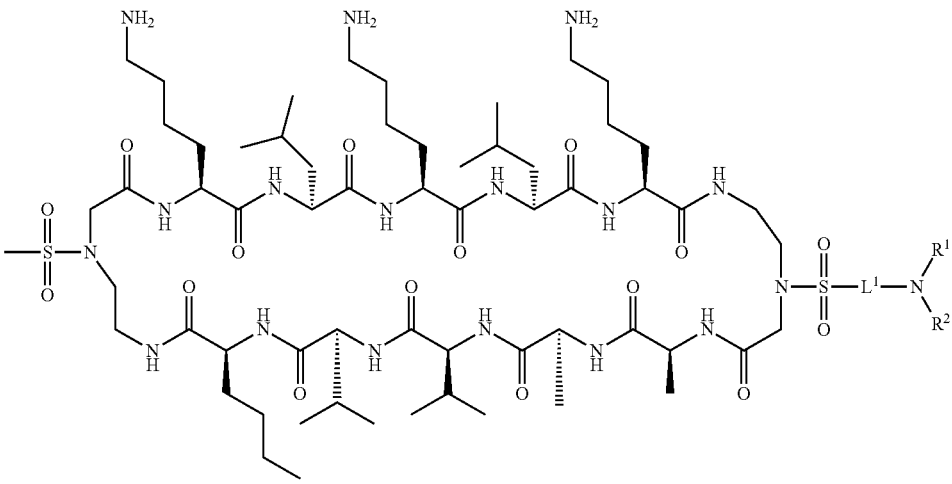 |

TABLE 2-continued
Exemplary compounds of structure of Formula (I)
| No. | Structure* |
|---|---|
| II-17 | 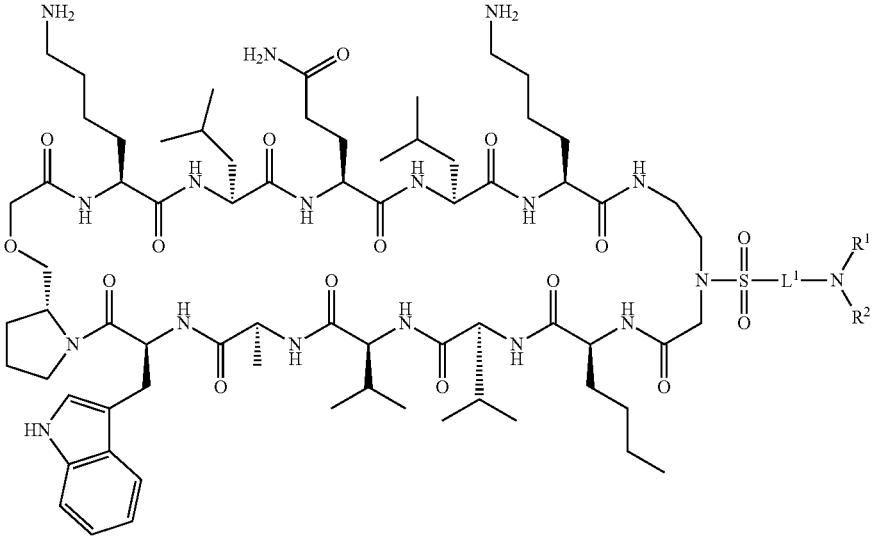 |
| II-18 | 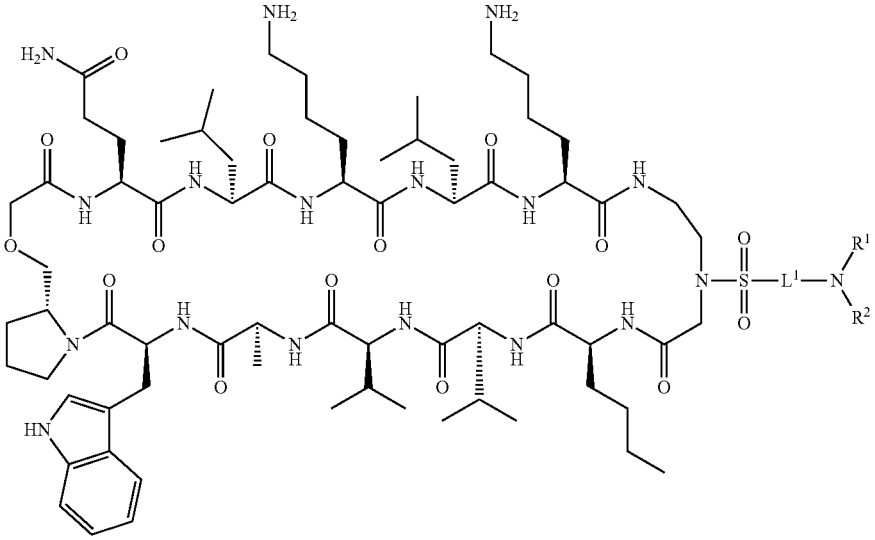 |

TABLE 2-continued
Exemplary compounds of structure of Formula (I)
| No. | Structure* |
|---|---|
| II-19 | 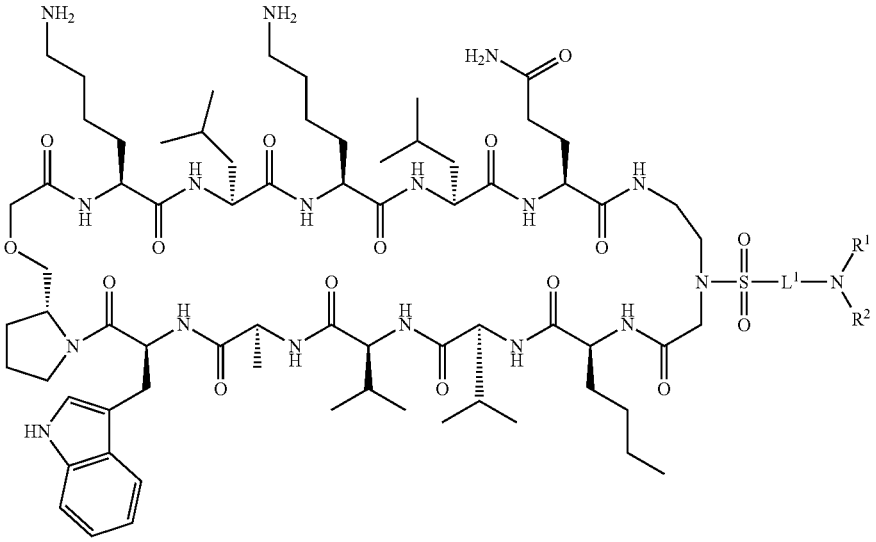 |
| II-20 | 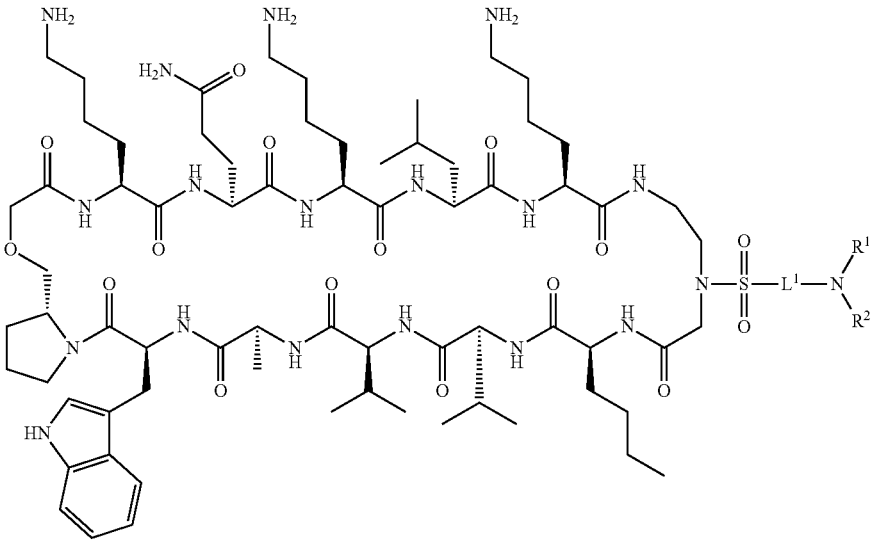 |

TABLE 2-continued
Exemplary compounds of structure of Formula (I)
| No. | Structure* |
|---|---|
| II-21 | 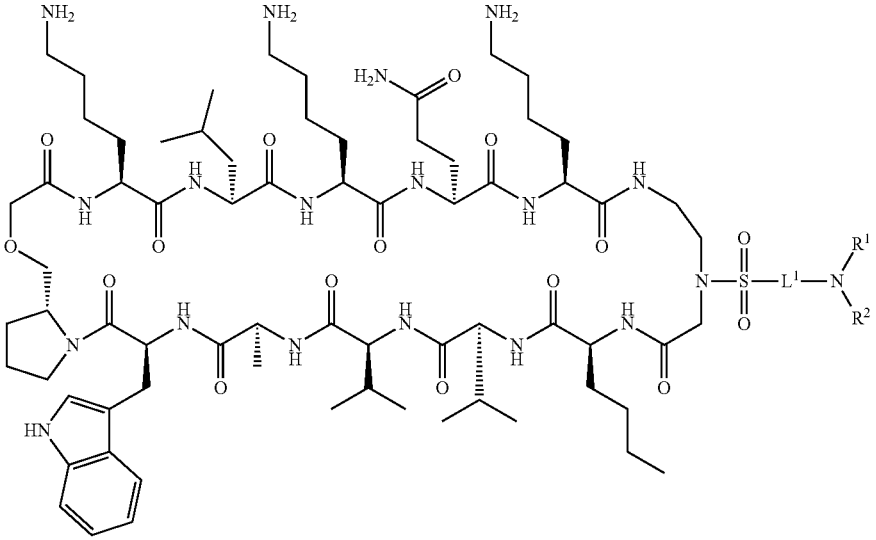 |
| II-22 | 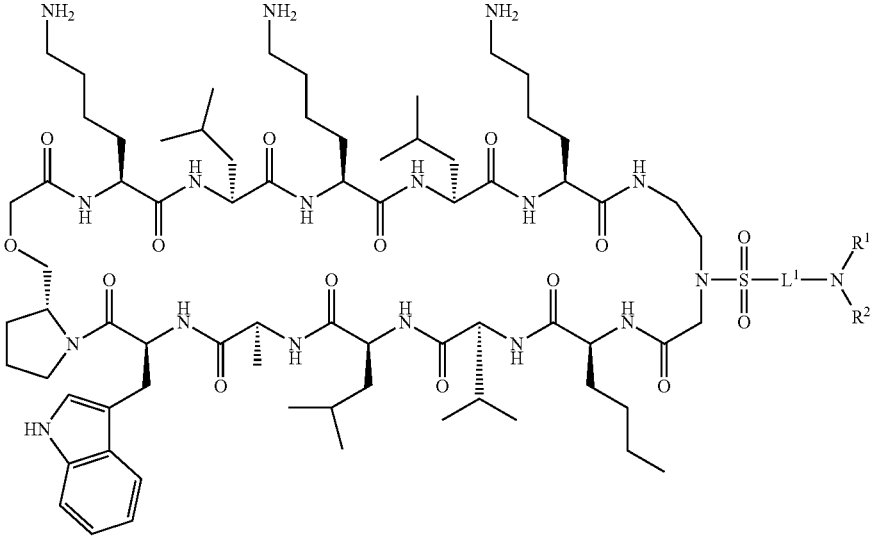 |

TABLE 2-continued
Exemplary compounds of structure of Formula (I)
| No. | Structure* |
|---|---|
| II-23 | 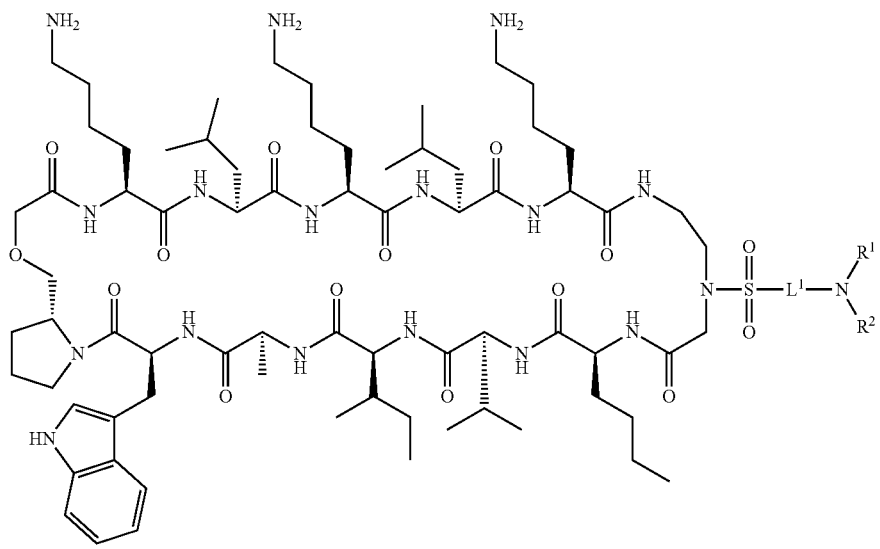 |
| II-24 | 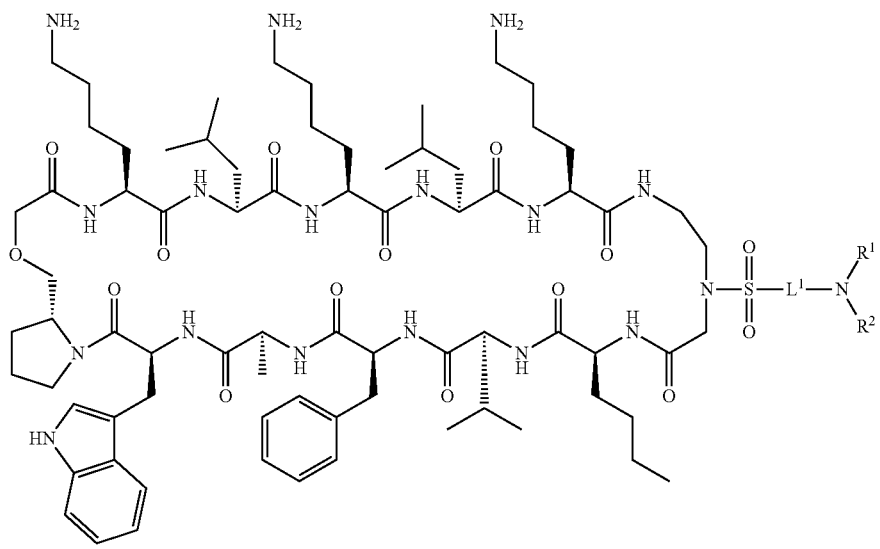 |
*L$^1$, R$^1$ and R$^2$ in Table 2 are as defined in any of the foregoing embodiments disclosed herein.

Some embodiments provide a compound selected from the compounds of Table 3 below.

TABLE 3

Exemplary compounds of structure of Formula (I)

No. Structure

III-1

III-2

TABLE 3-continued
Exemplary compounds of structure of Formula (I)
No. Structure
III-3
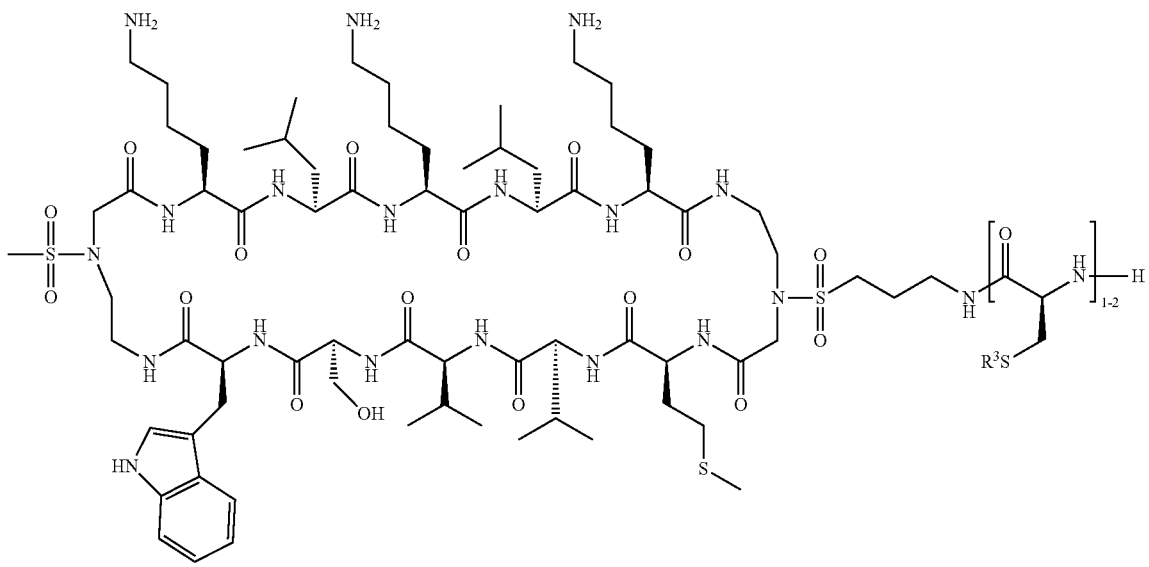
III-4
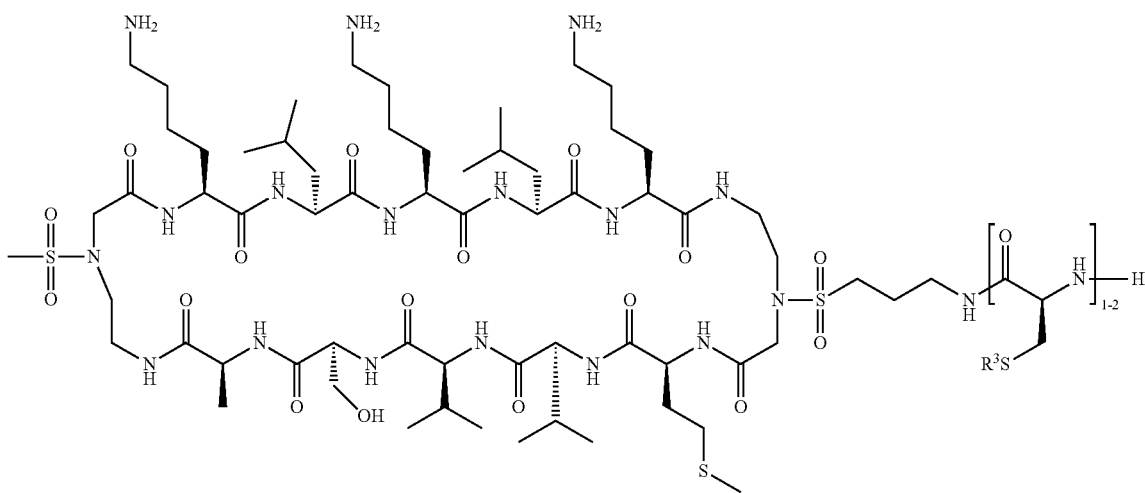

TABLE 3-continued
Exemplary compounds of structure of Formula (I)
No. Structure
III-5 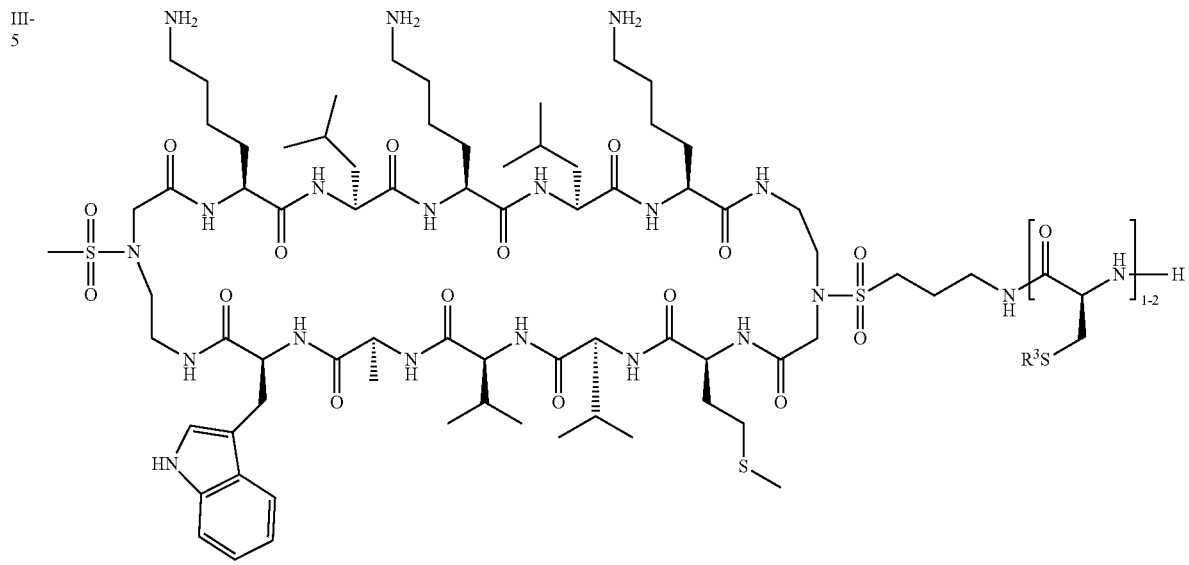
III-6 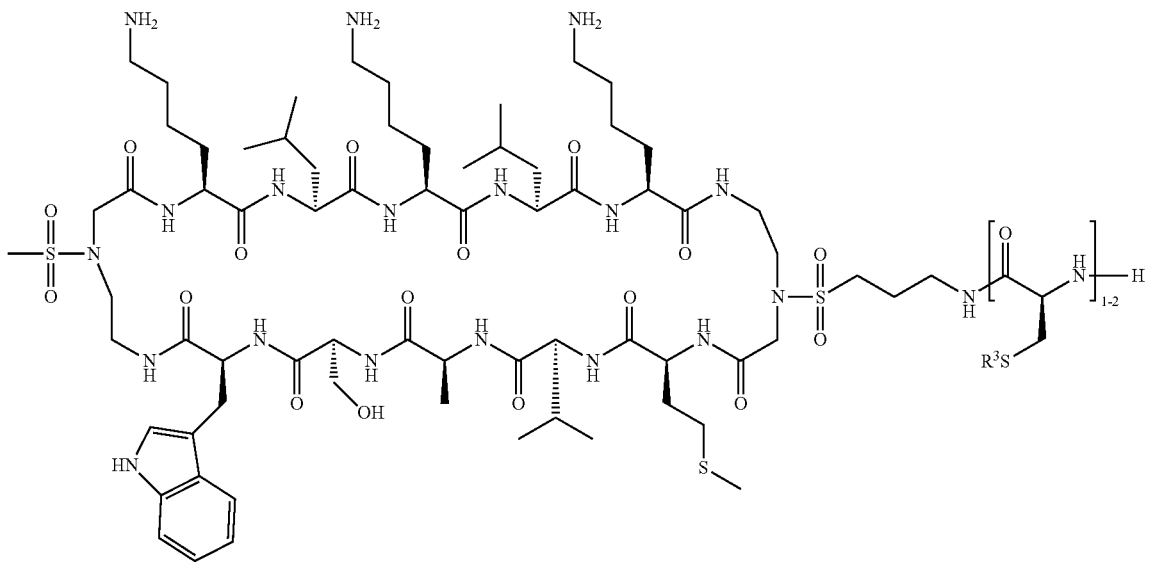

TABLE 3-continued
Exemplary compounds of structure of Formula (I)
No. Structure
III-7
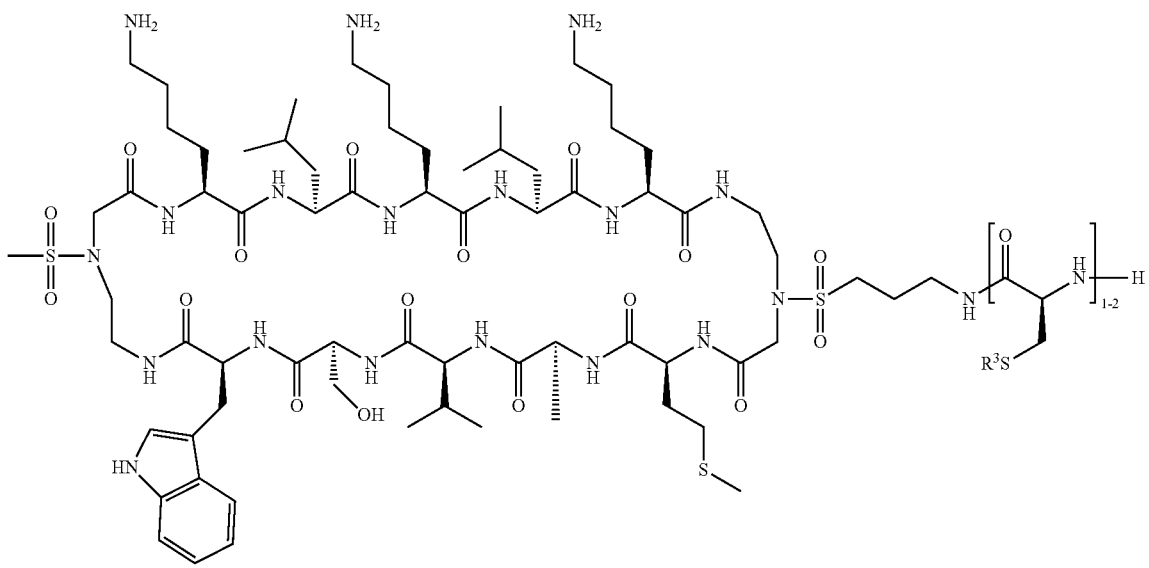
III-8
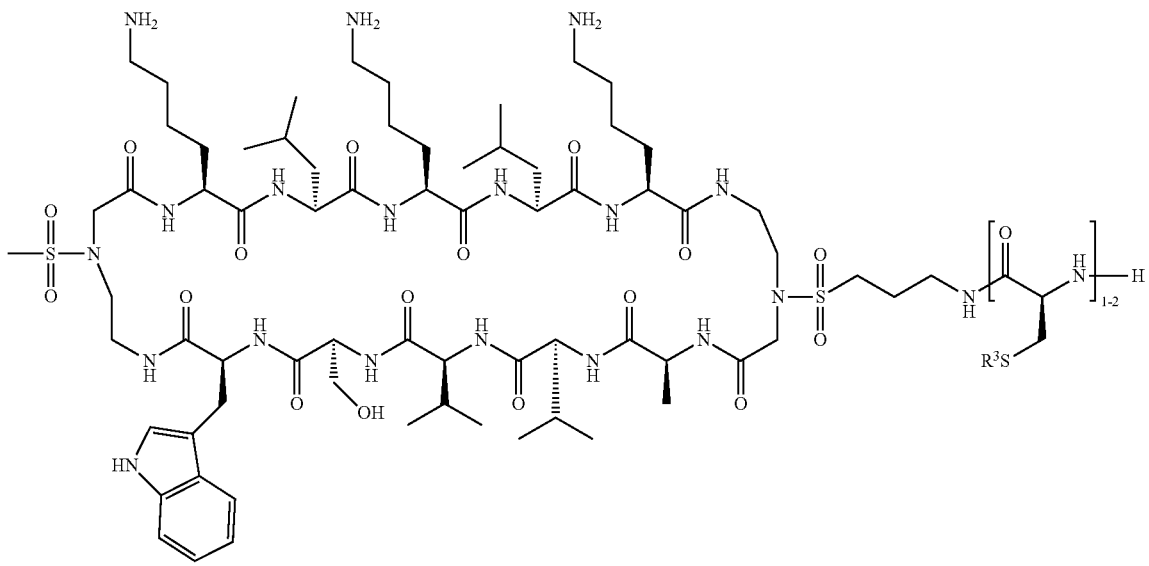

TABLE 3-continued
Exemplary compounds of structure of Formula (I)
No. Structure
III-9
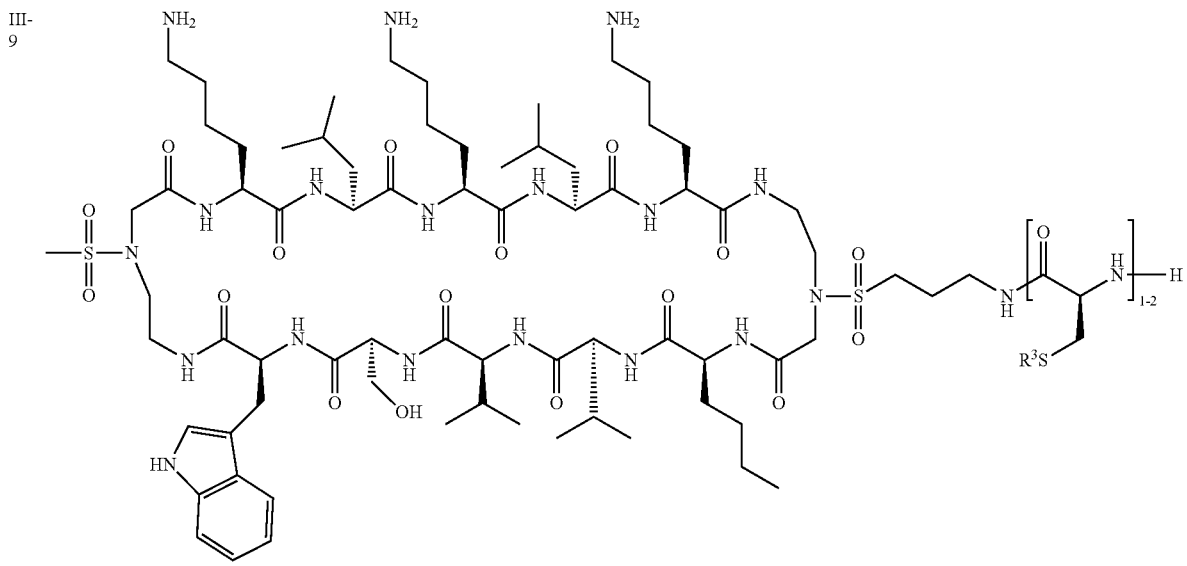
III-10
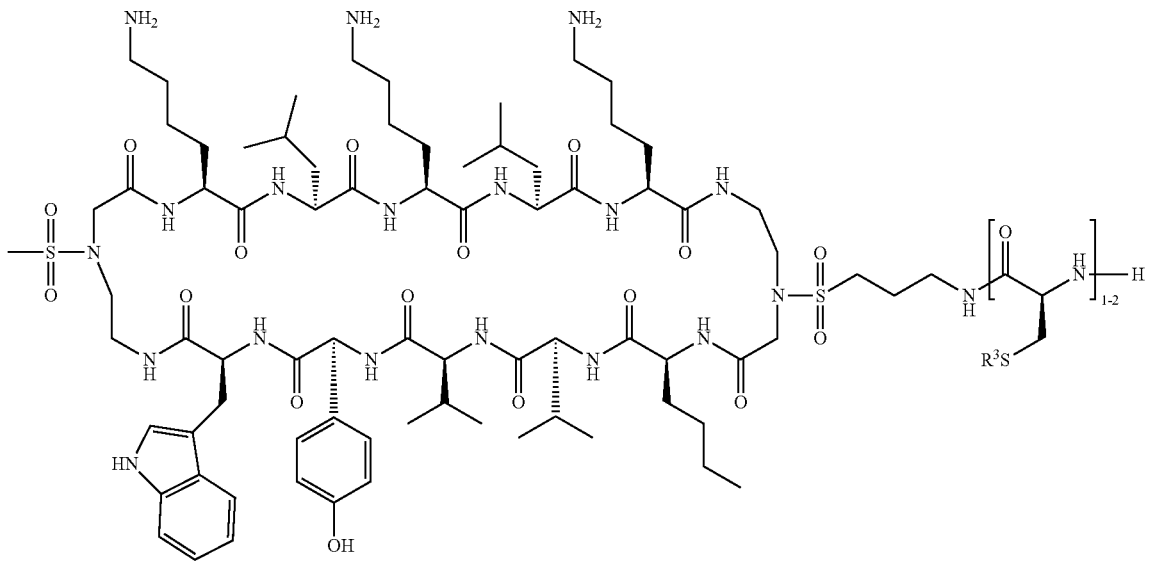

TABLE 3-continued
Exemplary compounds of structure of Formula (I)
No. Structure
III-11
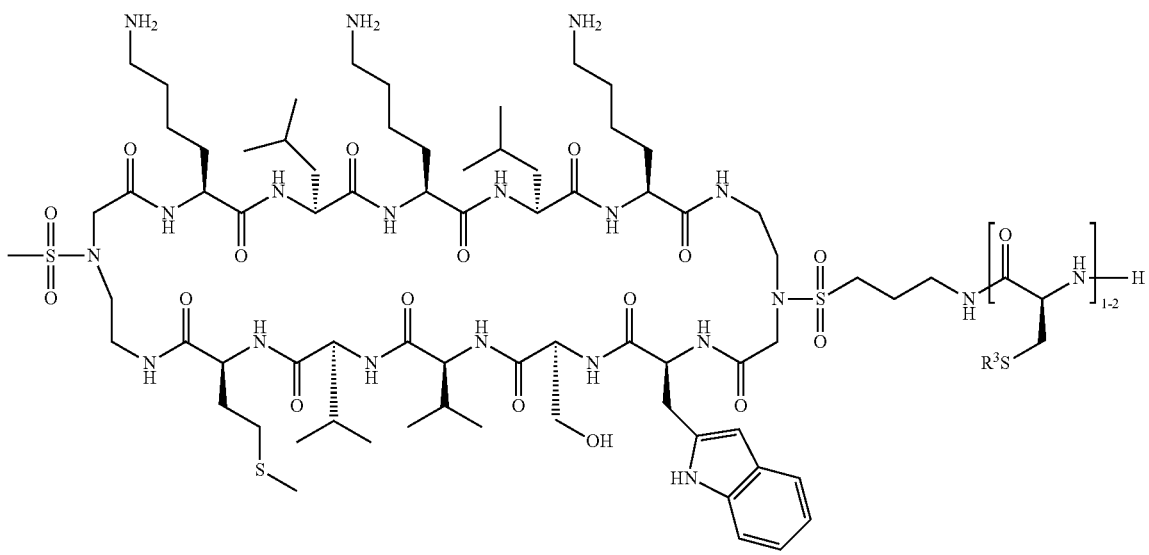
III-12
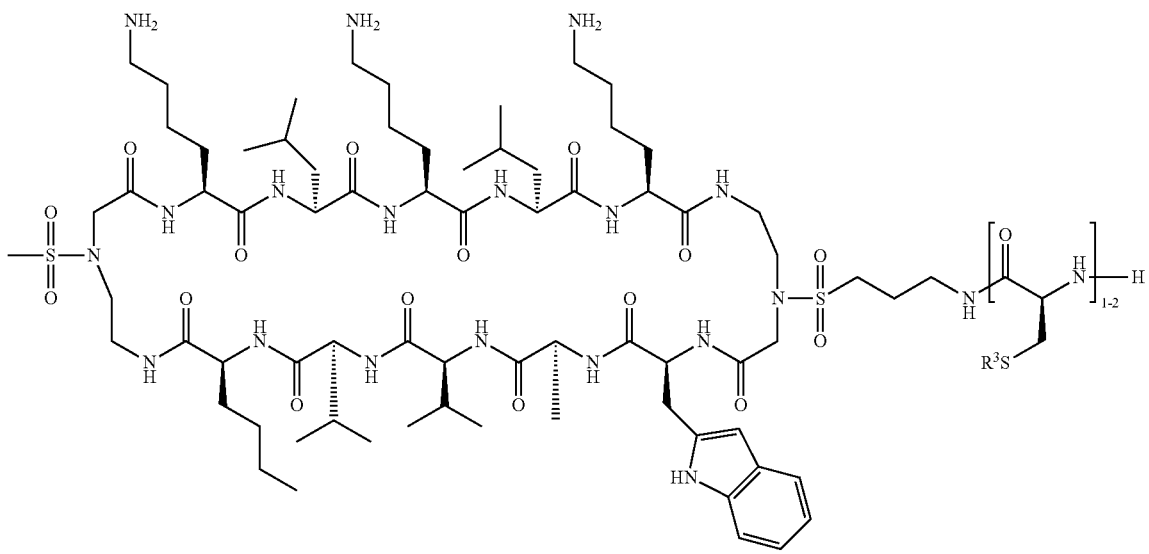

TABLE 3-continued
Exemplary compounds of structure of Formula (I)
No. Structure
III-13
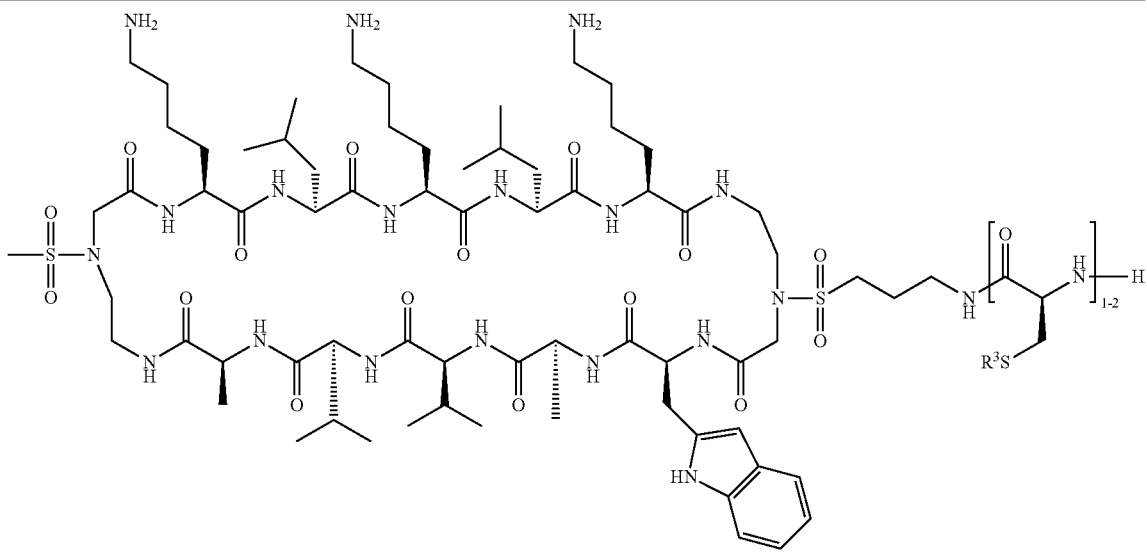
III-14
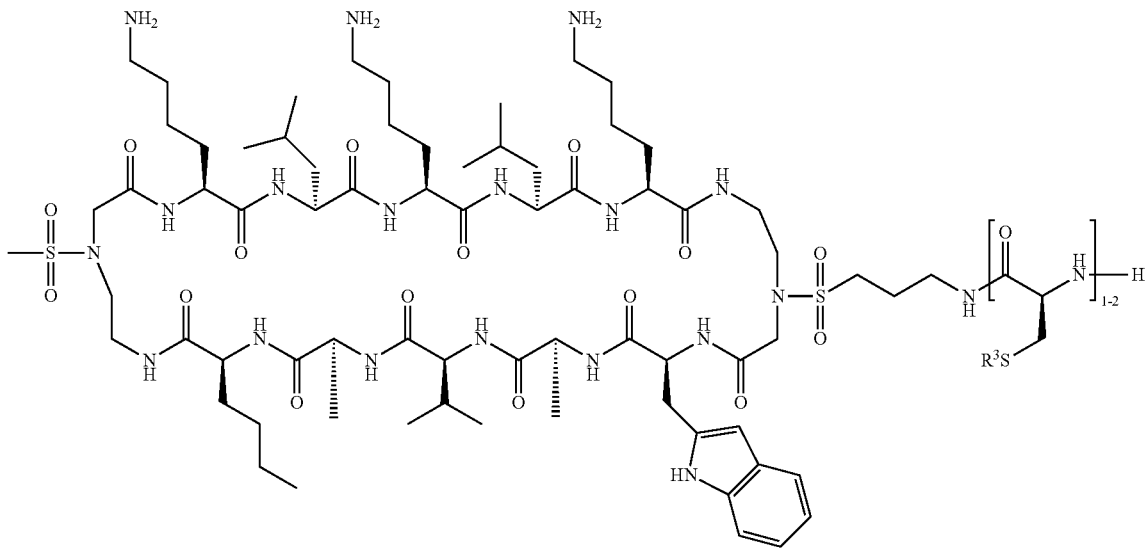

TABLE 3-continued
Exemplary compounds of structure of Formula (I)
No. Structure
III-15 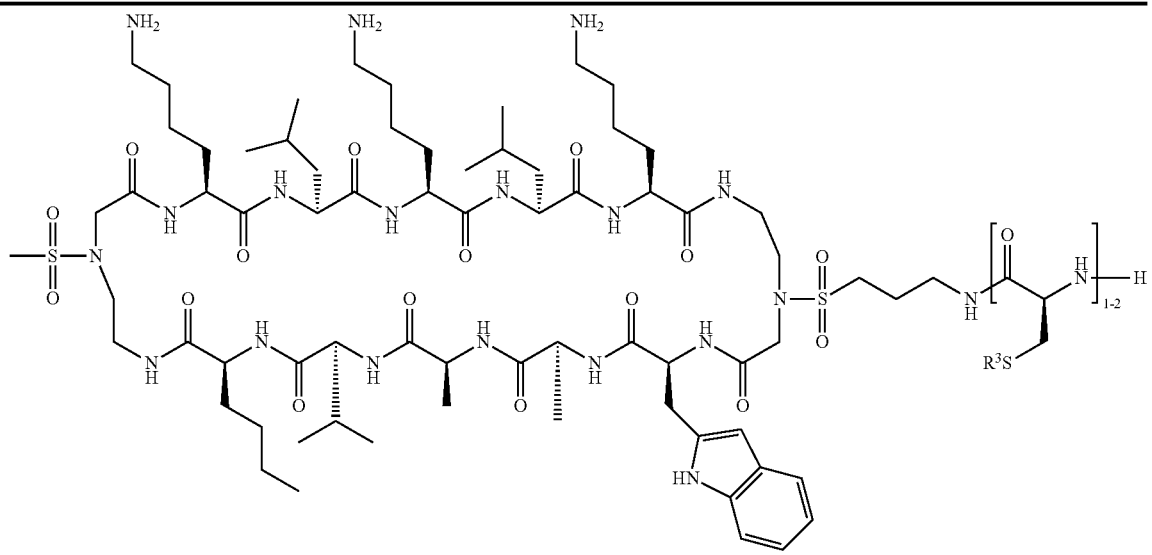
III-16 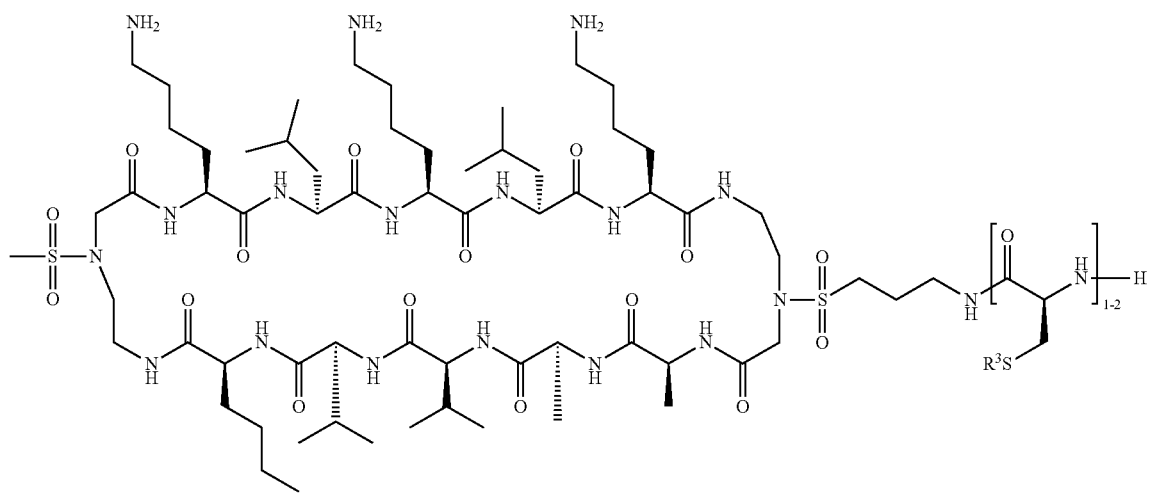
III-17 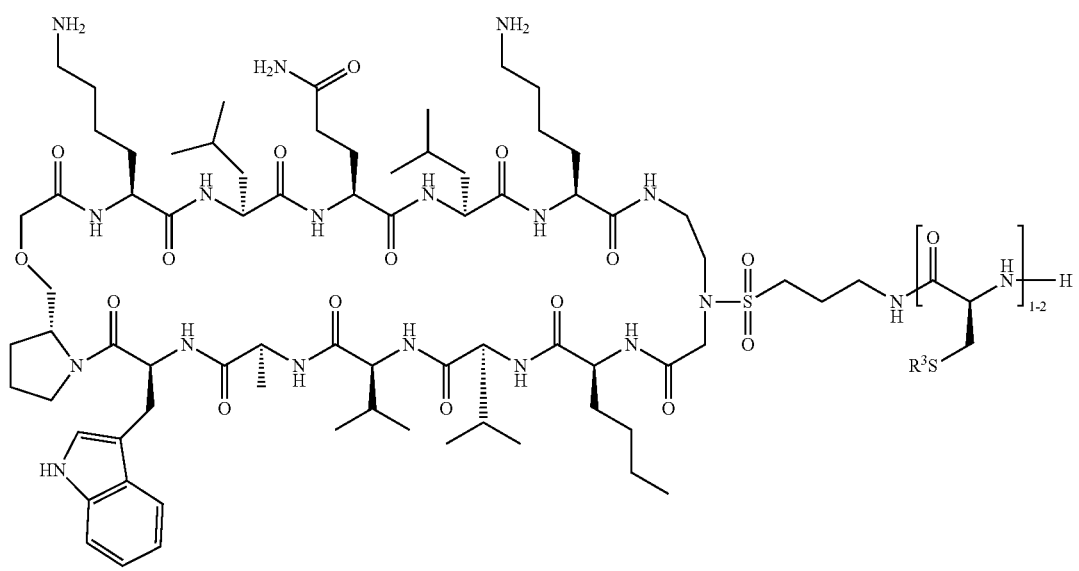

TABLE 3-continued
Exemplary compounds of structure of Formula (I)
No. Structure
III-18
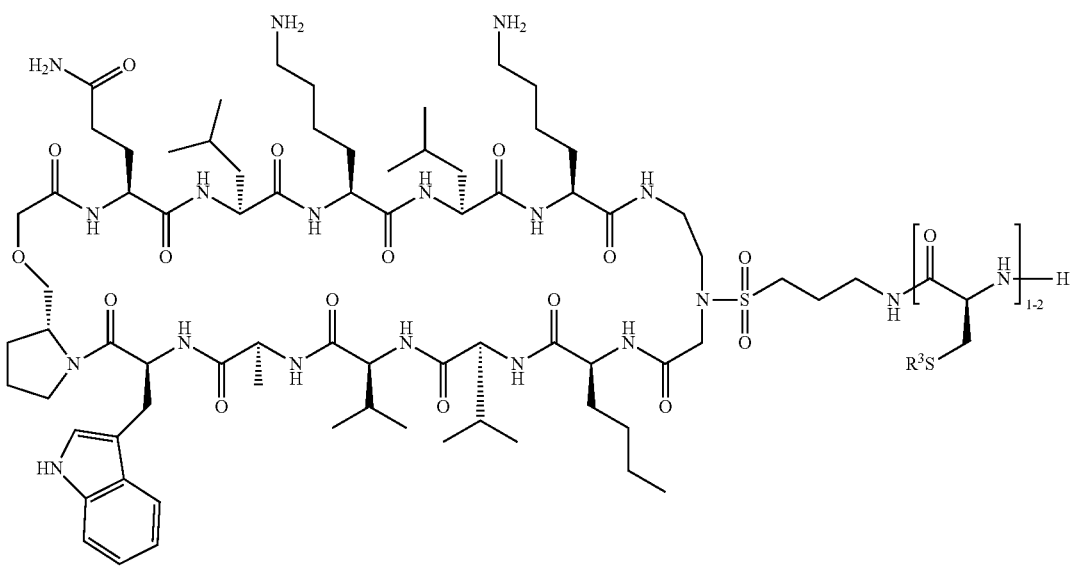
III-19
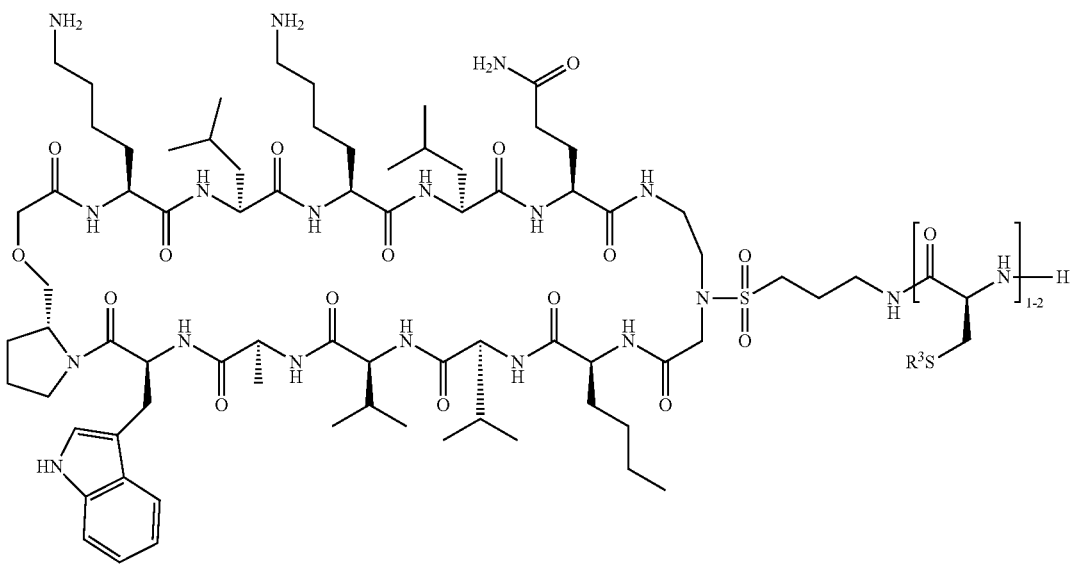

TABLE 3-continued
Exemplary compounds of structure of Formula (I)
No. Structure
III-20
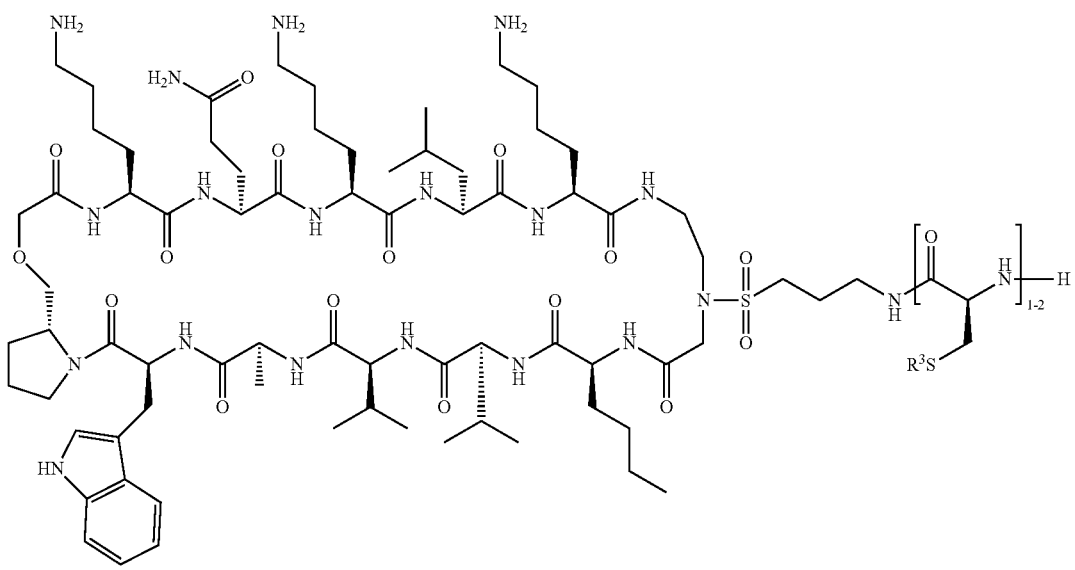
III-21
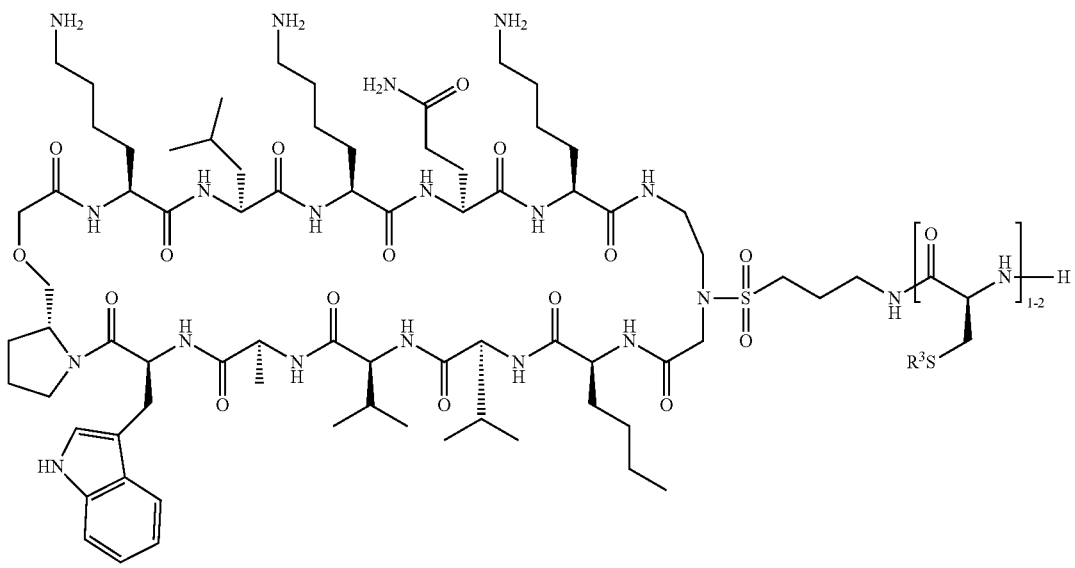

TABLE 3-continued

Exemplary compounds of structure of Formula (I)

| No. | Structure |
|---|---|
| III-22 | 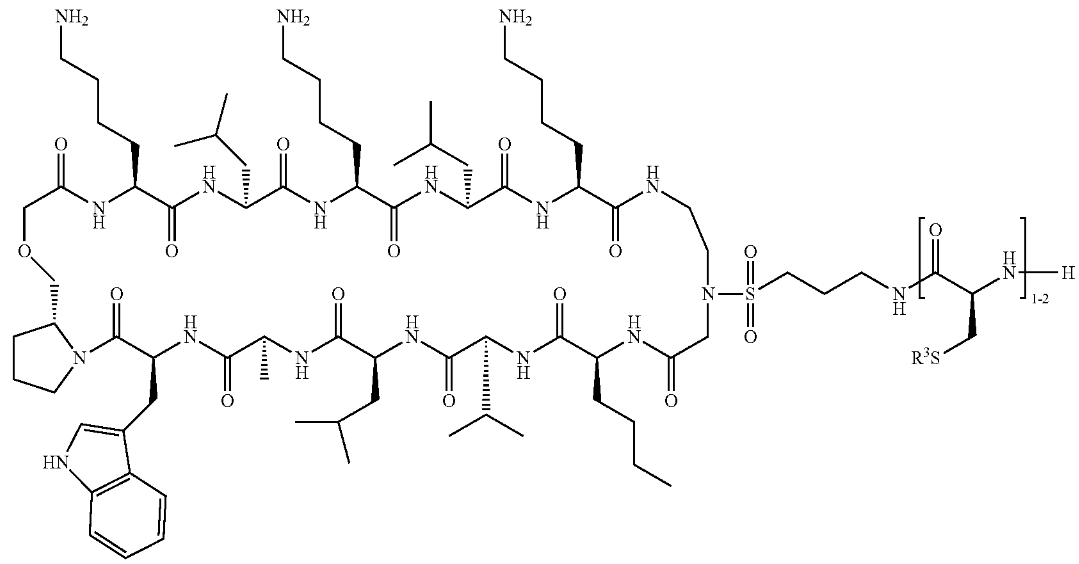 |
| III-23 | 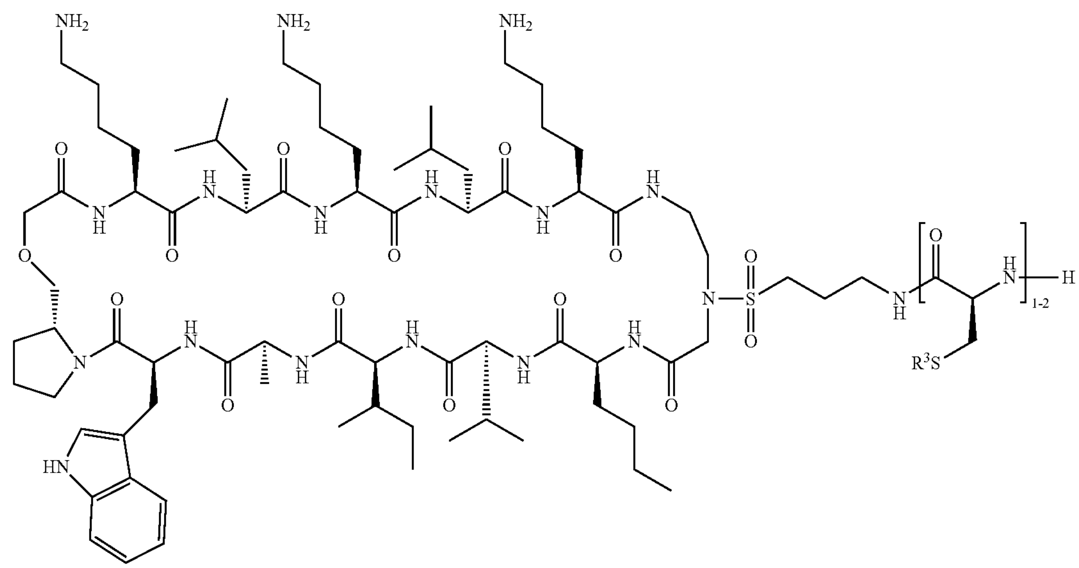 |

TABLE 3-continued

Exemplary compounds of structure of Formula (I)

| No. | Structure |
|---|---|
| III-24 | *(chemical structure)* |

*Each occurrence of R³ in Table 3 is independently as defined in any of the foregoing embodiments disclosed herein.

In certain embodiments of the compounds of Table 3, the variable is 1. In other embodiments of the compounds of Table 3, the variable is 2.

B. Compositions

In one embodiment, a composition comprising a compound according to the foregoing and a pharmaceutically acceptable carrier or excipient is described. In some embodiments, the compounds described herein (e.g., compounds of Formula (I)) are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions comprising a compound (e.g., a compound of Formula (I)) and a pharmaceutically acceptable diluent(s), excipient(s), or carrier(s) are provided herein. In certain embodiments, the compounds described are administered as pharmaceutical compositions in which compounds are mixed with other active ingredients (e.g., an anti-cancer agent), as in combination therapy. Encompassed herein are all combinations of active ingredients set forth in the combination therapies section below and throughout this disclosure. In specific embodiments, the pharmaceutical compositions include one or more compounds described herein.

A "composition" (used interchangeably with "pharmaceutical composition" herein), refers to a mixture of a compound (e.g., a compound of Formula (I)) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of a compound are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used, autoimmune responses and other factors. The compounds described herein can be used singly or in combination with one or more therapeutic agents as components of mixtures.

In one embodiment, a composition comprises a compound as described herein (e.g., a compound of Formula (I)) and a pharmaceutically acceptable carrier, excipient, glidant, sweetening agent, diluent, preservative, dye/colorant, flavor enhancer, surfactant, wetting agent, dispersing agent, suspending agent, stabilizer, isotonic agent, solvent or emulsifier which has been approved by the United States Food and Drug Administration as being acceptable for use in humans or domestic animals.

In some embodiments, a composition is as described above and comprises an additional bioactive agent, such as, for example, an anti-cancer agent. "Anti-cancer agent" refers to chemotherapeutic agents, cytotoxic agents, and non-peptide small molecules. Examples of anti-cancer agents include, but are not limited to Gleevec® (Imatinib Mesylate), Velcade® (bortezomib), Casodex (bicalutamide), Iressa® (gefitinib), and Adriamycin. "Anti-cancer agents" also refers to and includes alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included within the meaning of "anti-cancer agent" are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO). Where desired, the compounds of compositions of the present disclosure can be used in combination with commonly prescribed anti-cancer agents such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

In certain embodiments, one or more compound(s) (e.g., a compound of Formula (I)) is/are formulated in an aqueous solution. In specific embodiments, the aqueous solution is selected from, by way of example only, a physiologically compatible buffer, such as Hank's solution, Ringer's solution, or physiological saline buffer. In other embodiments, one or more compound(s) is/are formulated for transmucosal administration. In specific embodiments, transmucosal formulations include penetrants that are appropriate to the barrier to be permeated. In still other embodiments wherein the compounds described herein are formulated for other parenteral injections; appropriate formulations include aqueous or non-aqueous solutions. In specific embodiments, such solutions include physiologically compatible buffers and/or excipients.

In certain embodiments, compositions are formulated in any conventional manner using one or more physiologically acceptable carriers which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound as described herein are manufactured in a conventional manner, such as, by way of example only, by means of conventional mixing, dissolving, granulating, dragee-making, levigating, emulsifying, encapsulating, entrapping or compression processes.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the concentration of one or more compounds provided in the pharmaceutical compositions is less than 100%, 90%, 80%, 70%, 60%, 50%, 40%, 30%, 20%, 19%, 18%, 17%, 16%, 15%, 14%, 13%, 12%1, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds in the pharmaceutical composition is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds in the pharmaceutical composition ranges from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds in the pharmaceutical composition ranges from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

C. Methods of Treatment

In one embodiment, a method of treating a disease, the method comprising administering to a subject in need thereof a therapeutically effective amount of a compound or composition as described herein above is presented.

The diseases that can be treated, according to compounds, compositions and methods of the present disclosure, include cancers of various types. Various cancers that can be treated, according to an embodiment of the disclosure, are well known to a person of ordinary skill in the art and such cancers are within the purview of the current disclosure.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. Accordingly, in some embodiments, the pharmaceutical composition is formulated for oral administration. In other embodiments, the pharmaceutical composition is formulated for injection (e.g., intravenous, parenteral).

In some embodiments, a compound (e.g., a compound of Formula (I)) or composition is administered in a single dose. Typically, such administration will be by injection, e.g., intravenous injection, in order to introduce the agent quickly. However, other routes are used as appropriate. A single dose of a compound may also be used for treatment of an acute condition.

In some embodiments, the compounds or compositions is administered in multiple doses. In some embodiments, dosing is about once, twice, three times, four times, five times, six times, or more than six times per day. In other embodiments, dosing is about once a month, once every two weeks, once a week, or once every other day. In another embodiment a compound or composition and another bioactive agent are administered together about once per day to about 6 times per day. In another embodiment the administration of a compound or composition and a bioactive agent continues for less than about 7 days. In yet another embodiment the administration continues for more than about 6, 10, 14, 28 days, two months, six months, or one year. In some cases, continuous dosing is achieved and maintained as long as necessary.

Administration of the compounds (e.g., compounds of Formula (I)) and compositions may continue as long as necessary. In some embodiments, the compounds or compositions are administered for more than 1, 2, 3, 4, 5, 6, 7, 14, or 28 days. In some embodiments, the compounds or compositions are administered for less than 28, 14, 7, 6, 5, 4, 3, 2, or 1 day. In some embodiments, the compounds or compositions are administered chronically on an ongoing basis, e.g., for the treatment of chronic effects.

In some embodiments, the compounds (e.g., compounds of Formula (I)) or compositions are administered in dosages. It is known in the art that due to intersubject variability in compound or composition pharmacokinetics, individualization of dosing regimen is necessary for optimal therapy. Dosing for compounds or compositions may be found by routine experimentation in light of the instant disclosure.

In some embodiments, the disease to be treated is cancer. As such, oncological disorders within the scope of this disclosure include, but are not limited to, cancer of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain.

Specific cancers contemplated for treatment with the present disclosure include multiple myeloma, lung cancer (e.g., EGFR-driven lung cancer) and prostate cancer. Accordingly, some embodiments provide a method for treatment of multiple myeloma, the method comprising administering an effective amount of a pharmaceutical composition as disclosed herein to a subject in need thereof. Other embodiments provide a method for treatment of lung cancer (e.g., EGFR-mediated lung cancer), the method comprising administering an effective amount of a pharmaceutical composition as disclosed herein to a subject in need thereof. Still other embodiments provide a method for treatment of prostate cancer, the method comprising administering an effective amount of a pharmaceutical composition as disclosed herein to a subject in need thereof.

Other embodiments include treatment of carcinomas, Karposi's sarcoma, melanoma, mesothelioma, soft tissue sarcoma, leukemia (acute lymphoblastic, acute myeloid, chronic lymphocytic, chronic myeloid, and other), and lymphoma (Hodgkin's and non-Hodgkin's).

Other specific examples of cancers that can be treated according to the present disclosure include, but are not limited to acute lymphoblastic leukemia, acute myeloid leukemia, adrenocortical carcinoma, AIDS-related cancers (e.g., lymphoma), anal cancer, astrocytoma, basal cell carcinoma, bile duct cancer, bladder cancer, bone cancer, brain tumors (e.g., brain stem glioma, cerebellar astrocytoma, cerebral astrocytoma/malignant glioma, ependymoma, medulloblastoma, supratentorial primitive neuroectodermal, visual pathway and hypothalamic glioma), breast cancer, bronchial adenomas/carcinoids, Burkitt's Lymphoma, carcinoid tumor (e.g., gastrointestinal), cervical cancer, childhood cancers, chronic lymphocytic leukemia, chronic myelogenous leukemia, chronic myeloproliferative disorders, colon cancer, colorectal cancer, cutaneous T-cell lymphoma (e.g., mycosis fungoides and Sezary Syndrome), endometrial cancer, ependymoma, esophageal cancer, Ewing's Tumors, germ-cell tumors (e.g., extracranial, extragonadal, ovarian), extrahepatic bile duct cancer, eye cancer (e.g., intraocular melanoma, retinoblastoma), gallbladder cancer, gastric (stomach) cancer, gastrointestinal carcinoid tumors, gestational trophoblastic tumors, glioma, head and neck cancer, hepatocellular (liver) cancer, Hodgkin's Lymphoma, hypopharyngeal cancer, islet cell carcinoma, Kaposi's Sarcoma, kidney cancer (e.g., renal cell), laryngeal cancer, leukemia (e.g., hairy cell), lip and oral cavity cancer, liver cancer, lung cancer, Non-Hodgkin's Lymphoma, primary central nervous system lymphoma, Waldenström's macroglobulinemia, melanoma, mesothelioma, metastatic squamous neck cancer with occult primary, multiple endocrine neoplasia syndrome, multiple myeloma/plasma cell neoplasm, myelodysplastic syndromes, myelodysplastic/myeloproliferative diseases, nasal cavity and paranasal sinus cancer, nasopharyngeal cancer, nasopharyngeal cancer, neuroblastoma, non-small cell lung cancer, oral cancer, oropharyngeal cancer, ovarian cancer (e.g., epithelial, germ-call, low malignant potential tumor), pancreatic cancer (e.g., islet cell), paranasal sinus and nasal cavity cancer, parathyroid cancer, penile cancer, pheochromocytoma, pineoblastoma, pituitary tumors, pleuropulmonary blastoma, pregnancy cancers (e.g., breast, Hodgkin's Lymphoma, Non-Hodgkin's Lymphoma, prostate cancer, rectal cancer, renal cancer, retinoblastoma, rhabdomyosarcoma, salivary gland cancer, sarcoma (e.g., Ewing's, Kaposi's, soft tissue, uterine), skin cancer (e.g., melanoma, Merkel Cell, squamous cell carcinoma), small cell lung cancer, small intestine cancer, soft tissue sarcoma, squamous neck cancer with occult primary, supratentorial primitive neuroectodermal tumors, testicular cancer, thymoma and thymic carcinoma, thyroid cancer, transitional cell cancer of the renal pelvis and ureter, trophoblastic tumors, urethral cancer, uterine cancer (e.g., endometrial, sarcoma), vaginal cancer, vulvar cancer, and Wilms' tumors.

In certain embodiments of the method described above, the method further comprises administering a bioactive agent to the subject simultaneously or consecutively with the compound or composition. In some more specific embodiments, the bioactive agent is an anti-cancer agent. In some of the foregoing embodiments, the bioactive agent is administered within the same formulation as the compound. In other embodiments, the bioactive agent is administered within a formulation that is separate from the compound.

In one embodiment, a method for delivering a compound to a cell or tissue, the method comprising administering to the cell or tissue in vitro or in vivo a compound or composition as described herein above is presented. In some of those embodiments, the cell or tissue is diseased, for example, a cancer cell or tissue.

D. Methods of Preparation

One embodiment provides a method for preparing a compound having a structure of Formula (I):

$$X\text{-}L^1\text{-}N(R')R^2, \qquad (I)$$

or a pharmaceutically acceptable salt, tautomer, or stereoisomer thereof, wherein:

X is a cyclic β-hairpin peptidomimetic;

L is an optional linker; and $R^1$ is H; and $R^2$ is H or a moiety comprising one or more amino acid residues or substituted derivatives thereof. For example, the compound may be a compound having a structure of Formula (I) according to any of the embodiments described herein. Accordingly, in some embodiments, the method comprises:

One embodiment provides a method for preparing a compound having a structure of Formula (I), the method comprising modifying a cyclic β-hairpin peptidomimetic to include a linker $L^1$. In some more specific embodiments, the linker $L^1$ is modified to include one or more amino acid residues or derivatives thereof.

In certain specific embodiments, the linker $L^1$ is modified to include one of the following structures:

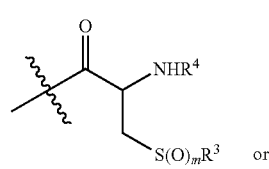 or

-continued

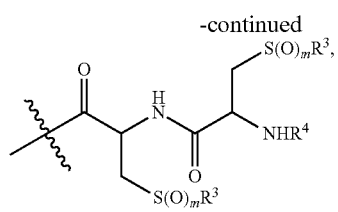

wherein:
R³ is, at each occurrence, independently H, a protecting group, alkyl, aminoalkyl, a protected aminoalkyl, hydroxyalkyl, a protected hydroxyalkyl, or -L²-Y
R⁴ is H or an amine protecting group;
m is, at each occurrence, independently, 0, 1 or 2;
L² is a linker; and
Y at each occurrence independently comprises one or more saccharide moieties.

Embodiments of the methods for preparing a compound having a structure of Formula (I) may include one more amino acid coupling steps according to the following Amino Acid Coupling Reaction Scheme.

Amino Acid Coupling Reaction Scheme

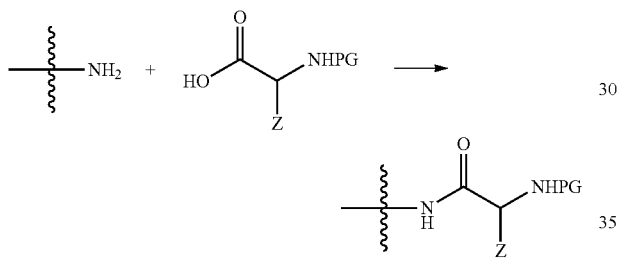

PG = Protecting Group (e.g., Fmoc, Boc)
Z = amino acid side chain

As shown above, the ⌇ may represent an attachment to an additional amino acid residue, a solid support, or linker (e.g., L¹). The protecting group can be selected based on the overall synthetic scheme (e.g., accounting for protecting groups of side chains, etc.). In one particular embodiment, the method for preparing a compound having a structure of Formula (I) includes an amino acid coupling step according to the amino acid coupling reaction scheme above. In more specific embodiments, the protecting group is an Fmoc protecting group.

In some embodiments, the amino acid side chain ("Z") is a cysteine side chain. In some embodiments, the amino acid side chain is a protected form of the amino acid side chain. In some embodiments, the amino acid side chain comprises H, a protecting group, alkyl, aminoalkyl, a protected aminoalkyl, hydroxyalkyl, a protected hydroxyalkyl, or -L²-Y, wherein L² and Y are defined according to the embodiments described herein.

The examples and preparations provided below further illustrate and exemplify the compounds and compositions of the present disclosure as well as methods of preparing and using such compounds. It is to be understood that the scope of the present disclosure is not limited in any way by the scope of the following examples and preparations.

EXAMPLES

Example 1

Synthesis of Exemplary Compound of Formula (I) (Compound 2)

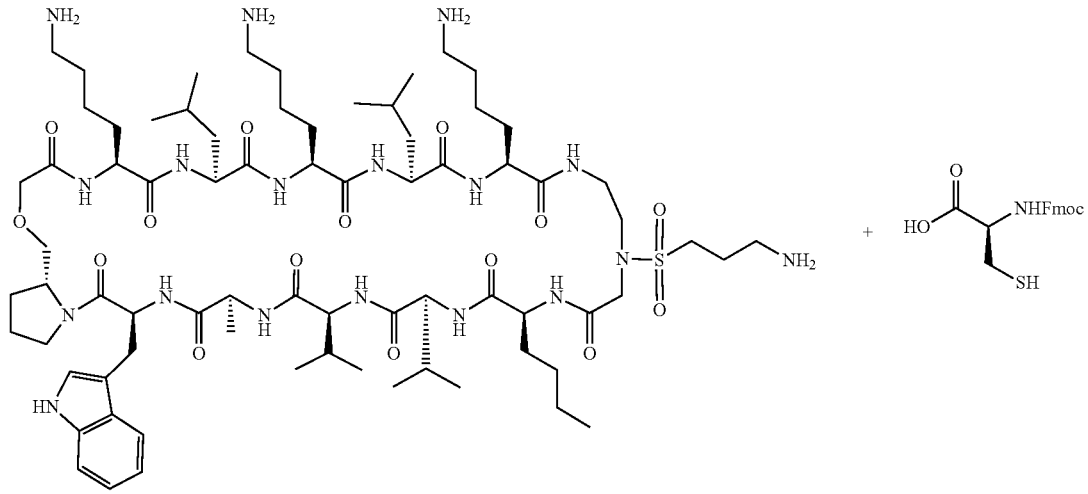

Compound 1

A-1

1. Amino Acid Coupling
2. Amine deprotection

-continued

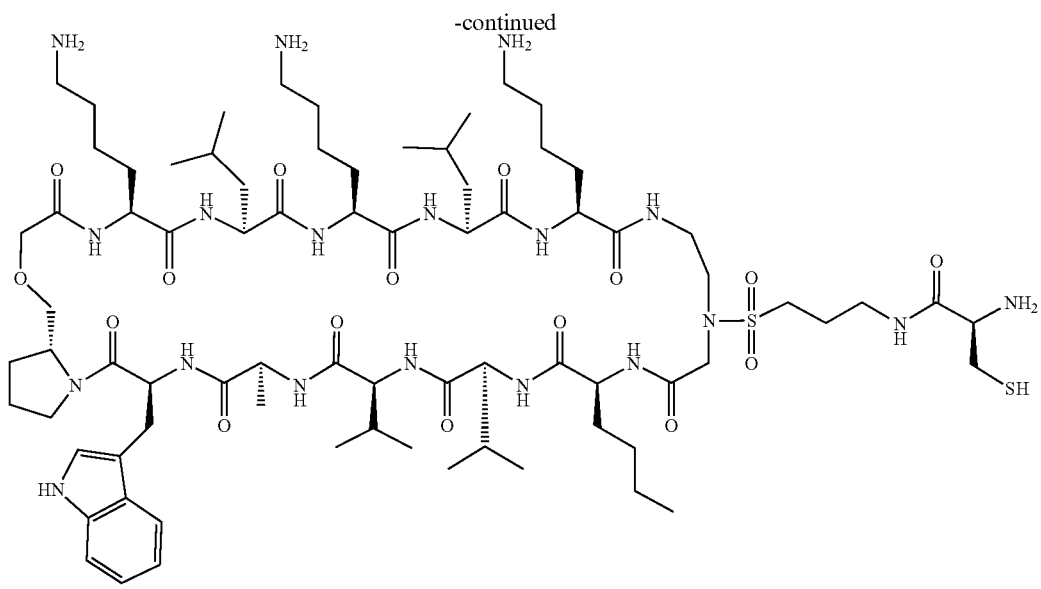

Compound 2

Compound 1 was obtained using standard peptide synthesis techniques (e.g., solid phase synthesis). Compound 1 was then coupled to the Fmoc-protected cysteine amino acid ("A-1") using standard amino acid coupling conditions (e.g., using carbodiimides such as DCC, DIC, or EDC, or alternatively, with aminium/uronium and phosphonium salts). The resultant compound was deprotected under appropriate conditions (e.g., 20-50% piperidine in DMF) to afford the desired product, which can be purified using standard techniques (e.g., silica gel or HPLC preparative chromatography). Alternatively, additional amino acid coupling steps can be used following the deprotection of the amine to add amino acid residues as desired (e.g., to obtain Compound 3).

Example 2

Alkylation of Cysteine Derivatives

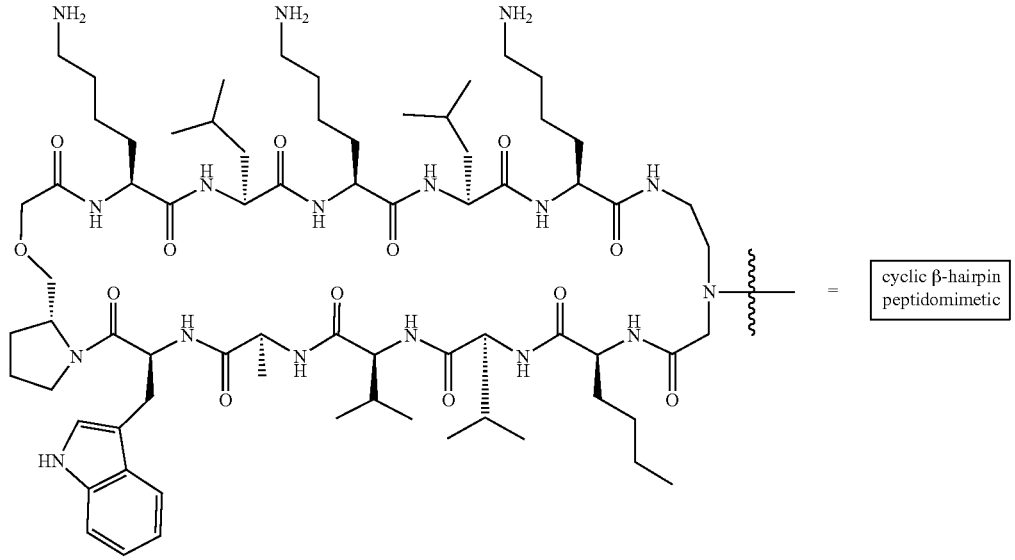

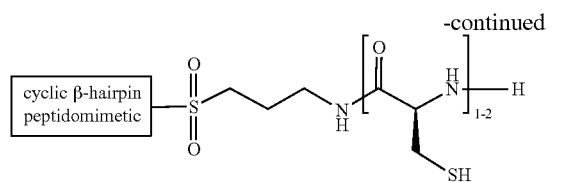

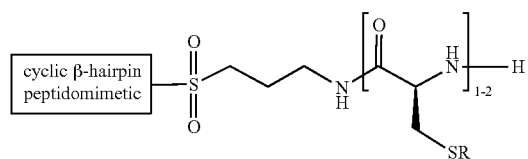

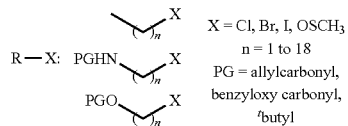

Cysteine derivatives of the exemplary compounds comprising a cyclic β-hairpin peptidomimetic synthesized according to Example 1 (e.g., Compound 2 or Compound 3; 1 equivalent) were dissolved in DMF with the desired alkylating agent ("R—X"; 1.05 equivalents). Diisopropylethylamine (2.2 equivalents) was added to the reaction mixture and the mixture was heated to 80° C. The reaction was monitored by thin layer chromatography using iodine stain and after the reaction is judged to be complete (approximately 2 hours) solvents were removed in vacuo. Protecting groups were removed using standard techniques (e.g., concentrated TFA at room temperature). The crude desired product was then purified by reverse phase chromatography to afford pure compounds. Also, saccharides shown below can be added selectively via the alkylation of the cysteine thiol groups. Alternatively the saccharides can added before the cysteines are attached to the cyclic β-hairpin peptidomimetic as shown in Example 2 below.

Example 3

Synthesis of Saccharide Derivatives

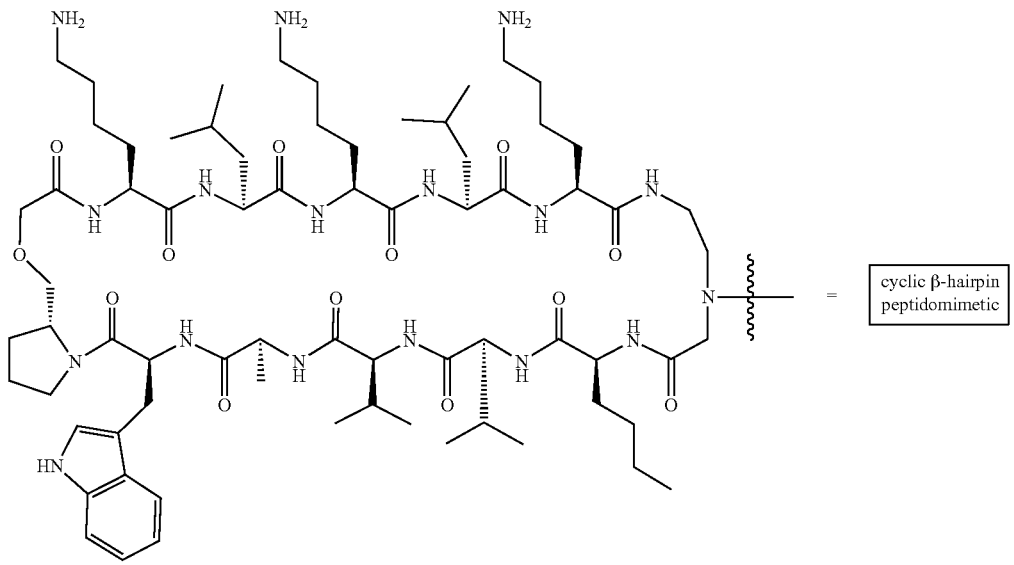

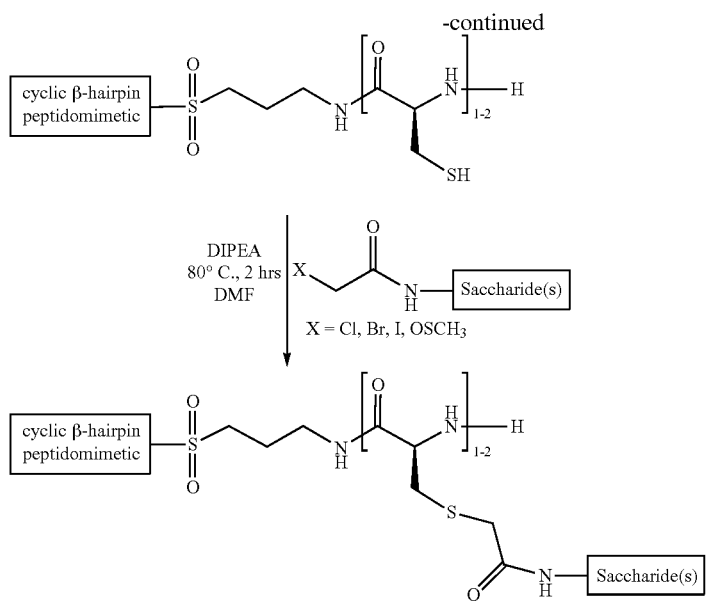

Cysteine derivatives of the exemplary compounds comprising a cyclic β-hairpin peptidomimetic synthesized according to Example 1 (e.g., Compound 2 or Compound 3; 1 equivalent) were dissolved in DMF with the desired saccharide derivative (1.05 equivalents). Diisopropylethylamine (2.2 equivalents) was added to the reaction mixture and the mixture was heated to 80° C. The reaction was monitored by thin layer chromatography using iodine stain and after the reaction is judged to be complete (approximately 2 hours) solvents were removed in vacuo. The crude desired product was then purified by reverse phase chromatography to afford pure compounds.

Example 4

Cysteine Derivatives

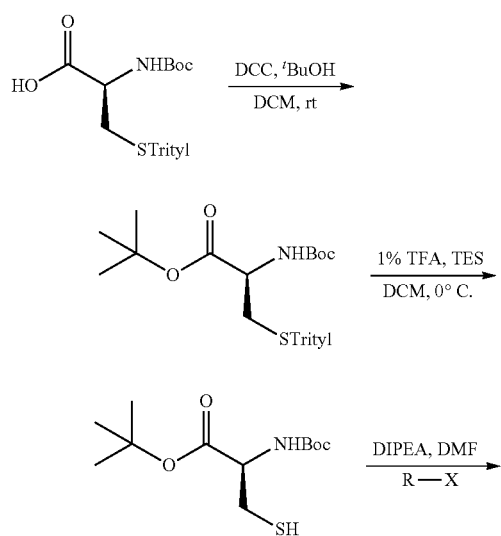

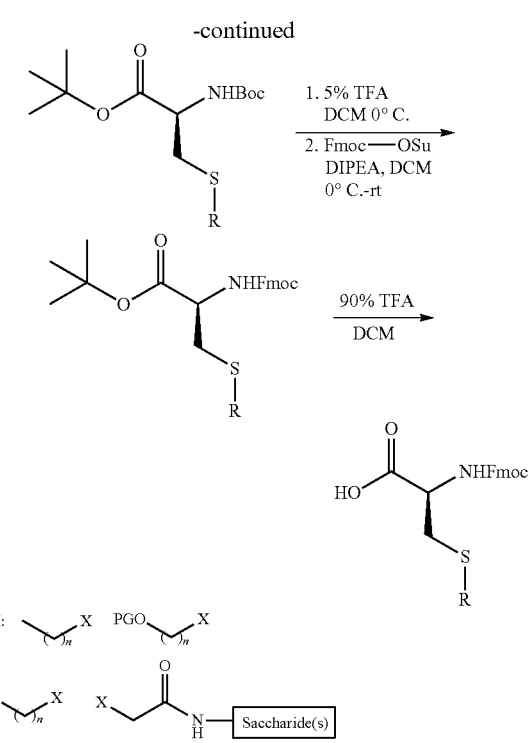

X = Cl, Br, I, OSCH$_3$
n = 1 to 18
PG = allyloxy carbonyl,
benzyloxy carbonyl,
$^t$butyl As an alternative to the synthetic strategies described in Examples 2 and 3, a cysteine amino acid monomer unit can be alkylated or derivatized with a saccharide derivative prior to attachment to the free amine of Compound 1. Using this strategy, the alkylating agents or saccharide derivatives attached to the sulfur of the cysteine residue can be the same or different and can be selected to modulate biological activity, solubility and bioavailability as desired.

Example 5

Potency of Exemplary Compounds

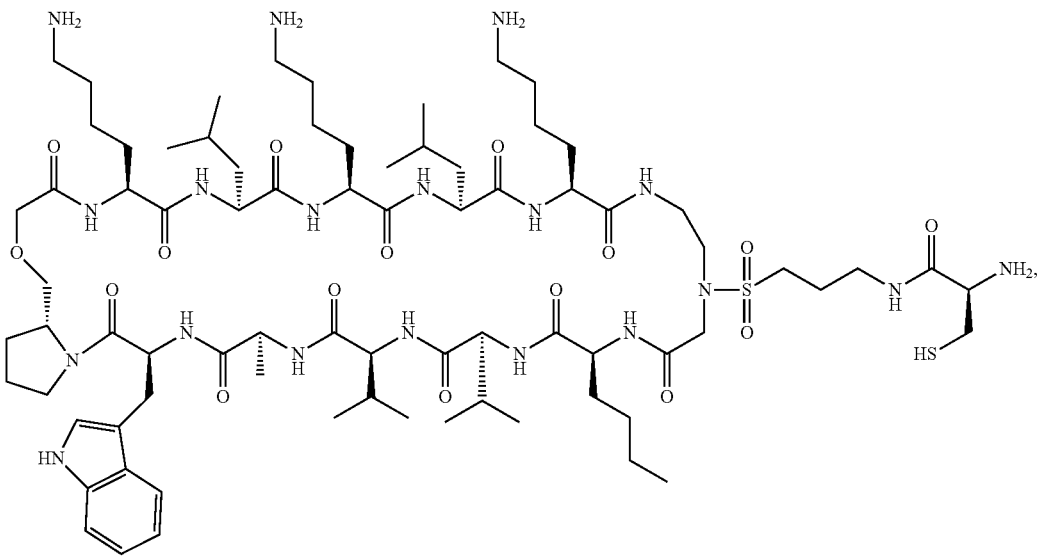

Compound 2

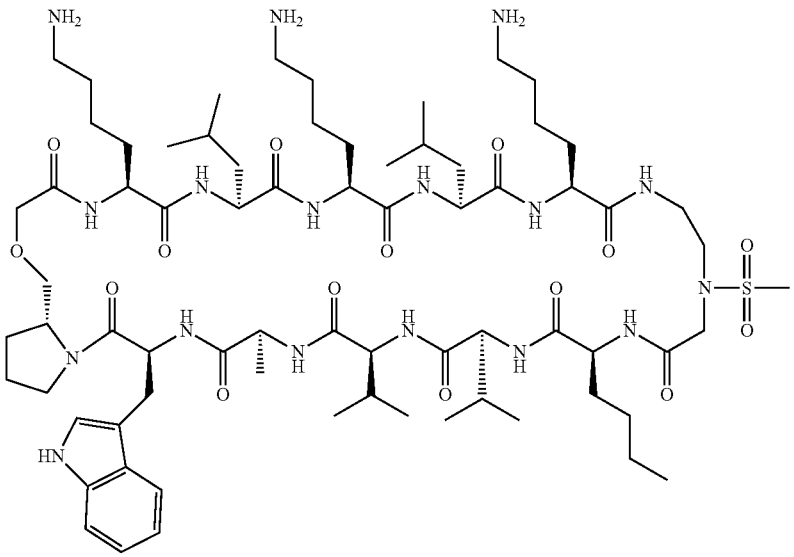

Compound A

An exemplary embodiment of the compounds disclosed herein ("Compound 2") shows increased potency relative to another known cyclic β-hairpin peptidomimetic compound ("Compound A"). Compound 2 was tested alongside Compound A and cell death was measured in a U266 myeloma cell line. Dapi staining was used for detection of dead cells and Fluo-4 was used for staining live cells. Cells were then imaged at 6 hours using a Cytation 5 Biotek imaging plate reader. Compound 2 showed more potency compared to Compound A, with results reported as the mean and error bars indicating standard deviation (see FIG. 1, n=3).

The preparation of the cysteine derivatives described in Example 4 can be performed according to or adapted from the protocols described in Yuko Tsuda, Chem. Pharm. Bull. 1991, 39, 607-611 which is hereby incorporated by reference in its entirety. Additionally, methods for synthesizing the compounds comprising cyclic β-hairpin peptidomimetics (e.g., Compound 1, Compound 2 and Compound 3) and derivatives thereof as described herein are known in the art (i.e., peptide synthesis), for example as described in U.S. Pat. No. 8,853,149 and U.S. Pub. No. 2014/0322227 which are hereby incorporated by reference in their entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/680,904, filed Jun. 5, 2018, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A compound having a structure of Formula (Ia):

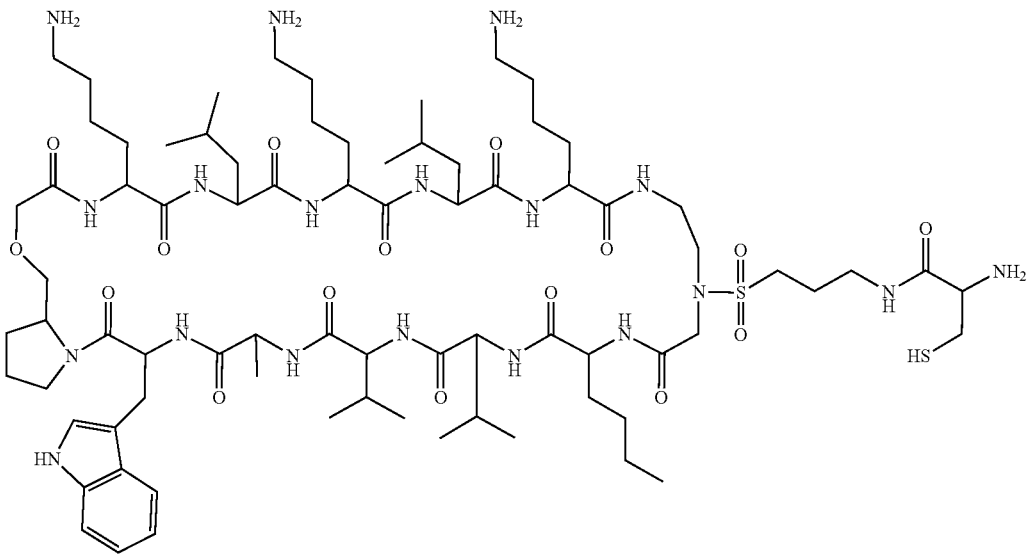 [SMILES: CCCCC1NC(=O)CN(S(=O)(=O)CCCNC(=O)C(N)CS)CCNC(=O)C(CCCCN)NC(=O)C(CC(C)C)NC(=O)C(CCCCN)NC(=O)C(CC(C)C)NC(=O)C(CCCCN)NC(=O)COCC2CCCN2C(=O)C(Cc2c[nH]c3ccccc23)NC(=O)C(C)NC(=O)C(C(C)C)NC(=O)C(C(C)C)NC1=O]

or a pharmaceutically acceptable salt, tautomer, or stereoisomer thereof.

2. The compound of claim 1, wherein the compound has the following structures:

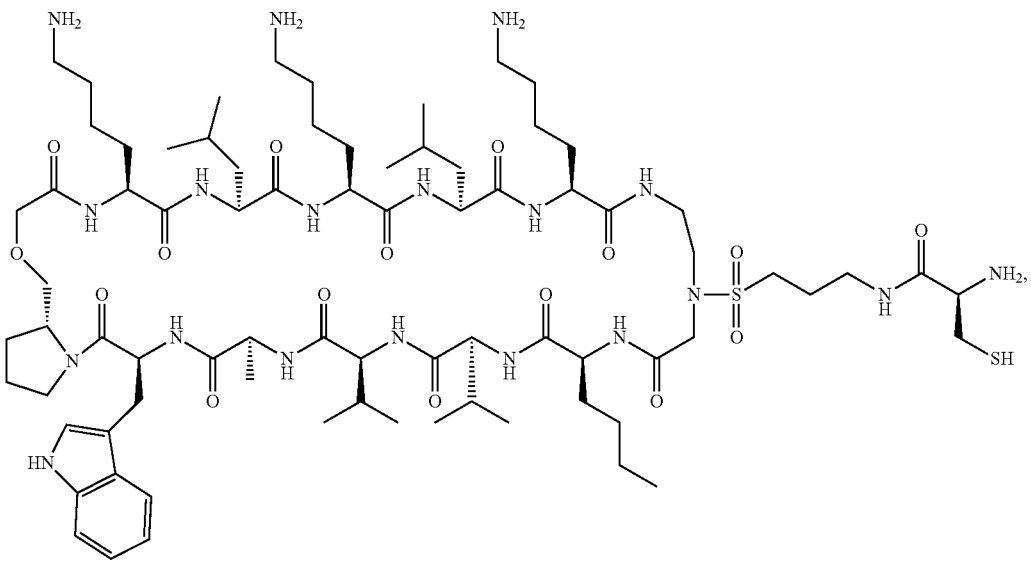 [SMILES: CCCC[C@@H]1NC(=O)CN(S(=O)(=O)CCCNC(=O)[C@@H](N)CS)CCNC(=O)[C@H](CCCCN)NC(=O)[C@H](CC(C)C)NC(=O)[C@H](CCCCN)NC(=O)[C@H](CC(C)C)NC(=O)[C@H](CCCCN)NC(=O)COC[C@H]2CCCN2C(=O)[C@H](Cc2c[nH]c3ccccc23)NC(=O)[C@H](C)NC(=O)[C@H](C(C)C)NC(=O)[C@H](C(C)C)NC1=O]

or a pharmaceutically acceptable salt, or tautomer thereof.

3. A pharmaceutical composition comprising the compound of claim 1 and a pharmaceutically acceptable carrier or excipient.

4. The pharmaceutical composition of claim 3, wherein the pharmaceutical composition is formulated for oral administration or injection.

* * * * *

```
                    SEQUENCE LISTING

<160> NUMBER OF SEQ ID NOS: 282

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
```

```
<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22
```

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27
<211> LENGTH: 5
<212> TYPE: PRT
<213> ORGANISM: Artificial Sequence
<220> FEATURE:
<223> OTHER INFORMATION: non-recognition sequence

<400> SEQUENCE: 27

Lys Leu Lys Leu Lys
1               5

<210> SEQ ID NO 28
<211> LENGTH: 5
<212> TYPE: PRT
<213> ORGANISM: Artificial Sequence
<220> FEATURE:
<223> OTHER INFORMATION: non-recognition sequence

<400> SEQUENCE: 28

Lys Leu Gln Leu Lys
1               5

<210> SEQ ID NO 29
<211> LENGTH: 5
<212> TYPE: PRT
<213> ORGANISM: Artificial Sequence
<220> FEATURE:
<223> OTHER INFORMATION: non-recognition sequence

<400> SEQUENCE: 29

Gln Leu Lys Leu Lys
1               5

<210> SEQ ID NO 30
<211> LENGTH: 5
<212> TYPE: PRT
<213> ORGANISM: Artificial Sequence
<220> FEATURE:
<223> OTHER INFORMATION: non-recognition sequence

<400> SEQUENCE: 30

```
Lys Gln Lys Leu Lys
1               5

<210> SEQ ID NO 31
<211> LENGTH: 5
<212> TYPE: PRT
<213> ORGANISM: Artificial Sequence
<220> FEATURE:
<223> OTHER INFORMATION: non-recognition sequence
<220> FEATURE:
<221> NAME/KEY: VARIANT
<222> LOCATION: 2,4
<223> OTHER INFORMATION: Xaa = sarcosine

<400> SEQUENCE: 31

Lys Xaa Lys Xaa Lys
1               5

<210> SEQ ID NO 32
<211> LENGTH: 5
<212> TYPE: PRT
<213> ORGANISM: Artificial Sequence
<220> FEATURE:
<223> OTHER INFORMATION: non-recognition sequence

<400> SEQUENCE: 32

Glu Leu Lys Leu Lys
1               5

<210> SEQ ID NO 33
<211> LENGTH: 5
<212> TYPE: PRT
<213> ORGANISM: Artificial Sequence
<220> FEATURE:
<223> OTHER INFORMATION: recognition sequence

<400> SEQUENCE: 33

Met Val Val Ser Trp
1               5

<210> SEQ ID NO 34
<211> LENGTH: 5
<212> TYPE: PRT
<213> ORGANISM: Artificial Sequence
<220> FEATURE:
<223> OTHER INFORMATION: Recognition sequence

<400> SEQUENCE: 34

Met Val Val Ser Ala
1               5

<210> SEQ ID NO 35
<211> LENGTH: 5
<212> TYPE: PRT
<213> ORGANISM: Artificial Sequence
<220> FEATURE:
<223> OTHER INFORMATION: Recognition sequence

<400> SEQUENCE: 35

Met Val Val Ala Trp
1               5

<210> SEQ ID NO 36
<211> LENGTH: 5
<212> TYPE: PRT
<213> ORGANISM: Artificial Sequence
<220> FEATURE:
```

```
<223> OTHER INFORMATION: Recognition sequence

<400> SEQUENCE: 36

Met Val Ala Ser Trp
1               5

<210> SEQ ID NO 37
<211> LENGTH: 5
<212> TYPE: PRT
<213> ORGANISM: Artificial Sequence
<220> FEATURE:
<223> OTHER INFORMATION: Recognition sequence

<400> SEQUENCE: 37

Met Ala Val Ser Trp
1               5

<210> SEQ ID NO 38
<211> LENGTH: 5
<212> TYPE: PRT
<213> ORGANISM: Artificial Sequence
<220> FEATURE:
<223> OTHER INFORMATION: Recognition sequence

<400> SEQUENCE: 38

Ala Val Val Ser Trp
1               5

<210> SEQ ID NO 39
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
<223> OTHER INFORMATION: Xaa = norleucine

<400> SEQUENCE: 39

Xaa Val Val Ser Trp
1               5

<210> SEQ ID NO 40
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
<223> OTHER INFORMATION: Xaa = norleucine

<400> SEQUENCE: 40

Xaa Val Val Tyr Trp
1               5

<210> SEQ ID NO 41
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
<223> OTHER INFORMATION: Xaa = norleucine
```

```
<400> SEQUENCE: 41

Xaa Val Val Ala Trp
1               5

<210> SEQ ID NO 42
<211> LENGTH: 5
<212> TYPE: PRT
<213> ORGANISM: Artificial Sequence
<220> FEATURE:
<223> OTHER INFORMATION: Recognition sequence

<400> SEQUENCE: 42

Ala Val Val Ala Trp
1               5

<210> SEQ ID NO 43
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
<223> OTHER INFORMATION: Xaa = norleucine

<400> SEQUENCE: 43

Xaa Ala Val Ala Trp
1               5

<210> SEQ ID NO 44
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
<223> OTHER INFORMATION: Xaa = norleucine

<400> SEQUENCE: 44

Xaa Val Ala Ala Trp
1               5

<210> SEQ ID NO 45
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
<223> OTHER INFORMATION: Xaa = norleucine

<400> SEQUENCE: 45

Xaa Val Leu Ala Trp
1               5

<210> SEQ ID NO 46
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
```

<223> OTHER INFORMATION: Xaa = norleucine

<400> SEQUENCE: 46

Xaa Val Ile Ala Trp
1               5

<210> SEQ ID NO 47
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 1
<223> OTHER INFORMATION: Xaa = norleucine

<400> SEQUENCE: 47

Xaa Val Phe Ala Trp
1               5

<210> SEQ ID NO 48
<211> LENGTH: 5
<212> TYPE: PRT
<213> ORGANISM: Artificial Sequence
<220> FEATURE:
<223> OTHER INFORMATION: Recognition sequence

<400> SEQUENCE: 48

Trp Ser Val Val Trp
1               5

<210> SEQ ID NO 49

<400> SEQUENCE: 49

000

<210> SEQ ID NO 50
<211> LENGTH: 5
<212> TYPE: PRT
<213> ORGANISM: Artificial Sequence
<220> FEATURE:
<223> OTHER INFORMATION: Recognition sequence

<400> SEQUENCE: 50

Trp Ala Val Ala Trp
1               5

<210> SEQ ID NO 51
<211> LENGTH: 5
<212> TYPE: PRT
<213> ORGANISM: Artificial Sequence
<220> FEATURE:
<223> OTHER INFORMATION: Recognition sequence

<400> SEQUENCE: 51

Trp Ala Val Ala Ala
1               5

<210> SEQ ID NO 52
<211> LENGTH: 5
<212> TYPE: PRT
<213> ORGANISM: Artificial Sequence
<220> FEATURE:
<223> OTHER INFORMATION: Recognition sequence

<400> SEQUENCE: 52

Trp Ala Val Ala Met
1               5

<210> SEQ ID NO 53
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 53

Trp Ala Val Ala Xaa
1               5

<210> SEQ ID NO 54
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 54

Trp Ala Val Val Xaa
1               5

<210> SEQ ID NO 55
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 55

Trp Ala Val Ser Xaa
1               5

<210> SEQ ID NO 56
<211> LENGTH: 5
<212> TYPE: PRT
<213> ORGANISM: Artificial Sequence
<220> FEATURE:
<223> OTHER INFORMATION: Recognition sequence

<400> SEQUENCE: 56

Trp Ala Ala Ala Trp
1               5

<210> SEQ ID NO 57
<211> LENGTH: 5
<212> TYPE: PRT
<213> ORGANISM: Artificial Sequence
<220> FEATURE:
<223> OTHER INFORMATION: Recognition sequence

<400> SEQUENCE: 57

Trp Ala Ala Ala Ala

```
1               5

<210> SEQ ID NO 58
<211> LENGTH: 5
<212> TYPE: PRT
<213> ORGANISM: Artificial Sequence
<220> FEATURE:
<223> OTHER INFORMATION: Recognition sequence

<400> SEQUENCE: 58

Trp Ala Ala Ala Met
1               5

<210> SEQ ID NO 59
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 59

Trp Ala Ala Ala Xaa
1               5

<210> SEQ ID NO 60
<211> LENGTH: 5
<212> TYPE: PRT
<213> ORGANISM: Artificial Sequence
<220> FEATURE:
<223> OTHER INFORMATION: Recognition sequence

<400> SEQUENCE: 60

Trp Ala Ala Val Trp
1               5

<210> SEQ ID NO 61
<211> LENGTH: 5
<212> TYPE: PRT
<213> ORGANISM: Artificial Sequence
<220> FEATURE:
<223> OTHER INFORMATION: Recognition sequence

<400> SEQUENCE: 61

Trp Ala Ala Val Ala
1               5

<210> SEQ ID NO 62
<211> LENGTH: 5
<212> TYPE: PRT
<213> ORGANISM: Artificial Sequence
<220> FEATURE:
<223> OTHER INFORMATION: Recognition sequence

<400> SEQUENCE: 62

Trp Ala Ala Val Met
1               5

<210> SEQ ID NO 63
<211> LENGTH: 5
<212> TYPE: PRT
<213> ORGANISM: Artificial Sequence
<220> FEATURE:
<223> OTHER INFORMATION: Recognition sequence
<220> FEATURE:
```

```
<221> NAME/KEY: VARIANT
<222> LOCATION: 5
<223> OTHER INFORMATION: Xaa = norleucine

<400> SEQUENCE: 63

Trp Ala Ala Val Xaa
1               5

<210> SEQ ID NO 64
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 64

Trp Ala Ala Ser Xaa
1               5

<210> SEQ ID NO 65
<211> LENGTH: 5
<212> TYPE: PRT
<213> ORGANISM: Artificial Sequence
<220> FEATURE:
<223> OTHER INFORMATION: Recognition sequence

<400> SEQUENCE: 65

Trp Val Val Ala Trp
1               5

<210> SEQ ID NO 66
<211> LENGTH: 5
<212> TYPE: PRT
<213> ORGANISM: Artificial Sequence
<220> FEATURE:
<223> OTHER INFORMATION: Recognition sequence

<400> SEQUENCE: 66

Trp Val Val Ala Ala
1               5

<210> SEQ ID NO 67
<211> LENGTH: 5
<212> TYPE: PRT
<213> ORGANISM: Artificial Sequence
<220> FEATURE:
<223> OTHER INFORMATION: Recognition sequence

<400> SEQUENCE: 67

Trp Val Val Ala Met
1               5

<210> SEQ ID NO 68
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 68
```

Trp Val Val Ala Xaa
1               5

<210> SEQ ID NO 69
<211> LENGTH: 5
<212> TYPE: PRT
<213> ORGANISM: Artificial Sequence
<220> FEATURE:
<223> OTHER INFORMATION: Recognition sequence

<400> SEQUENCE: 69

Trp Val Val Val Trp
1               5

<210> SEQ ID NO 70
<211> LENGTH: 5
<212> TYPE: PRT
<213> ORGANISM: Artificial Sequence
<220> FEATURE:
<223> OTHER INFORMATION: Recognition sequence

<400> SEQUENCE: 70

Trp Val Val Val Ala
1               5

<210> SEQ ID NO 71
<211> LENGTH: 5
<212> TYPE: PRT
<213> ORGANISM: Artificial Sequence
<220> FEATURE:
<223> OTHER INFORMATION: Recognition sequence

<400> SEQUENCE: 71

Trp Val Val Val Met
1               5

<210> SEQ ID NO 72
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 72

Trp Val Val Val Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 73

Trp Val Val Ser Xaa
1               5

<210> SEQ ID NO 74
<211> LENGTH: 5

```
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 74

Trp Val Ala Ala Xaa
1               5

<210> SEQ ID NO 75
<211> LENGTH: 5
<212> TYPE: PRT
<213> ORGANISM: Artificial Sequence
<220> FEATURE:
<223> OTHER INFORMATION: Recognition sequence

<400> SEQUENCE: 75

Trp Val Ala Val Trp
1               5

<210> SEQ ID NO 76
<211> LENGTH: 5
<212> TYPE: PRT
<213> ORGANISM: Artificial Sequence
<220> FEATURE:
<223> OTHER INFORMATION: Recognition sequence

<400> SEQUENCE: 76

Trp Val Ala Val Ala
1               5

<210> SEQ ID NO 77
<211> LENGTH: 5
<212> TYPE: PRT
<213> ORGANISM: Artificial Sequence
<220> FEATURE:
<223> OTHER INFORMATION: Recognition sequence

<400> SEQUENCE: 77

Trp Val Ala Val Met
1               5

<210> SEQ ID NO 78
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 78

Trp Val Ala Val Xaa
1               5

<210> SEQ ID NO 79
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
```

```
<222> LOCATION: 5
<223> OTHER INFORMATION: Xaa = norleucine

<400> SEQUENCE: 79

Trp Val Ala Ser Xaa
1               5

<210> SEQ ID NO 80
<211> LENGTH: 5
<212> TYPE: PRT
<213> ORGANISM: Artificial Sequence
<220> FEATURE:
<223> OTHER INFORMATION: Recognition sequence

<400> SEQUENCE: 80

Trp Ser Val Ala Trp
1               5

<210> SEQ ID NO 81
<211> LENGTH: 5
<212> TYPE: PRT
<213> ORGANISM: Artificial Sequence
<220> FEATURE:
<223> OTHER INFORMATION: Recognition sequence

<400> SEQUENCE: 81

Trp Ser Val Ala Ala
1               5

<210> SEQ ID NO 82
<211> LENGTH: 5
<212> TYPE: PRT
<213> ORGANISM: Artificial Sequence
<220> FEATURE:
<223> OTHER INFORMATION: Recognition sequence

<400> SEQUENCE: 82

Trp Ser Val Ala Met
1               5

<210> SEQ ID NO 83
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 83

Trp Ser Val Ala Xaa
1               5

<210> SEQ ID NO 84
<211> LENGTH: 5
<212> TYPE: PRT
<213> ORGANISM: Artificial Sequence
<220> FEATURE:
<223> OTHER INFORMATION: Recognition sequence

<400> SEQUENCE: 84

Trp Ser Val Val Ala
1               5

<210> SEQ ID NO 85
```

```
<211> LENGTH: 5
<212> TYPE: PRT
<213> ORGANISM: Artificial Sequence
<220> FEATURE:
<223> OTHER INFORMATION: Recognition sequence

<400> SEQUENCE: 85

Trp Ser Val Val Met
1               5

<210> SEQ ID NO 86
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 86

Trp Ser Val Val Xaa
1               5

<210> SEQ ID NO 87
<211> LENGTH: 5
<212> TYPE: PRT
<213> ORGANISM: Artificial Sequence
<220> FEATURE:
<223> OTHER INFORMATION: Recognition sequence

<400> SEQUENCE: 87

Trp Ser Val Ser Trp
1               5

<210> SEQ ID NO 88
<211> LENGTH: 5
<212> TYPE: PRT
<213> ORGANISM: Artificial Sequence
<220> FEATURE:
<223> OTHER INFORMATION: Recognition sequence

<400> SEQUENCE: 88

Trp Ser Val Ser Ala
1               5

<210> SEQ ID NO 89
<211> LENGTH: 5
<212> TYPE: PRT
<213> ORGANISM: Artificial Sequence
<220> FEATURE:
<223> OTHER INFORMATION: Recognition sequence

<400> SEQUENCE: 89

Trp Ser Val Ser Met
1               5

<210> SEQ ID NO 90
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine
```

```
<400> SEQUENCE: 90

Trp Ser Val Ser Xaa
1               5

<210> SEQ ID NO 91
<211> LENGTH: 5
<212> TYPE: PRT
<213> ORGANISM: Artificial Sequence
<220> FEATURE:
<223> OTHER INFORMATION: Recognition sequence

<400> SEQUENCE: 91

Trp Ser Ala Ala Trp
1               5

<210> SEQ ID NO 92
<211> LENGTH: 5
<212> TYPE: PRT
<213> ORGANISM: Artificial Sequence
<220> FEATURE:
<223> OTHER INFORMATION: Recognition sequence

<400> SEQUENCE: 92

Trp Ser Ala Ala Ala
1               5

<210> SEQ ID NO 93
<211> LENGTH: 5
<212> TYPE: PRT
<213> ORGANISM: Artificial Sequence
<220> FEATURE:
<223> OTHER INFORMATION: Recognition sequence

<400> SEQUENCE: 93

Trp Ser Ala Ala Met
1               5

<210> SEQ ID NO 94
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 94

Trp Ser Ala Ala Xaa
1               5

<210> SEQ ID NO 95
<211> LENGTH: 5
<212> TYPE: PRT
<213> ORGANISM: Artificial Sequence
<220> FEATURE:
<223> OTHER INFORMATION: Recognition sequence

<400> SEQUENCE: 95

Trp Ser Ala Val Trp
1               5

<210> SEQ ID NO 96
<211> LENGTH: 5
<212> TYPE: PRT
<213> ORGANISM: Artificial Sequence
```

```
<220> FEATURE:
<223> OTHER INFORMATION: Recognition sequence

<400> SEQUENCE: 96

Trp Ser Ala Val Ala
1               5

<210> SEQ ID NO 97
<211> LENGTH: 5
<212> TYPE: PRT
<213> ORGANISM: Artificial Sequence
<220> FEATURE:
<223> OTHER INFORMATION: Recognition sequence

<400> SEQUENCE: 97

Trp Ser Ala Val Met
1               5

<210> SEQ ID NO 98
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 98

Trp Ser Ala Val Xaa
1               5

<210> SEQ ID NO 99
<211> LENGTH: 5
<212> TYPE: PRT
<213> ORGANISM: Artificial Sequence
<220> FEATURE:
<223> OTHER INFORMATION: Recognition sequence

<400> SEQUENCE: 99

Trp Ser Ala Ser Trp
1               5

<210> SEQ ID NO 100
<211> LENGTH: 5
<212> TYPE: PRT
<213> ORGANISM: Artificial Sequence
<220> FEATURE:
<223> OTHER INFORMATION: Recognition sequence

<400> SEQUENCE: 100

Trp Ser Ala Ser Ala
1               5

<210> SEQ ID NO 101
<211> LENGTH: 5
<212> TYPE: PRT
<213> ORGANISM: Artificial Sequence
<220> FEATURE:
<223> OTHER INFORMATION: Recognition sequence

<400> SEQUENCE: 101

Trp Ser Ala Ser Met
1               5

<210> SEQ ID NO 102
```

```
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 102

Trp Ser Ala Ser Xaa
1               5

<210> SEQ ID NO 103
<211> LENGTH: 5
<212> TYPE: PRT
<213> ORGANISM: Artificial Sequence
<220> FEATURE:
<223> OTHER INFORMATION: Recognition sequence

<400> SEQUENCE: 103

Trp Tyr Val Ala Trp
1               5

<210> SEQ ID NO 104
<211> LENGTH: 5
<212> TYPE: PRT
<213> ORGANISM: Artificial Sequence
<220> FEATURE:
<223> OTHER INFORMATION: Recognition sequence

<400> SEQUENCE: 104

Trp Tyr Val Ala Ala
1               5

<210> SEQ ID NO 105
<211> LENGTH: 5
<212> TYPE: PRT
<213> ORGANISM: Artificial Sequence
<220> FEATURE:
<223> OTHER INFORMATION: Recognition sequence

<400> SEQUENCE: 105

Trp Tyr Val Ala Met
1               5

<210> SEQ ID NO 106
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 106

Trp Tyr Val Ala Xaa
1               5

<210> SEQ ID NO 107
<211> LENGTH: 5
<212> TYPE: PRT
<213> ORGANISM: Artificial Sequence
<220> FEATURE:
<223> OTHER INFORMATION: Recognition sequence
```

```
<400> SEQUENCE: 107

Trp Tyr Val Val Trp
1               5

<210> SEQ ID NO 108
<211> LENGTH: 5
<212> TYPE: PRT
<213> ORGANISM: Artificial Sequence
<220> FEATURE:
<223> OTHER INFORMATION: Recognition sequence

<400> SEQUENCE: 108

Trp Tyr Val Val Ala
1               5

<210> SEQ ID NO 109
<211> LENGTH: 5
<212> TYPE: PRT
<213> ORGANISM: Artificial Sequence
<220> FEATURE:
<223> OTHER INFORMATION: Recognition sequence

<400> SEQUENCE: 109

Trp Tyr Val Val Met
1               5

<210> SEQ ID NO 110
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 110

Trp Tyr Val Val Xaa
1               5

<210> SEQ ID NO 111
<211> LENGTH: 5
<212> TYPE: PRT
<213> ORGANISM: Artificial Sequence
<220> FEATURE:
<223> OTHER INFORMATION: Recognition sequence

<400> SEQUENCE: 111

Trp Tyr Val Ser Trp
1               5

<210> SEQ ID NO 112
<211> LENGTH: 5
<212> TYPE: PRT
<213> ORGANISM: Artificial Sequence
<220> FEATURE:
<223> OTHER INFORMATION: Recognition sequence

<400> SEQUENCE: 112

Trp Tyr Val Ser Ala
1               5

<210> SEQ ID NO 113
<211> LENGTH: 5
<212> TYPE: PRT
<213> ORGANISM: Artificial Sequence
```

```
<220> FEATURE:
<223> OTHER INFORMATION: Recognition sequence

<400> SEQUENCE: 113

Trp Tyr Val Ser Met
1               5

<210> SEQ ID NO 114
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 114

Trp Tyr Val Ser Xaa
1               5

<210> SEQ ID NO 115
<211> LENGTH: 5
<212> TYPE: PRT
<213> ORGANISM: Artificial Sequence
<220> FEATURE:
<223> OTHER INFORMATION: Recognition sequence

<400> SEQUENCE: 115

Trp Tyr Ala Ala Trp
1               5

<210> SEQ ID NO 116
<211> LENGTH: 5
<212> TYPE: PRT
<213> ORGANISM: Artificial Sequence
<220> FEATURE:
<223> OTHER INFORMATION: Recognition sequence

<400> SEQUENCE: 116

Trp Tyr Ala Ala Ala
1               5

<210> SEQ ID NO 117
<211> LENGTH: 5
<212> TYPE: PRT
<213> ORGANISM: Artificial Sequence
<220> FEATURE:
<223> OTHER INFORMATION: Recognition sequence

<400> SEQUENCE: 117

Trp Tyr Ala Ala Met
1               5

<210> SEQ ID NO 118
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa   = norleucine

<400> SEQUENCE: 118

Trp Tyr Ala Ala Xaa
```

```
1               5

<210> SEQ ID NO 119
<211> LENGTH: 5
<212> TYPE: PRT
<213> ORGANISM: Artificial Sequence
<220> FEATURE:
<223> OTHER INFORMATION: Recognition sequence

<400> SEQUENCE: 119

Trp Tyr Ala Ala Trp
1               5

<210> SEQ ID NO 120
<211> LENGTH: 5
<212> TYPE: PRT
<213> ORGANISM: Artificial Sequence
<220> FEATURE:
<223> OTHER INFORMATION: Recognition sequence

<400> SEQUENCE: 120

Trp Tyr Ala Val Ala
1               5

<210> SEQ ID NO 121
<211> LENGTH: 5
<212> TYPE: PRT
<213> ORGANISM: Artificial Sequence
<220> FEATURE:
<223> OTHER INFORMATION: Recognition sequence

<400> SEQUENCE: 121

Trp Tyr Ala Val Met
1               5

<210> SEQ ID NO 122
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 122

Trp Tyr Ala Val Xaa
1               5

<210> SEQ ID NO 123
<211> LENGTH: 5
<212> TYPE: PRT
<213> ORGANISM: Artificial Sequence
<220> FEATURE:
<223> OTHER INFORMATION: Recognition sequence

<400> SEQUENCE: 123

Trp Tyr Ala Ser Trp
1               5

<210> SEQ ID NO 124
<211> LENGTH: 5
<212> TYPE: PRT
<213> ORGANISM: Artificial Sequence
<220> FEATURE:
<223> OTHER INFORMATION: Recognition sequence
```

```
<400> SEQUENCE: 124

Trp Tyr Ala Ser Ala
1               5

<210> SEQ ID NO 125
<211> LENGTH: 5
<212> TYPE: PRT
<213> ORGANISM: Artificial Sequence
<220> FEATURE:
<223> OTHER INFORMATION: Recognition sequence

<400> SEQUENCE: 125

Trp Tyr Ala Ser Met
1               5

<210> SEQ ID NO 126
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 126

Trp Tyr Ala Ser Xaa
1               5

<210> SEQ ID NO 127
<211> LENGTH: 5
<212> TYPE: PRT
<213> ORGANISM: Artificial Sequence
<220> FEATURE:
<223> OTHER INFORMATION: Recognition sequence

<400> SEQUENCE: 127

Ala Ala Val Ala Ala
1               5

<210> SEQ ID NO 128
<211> LENGTH: 5
<212> TYPE: PRT
<213> ORGANISM: Artificial Sequence
<220> FEATURE:
<223> OTHER INFORMATION: Recognition sequence

<400> SEQUENCE: 128

Ala Ala Val Ala Met
1               5

<210> SEQ ID NO 129
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 129

Ala Ala Val Ala Xaa
1               5
```

```
<210> SEQ ID NO 130
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 130

Ala Ala Val Val Xaa
1               5

<210> SEQ ID NO 131
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 131

Ala Ala Val Ala Xaa
1               5

<210> SEQ ID NO 132
<211> LENGTH: 5
<212> TYPE: PRT
<213> ORGANISM: Artificial Sequence
<220> FEATURE:
<223> OTHER INFORMATION: Recognition sequence

<400> SEQUENCE: 132

Ala Ala Ala Ala Ala
1               5

<210> SEQ ID NO 133
<211> LENGTH: 5
<212> TYPE: PRT
<213> ORGANISM: Artificial Sequence
<220> FEATURE:
<223> OTHER INFORMATION: Recognition sequence

<400> SEQUENCE: 133

Ala Ala Ala Ala Met
1               5

<210> SEQ ID NO 134
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 134

Ala Ala Ala Ala Xaa
1               5

<210> SEQ ID NO 135
<211> LENGTH: 5
```

```
<212> TYPE: PRT
<213> ORGANISM: Artificial Sequence
<220> FEATURE:
<223> OTHER INFORMATION: Recognition sequence

<400> SEQUENCE: 135

Ala Ala Ala Val Trp
1               5

<210> SEQ ID NO 136
<211> LENGTH: 5
<212> TYPE: PRT
<213> ORGANISM: Artificial Sequence
<220> FEATURE:
<223> OTHER INFORMATION: Recognition sequence

<400> SEQUENCE: 136

Ala Ala Ala Val Ala
1               5

<210> SEQ ID NO 137
<211> LENGTH: 5
<212> TYPE: PRT
<213> ORGANISM: Artificial Sequence
<220> FEATURE:
<223> OTHER INFORMATION: Recognition sequence

<400> SEQUENCE: 137

Ala Ala Ala Val Met
1               5

<210> SEQ ID NO 138
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 138

Ala Ala Ala Val Xaa
1               5

<210> SEQ ID NO 139
<211> LENGTH: 5
<212> TYPE: PRT
<213> ORGANISM: Artificial Sequence
<220> FEATURE:
<223> OTHER INFORMATION: Recognition sequence

<400> SEQUENCE: 139

Ala Ala Ala Ser Met
1               5

<210> SEQ ID NO 140
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 140
```

```
Ala Ala Ala Ser Xaa
1               5

<210> SEQ ID NO 141
<211> LENGTH: 5
<212> TYPE: PRT
<213> ORGANISM: Artificial Sequence
<220> FEATURE:
<223> OTHER INFORMATION: Recognition sequence

<400> SEQUENCE: 141

Ala Val Val Ala Trp
1               5

<210> SEQ ID NO 142
<211> LENGTH: 5
<212> TYPE: PRT
<213> ORGANISM: Artificial Sequence
<220> FEATURE:
<223> OTHER INFORMATION: Recognition sequence

<400> SEQUENCE: 142

Ala Val Val Ala Ala
1               5

<210> SEQ ID NO 143
<211> LENGTH: 5
<212> TYPE: PRT
<213> ORGANISM: Artificial Sequence
<220> FEATURE:
<223> OTHER INFORMATION: Recognition sequence

<400> SEQUENCE: 143

Ala Val Val Ala Met
1               5

<210> SEQ ID NO 144
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 144

Ala Val Val Ala Xaa
1               5

<210> SEQ ID NO 145
<211> LENGTH: 5
<212> TYPE: PRT
<213> ORGANISM: Artificial Sequence
<220> FEATURE:
<223> OTHER INFORMATION: Recognition sequence

<400> SEQUENCE: 145

Ala Val Val Val Ala
1               5

<210> SEQ ID NO 146
<211> LENGTH: 5
<212> TYPE: PRT
<213> ORGANISM: Artificial Sequence
<220> FEATURE:
```

```
<223> OTHER INFORMATION: Recognition sequence

<400> SEQUENCE: 146

Ala Val Val Val Met
1               5

<210> SEQ ID NO 147
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 147

Ala Val Val Val Xaa
1               5

<210> SEQ ID NO 148
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 148

Ala Val Val Ser Xaa
1               5

<210> SEQ ID NO 149
<211> LENGTH: 5
<212> TYPE: PRT
<213> ORGANISM: Artificial Sequence
<220> FEATURE:
<223> OTHER INFORMATION: Recognition sequence

<400> SEQUENCE: 149

Ala Val Ala Ala Met
1               5

<210> SEQ ID NO 150
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 150

Ala Val Ala Ala Xaa
1               5

<210> SEQ ID NO 151
<211> LENGTH: 5
<212> TYPE: PRT
<213> ORGANISM: Artificial Sequence
<220> FEATURE:
<223> OTHER INFORMATION: Recognition sequence
```

```
<400> SEQUENCE: 151

Ala Val Ala Val Ala
1               5

<210> SEQ ID NO 152
<211> LENGTH: 5
<212> TYPE: PRT
<213> ORGANISM: Artificial Sequence
<220> FEATURE:
<223> OTHER INFORMATION: Recognition sequence

<400> SEQUENCE: 152

Ala Val Ala Val Met
1               5

<210> SEQ ID NO 153
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 153

Ala Val Ala Val Xaa
1               5

<210> SEQ ID NO 154
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 154

Ala Val Ala Ser Xaa
1               5

<210> SEQ ID NO 155
<211> LENGTH: 5
<212> TYPE: PRT
<213> ORGANISM: Artificial Sequence
<220> FEATURE:
<223> OTHER INFORMATION: Recognition sequence

<400> SEQUENCE: 155

Ala Ser Val Ala Trp
1               5

<210> SEQ ID NO 156
<211> LENGTH: 5
<212> TYPE: PRT
<213> ORGANISM: Artificial Sequence
<220> FEATURE:
<223> OTHER INFORMATION: Recognition sequence

<400> SEQUENCE: 156

Ala Ser Val Ala Ala
1               5
```

```
<210> SEQ ID NO 157
<211> LENGTH: 5
<212> TYPE: PRT
<213> ORGANISM: Artificial Sequence
<220> FEATURE:
<223> OTHER INFORMATION: Recognition sequence

<400> SEQUENCE: 157

Ala Ser Val Ala Met
1               5

<210> SEQ ID NO 158
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 158

Ala Ser Val Ala Xaa
1               5

<210> SEQ ID NO 159
<211> LENGTH: 5
<212> TYPE: PRT
<213> ORGANISM: Artificial Sequence
<220> FEATURE:
<223> OTHER INFORMATION: Recognition sequence

<400> SEQUENCE: 159

Ala Ser Val Val Trp
1               5

<210> SEQ ID NO 160
<211> LENGTH: 5
<212> TYPE: PRT
<213> ORGANISM: Artificial Sequence
<220> FEATURE:
<223> OTHER INFORMATION: Recognition sequence

<400> SEQUENCE: 160

Ala Ser Val Val Ala
1               5

<210> SEQ ID NO 161
<211> LENGTH: 5
<212> TYPE: PRT
<213> ORGANISM: Artificial Sequence
<220> FEATURE:
<223> OTHER INFORMATION: Recognition sequence

<400> SEQUENCE: 161

Ala Ser Val Val Met
1               5

<210> SEQ ID NO 162
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine
```

```
<400> SEQUENCE: 162

Ala Ser Val Val Xaa
1               5

<210> SEQ ID NO 163
<211> LENGTH: 5
<212> TYPE: PRT
<213> ORGANISM: Artificial Sequence
<220> FEATURE:
<223> OTHER INFORMATION: Recognition sequence

<400> SEQUENCE: 163

Ala Ser Val Ser Ala
1               5

<210> SEQ ID NO 164
<211> LENGTH: 5
<212> TYPE: PRT
<213> ORGANISM: Artificial Sequence
<220> FEATURE:
<223> OTHER INFORMATION: Recognition sequence

<400> SEQUENCE: 164

Ala Ser Val Ser Met
1               5

<210> SEQ ID NO 165
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 165

Ala Ser Val Ser Xaa
1               5

<210> SEQ ID NO 166
<211> LENGTH: 5
<212> TYPE: PRT
<213> ORGANISM: Artificial Sequence
<220> FEATURE:
<223> OTHER INFORMATION: Recognition sequence

<400> SEQUENCE: 166

Ala Ser Ala Ala Trp
1               5

<210> SEQ ID NO 167
<211> LENGTH: 5
<212> TYPE: PRT
<213> ORGANISM: Artificial Sequence
<220> FEATURE:
<223> OTHER INFORMATION: Recognition sequence

<400> SEQUENCE: 167

Ala Ser Ala Ala Ala
1               5

<210> SEQ ID NO 168
<211> LENGTH: 5
<212> TYPE: PRT
```

```
<213> ORGANISM: Artificial Sequence
<220> FEATURE:
<223> OTHER INFORMATION: Recognition sequence

<400> SEQUENCE: 168

Ala Ser Ala Ala Met
1               5

<210> SEQ ID NO 169
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 169

Ala Ser Ala Ala Xaa
1               5

<210> SEQ ID NO 170
<211> LENGTH: 5
<212> TYPE: PRT
<213> ORGANISM: Artificial Sequence
<220> FEATURE:
<223> OTHER INFORMATION: Recognition sequence

<400> SEQUENCE: 170

Ala Ser Ala Val Trp
1               5

<210> SEQ ID NO 171
<211> LENGTH: 5
<212> TYPE: PRT
<213> ORGANISM: Artificial Sequence
<220> FEATURE:
<223> OTHER INFORMATION: Recognition sequence

<400> SEQUENCE: 171

Ala Ser Ala Val Ala
1               5

<210> SEQ ID NO 172
<211> LENGTH: 5
<212> TYPE: PRT
<213> ORGANISM: Artificial Sequence
<220> FEATURE:
<223> OTHER INFORMATION: Recognition sequence

<400> SEQUENCE: 172

Ala Ser Ala Val Met
1               5

<210> SEQ ID NO 173
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 173
```

```
Ala Ser Ala Val Xaa
1               5

<210> SEQ ID NO 174
<211> LENGTH: 5
<212> TYPE: PRT
<213> ORGANISM: Artificial Sequence
<220> FEATURE:
<223> OTHER INFORMATION: Recognition sequence

<400> SEQUENCE: 174

Ala Ser Ala Ser Ala
1               5

<210> SEQ ID NO 175
<211> LENGTH: 5
<212> TYPE: PRT
<213> ORGANISM: Artificial Sequence
<220> FEATURE:
<223> OTHER INFORMATION: Recognition sequence

<400> SEQUENCE: 175

Ala Ser Ala Ser Met
1               5

<210> SEQ ID NO 176
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 176

Ala Ser Ala Ser Xaa
1               5

<210> SEQ ID NO 177
<211> LENGTH: 5
<212> TYPE: PRT
<213> ORGANISM: Artificial Sequence
<220> FEATURE:
<223> OTHER INFORMATION: Recognition sequence

<400> SEQUENCE: 177

Ala Tyr Val Ala Trp
1               5

<210> SEQ ID NO 178
<211> LENGTH: 5
<212> TYPE: PRT
<213> ORGANISM: Artificial Sequence
<220> FEATURE:
<223> OTHER INFORMATION: Recognition sequence

<400> SEQUENCE: 178

Ala Tyr Val Ala Ala
1               5

<210> SEQ ID NO 179
<211> LENGTH: 5
<212> TYPE: PRT
<213> ORGANISM: Artificial Sequence
<220> FEATURE:
<223> OTHER INFORMATION: Recognition sequence
```

```
<400> SEQUENCE: 179

Ala Tyr Val Ala Met
1               5

<210> SEQ ID NO 180
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa  = norleucine

<400> SEQUENCE: 180

Ala Tyr Val Ala Xaa
1               5

<210> SEQ ID NO 181
<211> LENGTH: 5
<212> TYPE: PRT
<213> ORGANISM: Artificial Sequence
<220> FEATURE:
<223> OTHER INFORMATION: Recognition sequence

<400> SEQUENCE: 181

Ala Tyr Val Val Trp
1               5

<210> SEQ ID NO 182
<211> LENGTH: 5
<212> TYPE: PRT
<213> ORGANISM: Artificial Sequence
<220> FEATURE:
<223> OTHER INFORMATION: Recognition sequence

<400> SEQUENCE: 182

Ala Tyr Val Val Ala
1               5

<210> SEQ ID NO 183
<211> LENGTH: 5
<212> TYPE: PRT
<213> ORGANISM: Artificial Sequence
<220> FEATURE:
<223> OTHER INFORMATION: Recognition sequence

<400> SEQUENCE: 183

Ala Tyr Val Val Met
1               5

<210> SEQ ID NO 184
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 184

Ala Tyr Val Val Xaa
1               5
```

```
<210> SEQ ID NO 185
<211> LENGTH: 5
<212> TYPE: PRT
<213> ORGANISM: Artificial Sequence
<220> FEATURE:
<223> OTHER INFORMATION: Recognition sequence

<400> SEQUENCE: 185

Ala Tyr Val Ser Trp
1               5

<210> SEQ ID NO 186
<211> LENGTH: 5
<212> TYPE: PRT
<213> ORGANISM: Artificial Sequence
<220> FEATURE:
<223> OTHER INFORMATION: Recognition sequence

<400> SEQUENCE: 186

Ala Tyr Val Ser Ala
1               5

<210> SEQ ID NO 187
<211> LENGTH: 5
<212> TYPE: PRT
<213> ORGANISM: Artificial Sequence
<220> FEATURE:
<223> OTHER INFORMATION: Recognition sequence

<400> SEQUENCE: 187

Ala Tyr Val Ser Met
1               5

<210> SEQ ID NO 188
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 188

Ala Tyr Val Ser Xaa
1               5

<210> SEQ ID NO 189
<211> LENGTH: 5
<212> TYPE: PRT
<213> ORGANISM: Artificial Sequence
<220> FEATURE:
<223> OTHER INFORMATION: Recognition sequence

<400> SEQUENCE: 189

Ala Tyr Ala Ala Trp
1               5

<210> SEQ ID NO 190
<211> LENGTH: 5
<212> TYPE: PRT
<213> ORGANISM: Artificial Sequence
<220> FEATURE:
<223> OTHER INFORMATION: Recognition sequence

<400> SEQUENCE: 190
```

Ala Tyr Ala Ala Ala
1               5

<210> SEQ ID NO 191
<211> LENGTH: 5
<212> TYPE: PRT
<213> ORGANISM: Artificial Sequence
<220> FEATURE:
<223> OTHER INFORMATION: Recognition sequence

<400> SEQUENCE: 191

Ala Tyr Ala Ala Met
1               5

<210> SEQ ID NO 192
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 192

Ala Tyr Ala Ala Xaa
1               5

<210> SEQ ID NO 193
<211> LENGTH: 5
<212> TYPE: PRT
<213> ORGANISM: Artificial Sequence
<220> FEATURE:
<223> OTHER INFORMATION: Recognition sequence

<400> SEQUENCE: 193

Ala Tyr Ala Val Trp
1               5

<210> SEQ ID NO 194
<211> LENGTH: 5
<212> TYPE: PRT
<213> ORGANISM: Artificial Sequence
<220> FEATURE:
<223> OTHER INFORMATION: Recognition sequence

<400> SEQUENCE: 194

Ala Tyr Ala Val Ala
1               5

<210> SEQ ID NO 195
<211> LENGTH: 5
<212> TYPE: PRT
<213> ORGANISM: Artificial Sequence
<220> FEATURE:
<223> OTHER INFORMATION: Recognition sequence

<400> SEQUENCE: 195

Ala Tyr Ala Val Met
1               5

<210> SEQ ID NO 196
<211> LENGTH: 5
<212> TYPE: PRT
<213> ORGANISM: Artificial Sequence
<220> FEATURE:
<223> OTHER INFORMATION: Recognition sequence

```
<220> FEATURE:
<221> NAME/KEY: VARIANT
<222> LOCATION: 5
<223> OTHER INFORMATION: Xaa = norleucine

<400> SEQUENCE: 196

Ala Tyr Ala Val Xaa
1               5

<210> SEQ ID NO 197
<211> LENGTH: 5
<212> TYPE: PRT
<213> ORGANISM: Artificial Sequence
<220> FEATURE:
<223> OTHER INFORMATION: Recognition sequence

<400> SEQUENCE: 197

Ala Tyr Ala Ser Trp
1               5

<210> SEQ ID NO 198
<211> LENGTH: 5
<212> TYPE: PRT
<213> ORGANISM: Artificial Sequence
<220> FEATURE:
<223> OTHER INFORMATION: Recognition sequence

<400> SEQUENCE: 198

Ala Tyr Ala Ser Ala
1               5

<210> SEQ ID NO 199
<211> LENGTH: 5
<212> TYPE: PRT
<213> ORGANISM: Artificial Sequence
<220> FEATURE:
<223> OTHER INFORMATION: Recognition sequence

<400> SEQUENCE: 199

Ala Tyr Ala Ser Met
1               5

<210> SEQ ID NO 200
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 200

Ala Tyr Ala Ser Xaa
1               5

<210> SEQ ID NO 201
<211> LENGTH: 5
<212> TYPE: PRT
<213> ORGANISM: Artificial Sequence
<220> FEATURE:
<223> OTHER INFORMATION: Recognition sequence

<400> SEQUENCE: 201

Met Ala Val Ala Ala
1               5
```

```
<210> SEQ ID NO 202
<211> LENGTH: 5
<212> TYPE: PRT
<213> ORGANISM: Artificial Sequence
<220> FEATURE:
<223> OTHER INFORMATION: Recognition sequence

<400> SEQUENCE: 202

Met Ala Val Ala Met
1               5

<210> SEQ ID NO 203
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 203

Met Ala Val Ala Xaa
1               5

<210> SEQ ID NO 204
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 204

Met Ala Val Val Xaa
1               5

<210> SEQ ID NO 205
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 205

Met Ala Val Ser Xaa
1               5

<210> SEQ ID NO 206
<211> LENGTH: 5
<212> TYPE: PRT
<213> ORGANISM: Artificial Sequence
<220> FEATURE:
<223> OTHER INFORMATION: Recognition sequence

<400> SEQUENCE: 206

Met Ala Ala Ala Ala
1               5

<210> SEQ ID NO 207
```

```
<211> LENGTH: 5
<212> TYPE: PRT
<213> ORGANISM: Artificial Sequence
<220> FEATURE:
<223> OTHER INFORMATION: Recognition sequence

<400> SEQUENCE: 207

Met Ala Ala Ala Met
1               5

<210> SEQ ID NO 208
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 208

Met Ala Ala Ala Xaa
1               5

<210> SEQ ID NO 209
<211> LENGTH: 5
<212> TYPE: PRT
<213> ORGANISM: Artificial Sequence
<220> FEATURE:
<223> OTHER INFORMATION: Recognition sequence

<400> SEQUENCE: 209

Met Ala Ala Val Trp
1               5

<210> SEQ ID NO 210
<211> LENGTH: 5
<212> TYPE: PRT
<213> ORGANISM: Artificial Sequence
<220> FEATURE:
<223> OTHER INFORMATION: Recognition sequence

<400> SEQUENCE: 210

Met Ala Ala Val Ala
1               5

<210> SEQ ID NO 211
<211> LENGTH: 5
<212> TYPE: PRT
<213> ORGANISM: Artificial Sequence
<220> FEATURE:
<223> OTHER INFORMATION: Recognition sequence

<400> SEQUENCE: 211

Met Ala Ala Val Met
1               5

<210> SEQ ID NO 212
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine
```

```
<400> SEQUENCE: 212

Met Ala Ala Val Xaa
1               5

<210> SEQ ID NO 213
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 213

Met Ala Ala Ser Xaa
1               5

<210> SEQ ID NO 214
<211> LENGTH: 5
<212> TYPE: PRT
<213> ORGANISM: Artificial Sequence
<220> FEATURE:
<223> OTHER INFORMATION: Recognition sequence

<400> SEQUENCE: 214

Met Val Val Ala Trp
1               5

<210> SEQ ID NO 215
<211> LENGTH: 5
<212> TYPE: PRT
<213> ORGANISM: Artificial Sequence
<220> FEATURE:
<223> OTHER INFORMATION: Recognition sequence

<400> SEQUENCE: 215

Met Val Val Ala Ala
1               5

<210> SEQ ID NO 216
<211> LENGTH: 5
<212> TYPE: PRT
<213> ORGANISM: Artificial Sequence
<220> FEATURE:
<223> OTHER INFORMATION: Recognition sequence

<400> SEQUENCE: 216

Met Val Val Ala Met
1               5

<210> SEQ ID NO 217
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 217

Met Val Val Ala Xaa
1               5
```

```
<210> SEQ ID NO 218
<211> LENGTH: 5
<212> TYPE: PRT
<213> ORGANISM: Artificial Sequence
<220> FEATURE:
<223> OTHER INFORMATION: Recognition sequence

<400> SEQUENCE: 218

Met Val Val Val Met
1               5

<210> SEQ ID NO 219
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 219

Met Val Val Val Xaa
1               5

<210> SEQ ID NO 220
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 220

Met Val Val Ser Xaa
1               5

<210> SEQ ID NO 221
<211> LENGTH: 5
<212> TYPE: PRT
<213> ORGANISM: Artificial Sequence
<220> FEATURE:
<223> OTHER INFORMATION: Recognition sequence

<400> SEQUENCE: 221

Met Val Ala Ala Met
1               5

<210> SEQ ID NO 222
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 222

Met Val Ala Ala Xaa
1               5

<210> SEQ ID NO 223
<211> LENGTH: 5
```

```
<212> TYPE: PRT
<213> ORGANISM: Artificial Sequence
<220> FEATURE:
<223> OTHER INFORMATION: Recognition sequence

<400> SEQUENCE: 223

Met Val Ala Val Met
1               5

<210> SEQ ID NO 224
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 224

Met Val Ala Val Xaa
1               5

<210> SEQ ID NO 225
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 225

Met Val Ala Ser Xaa
1               5

<210> SEQ ID NO 226
<211> LENGTH: 5
<212> TYPE: PRT
<213> ORGANISM: Artificial Sequence
<220> FEATURE:
<223> OTHER INFORMATION: Recognition sequence

<400> SEQUENCE: 226

Met Ser Val Ala Trp
1               5

<210> SEQ ID NO 227
<211> LENGTH: 5
<212> TYPE: PRT
<213> ORGANISM: Artificial Sequence
<220> FEATURE:
<223> OTHER INFORMATION: Recognition sequence

<400> SEQUENCE: 227

Met Ser Val Ala Ala
1               5

<210> SEQ ID NO 228
<211> LENGTH: 5
<212> TYPE: PRT
<213> ORGANISM: Artificial Sequence
<220> FEATURE:
<223> OTHER INFORMATION: Recognition sequence

<400> SEQUENCE: 228
```

```
Met Ser Val Ala Met
1               5

<210> SEQ ID NO 229
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 229

Met Ser Val Ala Xaa
1               5

<210> SEQ ID NO 230
<211> LENGTH: 5
<212> TYPE: PRT
<213> ORGANISM: Artificial Sequence
<220> FEATURE:
<223> OTHER INFORMATION: Recognition sequence

<400> SEQUENCE: 230

Met Ser Val Val Trp
1               5

<210> SEQ ID NO 231
<211> LENGTH: 5
<212> TYPE: PRT
<213> ORGANISM: Artificial Sequence
<220> FEATURE:
<223> OTHER INFORMATION: Recognition sequence

<400> SEQUENCE: 231

Met Ser Val Val Ala
1               5

<210> SEQ ID NO 232
<211> LENGTH: 5
<212> TYPE: PRT
<213> ORGANISM: Artificial Sequence
<220> FEATURE:
<223> OTHER INFORMATION: Recognition sequence

<400> SEQUENCE: 232

Met Ser Val Val Met
1               5

<210> SEQ ID NO 233
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 233

Met Ser Val Val Xaa
1               5

<210> SEQ ID NO 234
```

```
<211> LENGTH: 5
<212> TYPE: PRT
<213> ORGANISM: Artificial Sequence
<220> FEATURE:
<223> OTHER INFORMATION: Recognition sequence

<400> SEQUENCE: 234

Met Ser Val Ser Met
1               5

<210> SEQ ID NO 235
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 235

Met Ser Val Ser Xaa
1               5

<210> SEQ ID NO 236
<211> LENGTH: 5
<212> TYPE: PRT
<213> ORGANISM: Artificial Sequence
<220> FEATURE:
<223> OTHER INFORMATION: Recognition sequence

<400> SEQUENCE: 236

Met Ser Ala Ala Trp
1               5

<210> SEQ ID NO 237
<211> LENGTH: 5
<212> TYPE: PRT
<213> ORGANISM: Artificial Sequence
<220> FEATURE:
<223> OTHER INFORMATION: Recognition sequence

<400> SEQUENCE: 237

Met Ser Ala Ala Ala
1               5

<210> SEQ ID NO 238
<211> LENGTH: 5
<212> TYPE: PRT
<213> ORGANISM: Artificial Sequence
<220> FEATURE:
<223> OTHER INFORMATION: Recognition sequence

<400> SEQUENCE: 238

Met Ser Ala Ala Met
1               5

<210> SEQ ID NO 239
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine
```

<400> SEQUENCE: 239

Met Ser Ala Ala Xaa
1               5

<210> SEQ ID NO 240
<211> LENGTH: 5
<212> TYPE: PRT
<213> ORGANISM: Artificial Sequence
<220> FEATURE:
<223> OTHER INFORMATION: Recognition sequence

<400> SEQUENCE: 240

Met Ser Ala Val Trp
1               5

<210> SEQ ID NO 241
<211> LENGTH: 5
<212> TYPE: PRT
<213> ORGANISM: Artificial Sequence
<220> FEATURE:
<223> OTHER INFORMATION: Recognition sequence

<400> SEQUENCE: 241

Met Ser Ala Val Ala
1               5

<210> SEQ ID NO 242
<211> LENGTH: 5
<212> TYPE: PRT
<213> ORGANISM: Artificial Sequence
<220> FEATURE:
<223> OTHER INFORMATION: Recognition sequence

<400> SEQUENCE: 242

Met Ser Ala Val Met
1               5

<210> SEQ ID NO 243
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 243

Met Ser Ala Val Xaa
1               5

<210> SEQ ID NO 244
<211> LENGTH: 5
<212> TYPE: PRT
<213> ORGANISM: Artificial Sequence
<220> FEATURE:
<223> OTHER INFORMATION: Recognition sequence

<400> SEQUENCE: 244

Met Ser Ala Ser Met
1               5

<210> SEQ ID NO 245
<211> LENGTH: 5
<212> TYPE: PRT
<213> ORGANISM: Artificial Sequence

```
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 245

Met Ser Ala Ser Xaa
1               5

<210> SEQ ID NO 246
<211> LENGTH: 5
<212> TYPE: PRT
<213> ORGANISM: Artificial Sequence
<220> FEATURE:
<223> OTHER INFORMATION: Recognition sequence

<400> SEQUENCE: 246

Met Tyr Val Ala Trp
1               5

<210> SEQ ID NO 247
<211> LENGTH: 5
<212> TYPE: PRT
<213> ORGANISM: Artificial Sequence
<220> FEATURE:
<223> OTHER INFORMATION: Recognition sequence

<400> SEQUENCE: 247

Met Tyr Val Ala Ala
1               5

<210> SEQ ID NO 248
<211> LENGTH: 5
<212> TYPE: PRT
<213> ORGANISM: Artificial Sequence
<220> FEATURE:
<223> OTHER INFORMATION: Recognition sequence

<400> SEQUENCE: 248

Met Tyr Val Ala Met
1               5

<210> SEQ ID NO 249
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 249

Met Tyr Val Ala Xaa
1               5

<210> SEQ ID NO 250
<211> LENGTH: 5
<212> TYPE: PRT
<213> ORGANISM: Artificial Sequence
<220> FEATURE:
<223> OTHER INFORMATION: Recognition sequence

<400> SEQUENCE: 250

Met Tyr Val Val Trp
```

1               5

<210> SEQ ID NO 251
<211> LENGTH: 5
<212> TYPE: PRT
<213> ORGANISM: Artificial Sequence
<220> FEATURE:
<223> OTHER INFORMATION: Recognition sequence

<400> SEQUENCE: 251

Met Tyr Val Val Ala
1               5

<210> SEQ ID NO 252
<211> LENGTH: 5
<212> TYPE: PRT
<213> ORGANISM: Artificial Sequence
<220> FEATURE:
<223> OTHER INFORMATION: Recognition sequence

<400> SEQUENCE: 252

Met Tyr Val Val Met
1               5

<210> SEQ ID NO 253
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 253

Met Tyr Val Val Xaa
1               5

<210> SEQ ID NO 254
<211> LENGTH: 5
<212> TYPE: PRT
<213> ORGANISM: Artificial Sequence
<220> FEATURE:
<223> OTHER INFORMATION: Recognition sequence

<400> SEQUENCE: 254

Met Tyr Val Ser Trp
1               5

<210> SEQ ID NO 255
<211> LENGTH: 5
<212> TYPE: PRT
<213> ORGANISM: Artificial Sequence
<220> FEATURE:
<223> OTHER INFORMATION: Recognition sequence

<400> SEQUENCE: 255

Met Tyr Val Ser Ala
1               5

<210> SEQ ID NO 256
<211> LENGTH: 5
<212> TYPE: PRT
<213> ORGANISM: Artificial Sequence
<220> FEATURE:
<223> OTHER INFORMATION: Recognition sequence

```
<400> SEQUENCE: 256

Met Tyr Val Ser Met
1               5

<210> SEQ ID NO 257
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 257

Met Tyr Val Ser Xaa
1               5

<210> SEQ ID NO 258
<211> LENGTH: 5
<212> TYPE: PRT
<213> ORGANISM: Artificial Sequence
<220> FEATURE:
<223> OTHER INFORMATION: Recognition sequence

<400> SEQUENCE: 258

Met Tyr Ala Ala Trp
1               5

<210> SEQ ID NO 259
<211> LENGTH: 5
<212> TYPE: PRT
<213> ORGANISM: Artificial Sequence
<220> FEATURE:
<223> OTHER INFORMATION: Recognition sequence

<400> SEQUENCE: 259

Met Tyr Ala Ala Ala
1               5

<210> SEQ ID NO 260
<211> LENGTH: 5
<212> TYPE: PRT
<213> ORGANISM: Artificial Sequence
<220> FEATURE:
<223> OTHER INFORMATION: Recognition sequence

<400> SEQUENCE: 260

Met Tyr Ala Ala Met
1               5

<210> SEQ ID NO 261
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 261

Met Tyr Ala Ala Xaa
1               5
```

```
<210> SEQ ID NO 262
<211> LENGTH: 5
<212> TYPE: PRT
<213> ORGANISM: Artificial Sequence
<220> FEATURE:
<223> OTHER INFORMATION: Recognition sequence

<400> SEQUENCE: 262

Met Tyr Ala Val Trp
1               5

<210> SEQ ID NO 263
<211> LENGTH: 5
<212> TYPE: PRT
<213> ORGANISM: Artificial Sequence
<220> FEATURE:
<223> OTHER INFORMATION: Recognition sequence

<400> SEQUENCE: 263

Met Tyr Ala Val Ala
1               5

<210> SEQ ID NO 264
<211> LENGTH: 5
<212> TYPE: PRT
<213> ORGANISM: Artificial Sequence
<220> FEATURE:
<223> OTHER INFORMATION: Recognition sequence

<400> SEQUENCE: 264

Met Tyr Ala Val Met
1               5

<210> SEQ ID NO 265
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 265

Met Tyr Ala Val Xaa
1               5

<210> SEQ ID NO 266
<211> LENGTH: 5
<212> TYPE: PRT
<213> ORGANISM: Artificial Sequence
<220> FEATURE:
<223> OTHER INFORMATION: Recognition sequence

<400> SEQUENCE: 266

Met Tyr Ala Ser Trp
1               5

<210> SEQ ID NO 267
<211> LENGTH: 5
<212> TYPE: PRT
<213> ORGANISM: Artificial Sequence
<220> FEATURE:
<223> OTHER INFORMATION: Recognition sequence

<400> SEQUENCE: 267

Met Tyr Ala Ser Ala
```

```
1               5

<210> SEQ ID NO 268
<211> LENGTH: 5
<212> TYPE: PRT
<213> ORGANISM: Artificial Sequence
<220> FEATURE:
<223> OTHER INFORMATION: Recognition sequence

<400> SEQUENCE: 268

Met Tyr Ala Ser Met
1               5

<210> SEQ ID NO 269
<211> LENGTH: 5
<212> TYPE: PRT
<213> ORGANISM: Artificial Sequence
<220> FEATURE:
<223> OTHER INFORMATION: Recognition sequence
<220> FEATURE:
<221> NAME/KEY: VARIANT
<222> LOCATION: 5
<223> OTHER INFORMATION: Xaa = norleucine

<400> SEQUENCE: 269

Met Tyr Ala Ser Xaa
1               5

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000
```

```
<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281
<211> LENGTH: 5
<212> TYPE: PRT
<213> ORGANISM: Artificial Sequence
<220> FEATURE:
<223> OTHER INFORMATION: Recognition sequence

<400> SEQUENCE: 281

Lys Leu Lys Leu Gln
1               5

<210> SEQ ID NO 282
<211> LENGTH: 5
<212> TYPE: PRT
<213> ORGANISM: Artificial Sequence
<220> FEATURE:
<223> OTHER INFORMATION: Recognition sequence

<400> SEQUENCE: 282

Lys Leu Lys Gln Lys
1               5
```